(12) United States Patent
Shankar et al.

(10) Patent No.: US 7,750,158 B2
(45) Date of Patent: Jul. 6, 2010

(54) CANNABINOID RECEPTOR LIGANDS

(75) Inventors: Bandarpalle B. Shankar, Branchburg, NJ (US); Eric Gilbert, Scotch Plains, NJ (US); Razia K. Rizvi, Bloomfield, NJ (US); Chunli Huang, Springfield, NJ (US); Joseph A. Kozlowski, Princeton, NJ (US); Stuart McCombie, Caldwell, NJ (US); Neng-Yang Shih, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 884 days.

(21) Appl. No.: 11/157,510

(22) Filed: Jun. 21, 2005

(65) Prior Publication Data

US 2006/0100228 A1  May 11, 2006

Related U.S. Application Data

(60) Provisional application No. 60/581,837, filed on Jun. 22, 2004.

(51) Int. Cl.
*C07D 221/00* (2006.01)
*A61K 31/44* (2006.01)

(52) U.S. Cl. ......................... 546/16; 514/278
(58) Field of Classification Search .................. 546/16; 514/278
See application file for complete search history.

(56) References Cited

U.S. PATENT DOCUMENTS

| | | |
|---|---|---|
| 5,338,753 A | 8/1994 | Burstein et al. |
| 5,462,960 A | 10/1995 | Barth et al. |
| 5,532,237 A | 7/1996 | Gallant et al. |
| 5,925,768 A | 7/1999 | Barth et al. |
| 5,948,777 A | 9/1999 | Bender et al. |
| 5,990,170 A | 11/1999 | Della Valle et al. |
| 6,013,648 A | 1/2000 | Rinaldi et al. |
| 6,017,919 A | 1/2000 | Inaba et al. |

FOREIGN PATENT DOCUMENTS

| | | |
|---|---|---|
| WO | WO 03/042174 A1 | 5/2003 |
| WO | WO 2005/037216 A2 | 4/2005 |

OTHER PUBLICATIONS

F Zaragoza Dorwald Side Reactions in Organic Synthesis 2005, Wiley-VCH.*
R.G. Pertwee, "Pharmacology of Cannabinoid Receptor Ligands", Current Medicinal Chemistry, (1999) vol. 6, issue (8), pp. 635-664.
Jordis, at al., "Synthesis of (1R,4S,5R)-endo-N,N-Dimethyl-2-azabicyclo[2.2.1]methanamine", Journal of Heterocyclic Chemistry, (1991) vol. 28, No. 8, pp. 2045-2047.
International Search Report for PCT/US2005/021870 for IM06123—6 Pages (Nov. 2, 2005).

* cited by examiner

*Primary Examiner*—Rita J Desai
*Assistant Examiner*—John Mabry
(74) *Attorney, Agent, or Firm*—Keith D. MacMillan; Thomas A. Blinka; Kenrick L. Vidale

(57) ABSTRACT

Compounds of Formula I:

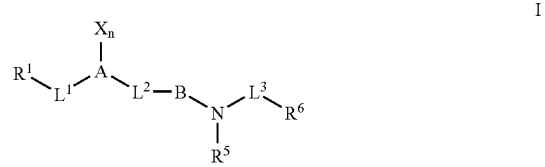

and/or pharmaceutically acceptable salts, solvates or prodrugs thereof, or pharmaceutical compositions containing such compounds exhibit anti-inflammatory and immunomodulatory activity, and can be effective in treating cancer and inflammatory, immunomodulatory or respiratory diseases or conditions.

14 Claims, No Drawings

CANNABINOID RECEPTOR LIGANDS

This application claims the benefit of U.S. Provisional Application No. 60/581,837, filed Jun. 22, 2004.

BACKGROUND

The present invention relates to compounds useful as cannabinoid receptor ligands and, more particularly, to compounds that bind to cannabinoid ($CB_2$) receptors. Compounds according to the present invention can exhibit anti-inflammatory and immunomodulatory activity and are useful in treating conditions characterized by inflammation and immunomodulatory irregularities. Examples of conditions which may be treated include, but are not limited to, rheumatoid arthritis, asthma, allergy, psoriasis, Crohn's disease, systemic lupus erythematosus, multiple sclerosis, diabetes, cancer, glaucoma, osteoporosis, renal ischemia, cerebral stroke, cerebral ischemia, and nephritis. The invention also relates to pharmaceutical compositions comprising one or more compounds according to the present invention, and methods of treating cancer, inflammation, immunomodulatory conditions, and respiratory diseases with such compounds.

Cannabinoid receptors belong to the superfamily of G-protein coupled receptors. They are classified into the predominantly neuronal $CB_1$ receptors and the predominantly peripheral $CB_2$ receptors. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with inflammation, immunomodulation and bronchial constriction such as rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (see, e.g., R. G. Pertwee, Curr. Med. Chem. 6(8), (1999), 635).

Various compounds have reportedly been developed which interact with $CB_2$ receptors and/or which have, inter alia, anti-inflammatory activity associated with cannabinoid receptors. See, e.g., U.S. Pat. Nos. 5,338,753, 5,462,960, 5,532,237, 5,925,768, 5,948,777, 5,990,170, 6,013,648 and 6,017,919.

SUMMARY OF THE INVENTION

The present invention provides a compound represented by Formula I:

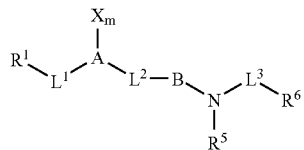

I or a pharmaceutically acceptable salt or solvate of said compound, wherein:

A is selected from the group consisting of phenyl, naphthyl, pyridyl, thiophenyl, thiazolyl, indolyl, azaindolyl, quinolyl, isoquinolyl, pyrazinyl, pyridazinyl, furanyl, pyrrolyl, pyrimidinyl, cinnolinyl, quinazolinyl, quinoxalinyl, phthalazinyl, benzofuranyl, and benzothiophenyl;

B is selected from Formulae B1-B7:

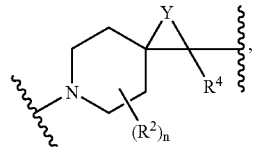

B1

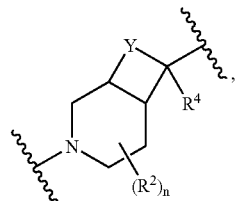

B2

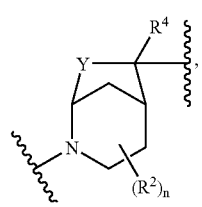

B3

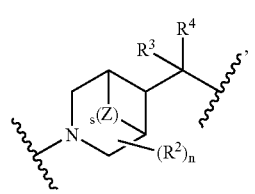

B4

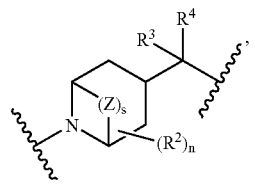

B5

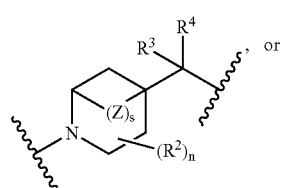

B6

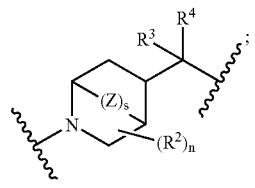

B7 each Y is independently selected from the group consisting of $-(C(R^7)_2)_p-$, $-O-(C(R^7)_2)_q-$, $-(C(R^7)_2)_q-O-$, $-S-(C(R^7)_2)_r-$, $-(C(R^7)_2)_r-S-$, $-S(O)-(C(R^7)_2)_r-$, $-(C(R^7)_2)_r-S(O)-$, $-S(O_2)-(C(R^7)_2)_r-$, $-(C(R^7)_2)_r-S(O_2)-$, $-N(R^7)-(C(R^7)_2)_r-$, and $-(C(R^7)_2)_r-N(R^7)-$;

each Z is independently selected from the group consisting of —$(C(R^7)_2)_p$—, —O—$(C(R^7)_2)_q$—, —$(C(R^7)_2)_q$—O—, —S—$(C(R^7)_2)_r$—, —$(C(R^7)_2)_r$—S—, —S(O)—$(C(R^7)_2)_r$—, —$(C(R^7)_2)_r$—S(O)—, —S(O$_2$)—$(C(R^7)_2)_r$—, —$(C(R^7)_2)_r$—SO$_2$—, —N(R$^7$)—$(C(R^7)_2)_r$—, and —$(C(R^7)_2)_r$—N(R$^7$)—;

p is an integer of from 1 to 3;

q is 1 or 2;

r is an integer of from 0 to 2;

s is 0 or 1, whereby when s is 0, Z is a covalent bond and B has a bicyclic structure;

L$^1$ is selected from the group consisting of a covalent bond, —$(C(R^7)_2)_p$—, —C(O)—, —C(O)O—, —OC(O)—, —CH(OR$^7$)—, —S(O$_2$)—, —S(O)—, —S—, —O—, —N(R$^7$)—, —C(O)N(R$^7$)—, —N(R$^7$)C(O)—, —OC(O)N(R$^7$)—, —N(R$^7$)C(O)O—, —N(R$^7$)C(O)N(R$^7$)—, —CF$_2$—, and —C(=N—OR$^7$)—;

L$^2$ is selected from the group consisting of —$(C(R^7)_2)_p$—, —C(O)—, —C(O)O—, —OC(O)—, —CH(OR$^7$)—, —S(O$_2$)—, —S(O)—, —S—, —O—, —N(R$^7$)—, —C(O)N(R$^7$)—, —N(R$^7$)C(O)—, —OC(O)N(R$^7$)—, —N(R$^7$)C(O)O—, —N(R$^7$)C(O)N(R$^7$)—, —CF$_2$—, and —C(=N—OR$^7$)—;

L$^3$ is selected from the group consisting of a covalent bond, —C(R$^7$)$_2$—, —C(O)—, —C(O)O—, —OC(O)—, —CH(OR$^7$)—, —S(O$_2$)—, —S(O)—, —S—, —O—, —N(R$^7$)—, —C(O)N(R$^7$)—, N(R$^7$)C(O)—, —CF$_2$—, and —C(=N—OR$^7$)—;

R$^1$ is selected from the group consisting of H, alkyl, —CF$_3$, —Si(alkyl)$_t$(aryl)$_{3-t}$, cycloalkyl, heterocycloalkyl, aryl and heteroaryl, wherein each of said alkyl, cycloalkyl, heterocycloalkyl, aryl and heteroaryl can be unsubstituted or independently substituted with one or more substituents which can be the same or different and are independently selected from the group consisting of halogen, —OH, alkoxy, haloalkoxy, alkyl, haloalkyl, cycloalkyl, heterocycloalkyl, aryl, heteroaryl, —N(R$^7$)$_2$, —C(O)R$^7$, —C(O)OR$^7$, —OC(O)R$^7$, —C(O)N(R$^7$)$_2$, —N(R$^7$)C(O)R$^7$, —N(R$^7$)C(O)OR$^7$, —N(R$^7$)C(O)N(R$^7$)$_2$, —NO$_2$, —CN, —S(O$_2$)R$^7$, —SO$_2$N(R$^7$)$_2$, and —N(R$^7$)C(=N—CN)NHR$^7$;

t is an integer of from 0 to 3;

R$^2$ is selected from the group consisting of H, —OH, halogen, —N(R$^7$)$_2$, alkoxy, haloalkoxy, alkyl, haloalkyl, cycloalkyl, cycloalkyloxy, heterocycloalkyl, heterocycloalkyloxy, aryl, aryloxy, heteroaryl, and heteroaryloxy, wherein each of said alkoxy, haloalkoxy, alkyl, haloalkyl, cycloalkyl, cycloalkyloxy, heterocycloalkyl, heterocycloalkyloxy, aryl, aryloxy, heteroaryl, and heteroaryloxy can be unsubstituted or independently substituted with one or more substituents which can be the same or different and are independently selected from the group consisting of halogen, —OH, alkoxy, haloalkoxy, alkyl, haloalkyl, cycloalkyl, cycloalkyl, heterocycloalkyl, aryl, heteroaryl, —N(R$^7$)$_2$, —C(O)R$^7$, —C(O)OR$^7$, —OC(O)R$^7$, —C(O)N(R$^7$)$_2$,—N(R$^7$)C(O)R$^7$, —N(R$^7$)C(O)OR$^7$, —N(R$^7$)C(O)N(R$^7$)$_2$, —NO$_2$, —CN, —S(O$_2$)R$^7$, —S(O$_2$)N(R$^7$)$_2$, and —N(R$^7$)C(=N—CN)NHR$^7$;

n is an integer of from 0 to 4;

R$^3$ and R$^4$ are the same or different, and are independently H or alkyl, wherein said alkyl can be unsubstituted or independently substituted with one or more substituents which can be the same or different and are independently selected from the group consisting of halogen, —OH, alkoxy, haloalkoxy, alkyl, haloalkyl, alkoxy, cycloalkyl, cycloalkyloxy, heterocycloalkyl, heterocycloalkyloxy, aryl, aryloxy, heteroaryl, heteroaryloxy, —N(R$^7$)$_2$, —C(O)R$^7$, —C(O)OR$^7$, —OC(O)R$^7$, —C(O)N(R$^7$)$_2$, —N(R$^7$)C(O)R$^7$, —N(R$^7$)C(O)OR$^7$, —NR$^7$C(O)N(R$^7$)$_2$, —NO$_2$, —CN, —SO$_2$)R$^7$, —S(O$_2$)N(R$^7$)$_2$, and —N(R$^7$)C(=N—CN)NHR$^7$; or if B is one of Formulae B4-B7, R$^3$ and R$^4$, taken together with the carbon atom to which they are shown attached in Formulae B4-B7, form a carbonyl group; or R$^3$ and R$^4$, taken together with the carbon atom to which they are shown attached in Formulae B4-B7, form a non-aromatic ring system, wherein said cycloalkyl or heterocycloalkyl ring can be unsubstituted or independently substituted with one or more substituents which can be the same or different and are independently selected from the group consisting of halogen, —OH, alkoxy, haloalkoxy, alkyl, haloalkyl, alkoxy, cycloalkyl, cycloalkyloxy, heterocycloalkyl, heterocycloalkyloxy, aryl, aryloxy, heteroaryl, heteroaryloxy, —N(R$^7$)$_2$, —C(O)R$^7$, —C(O)OR$^7$, —OC(O)R$^7$, —C(O)N(R$^7$)$_2$, —N(R$^7$)C(O)R$^7$, —N(R$^7$)C(O)OR$^7$, —NR$^7$C(O)N(R$^7$)$_2$, —NO$_2$, —CN, —S(O$_2$)R$^7$, —S(O$_2$)N(R$^7$)$_2$, and —N(R$^7$)C(=N—CN)NHR$^7$;

R5 and R$^6$ are the same or different and are each independently selected from the group consisting of H, alkyl, haloalkyl, —CF$_3$, cycloalkyl, heterocycloalkyl, aryl and heteroaryl, wherein each of said alkyl, cycloalkyl, heterocycloalkyl, aryl and heteroaryl can be unsubstituted or independently substituted with one or more substituents which can be the same or different and are independently selected from the group consisting of halogen, —OH, alkoxy, haloalkoxy, alkyl, haloalkyl, alkoxy, cycloalkyl, cycloalkyloxy, heterocycloalkyl, heterocycloalkyloxy, aryl, aryloxy, heteroaryl, heteroaryloxy, —N(R$^7$)$_2$, —C(O)R$^7$, —C(O)OR$^7$, —OC(O)R$^7$, —O(O)N(R$^7$)$_2$, —N(R$^7$)C(O) R$^7$, —N(R$^7$)C(O)OR$^7$, —N(R$^7$)C(O)N(R$^7$)$_2$, —NO$_2$, —CN, —SO$_2$)R$^7$, —S(O$_2$)N(R$^7$)$_2$, and —N(R$^7$)C(=N—CN)NHR$^7$;

each R$^7$ is independently selected from the group consisting of H, alkyl, haloalkyl, cycloalkyl, heterocycloalkyl, aryl and heteroaryl, wherein each of said alkyl, cycloalkyl, heterocycloalkyl, aryl and heteroaryl can be unsubstituted or independently substituted with one or more substituents which can be the same or different and are independently selected from the group consisting of halogen, —OH, alkoxy, haloalkoxy, alkyl, haloalkyl, alkoxy, cycloalkyl, cycloalkyloxy, heterocycloalkyl, heterocycloalkyloxy, aryl, aryloxy, heteroaryl, and heteroaryloxy;

X is independently selected from the group consisting of H, halogen, alkyl, alkoxy, alkenyl, alkenyloxy, alkynyl, alkynyloxy, cycloalkyl, cycloalkyloxy, heterocycloalkyl, heterocycloalkyloxy, aryl, aryloxy, heteroaryl, heteroaryloxy, —OH, OR$^7$, —C(O)OR$^7$, —OC(O)R$^7$—, —N(R$^7$)$_2$, —N(R$^7$)C(O)R$^7$, —N(R$^7$)C(O)OR$^7$, —NO$_2$ and —CN, wherein each of said alkyl, alkenyl, alkynyl, cycloalkyl, heterocycloalkyl, aryl and heteroaryl can be unsubstituted or independently substituted with one or more substituents which can be the same or different and are independently selected from the group consisting of halogen, —OH, alkoxy, haloalkoxy, alkyl, haloalkyl, alkoxy, cycloalkyl, cycloalkyloxy, heterocycloalkyl, heterocycloalkyloxy, aryl, aryloxy, heteroaryl, heteroaryloxy, —N(R$^7$)$_2$, —C(O)R$^7$, —C(O)OR$^7$, —OC(O)R$^7$, —C(O)N(R$^7$)$_2$, —N(R$^7$)C(O)R$^7$, —N(R$^7$)C(O)

OR⁷, —N(R⁷)C(O)N(R⁷)₂, —NO₂, —CN, —S(O₂)R⁷, —S(O₂)N(R⁷)₂, and —N(R⁷)C(=N—CN)NHR⁷; or X can be oxide when A is selected from the group consisting of pyridyl, thiophenyl, thiazolyl, indolyl, azaindolyl, quinolyl, isoquinolinyl, pyrazinyl, pyridazinyl, pyrrolyl, pyrimidinyl, cinnolinyl, quinazolinyl, quinoxalinyl, phthalazinyl, and benzothiophenyl;

—N(R⁵)—L³—R⁶ can optionally form a ring system; and m is an integer of from 0 to 4.

The compounds of the present invention can be useful as cannabinoid receptor ligands. The compounds can have anti-inflammatory activity and/or immunomodulatory activity and can be useful in the treatment of various medical conditions including, e.g., cutaneous T-cell lymphoma; rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that a compound of this invention can be useful in treating one or more of the diseases listed above.

The present invention also provides for a pharmaceutical composition comprising one or more compounds of Formula I. The pharmaceutical composition of the present invention can also optionally comprise one or more compounds of Formula I in combination with one or more pharmaceutically acceptable carriers, and/or one or more second agents which can be the same or different from each other, and are independently selected from the group consisting of disease-modifying antirheumatic drugs (DMARDS), non-steroidal anti-inflammatory drugs (NSAIDS), COX-2 inhibitors, COX-1 inhibitors, immunosuppressives, biological response modifiers (BRMs), Interferon β1a, Interferon β1b, glatiramer acetate, and other anti-inflammatory agents.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

In one embodiment, the present invention provides compounds of Formula I, or a pharmaceutically acceptable salt or solvate thereof, wherein the various moieties of Formula I are as described above.

In another embodiment of the compound of Formula I, A is represented by one of Formulae A1-A5, below:

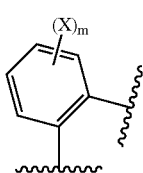
A1

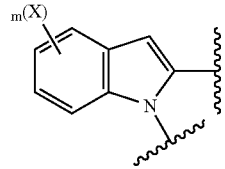
A2

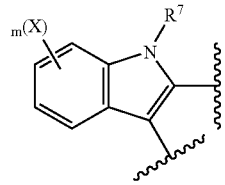
A3

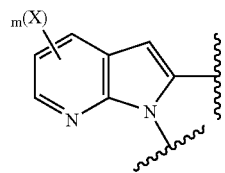
A4

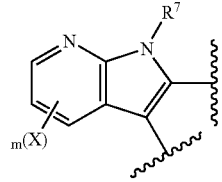
A5

In an additional embodiment of the compound of Formula I, A is represented by Formula A1.

In an additional embodiment of the compound of Formula I, A is represented by Formula A2.

In an additional embodiment of the compound of Formula I, A is represented by Formula A3.

In an additional embodiment of the compound of Formula I, A is represented by Formula A4.

In an additional embodiment of the compound of Formula I, A is represented by Formula A5.

In another embodiment of the compound of Formula I, B is represented by one of Formulae B1-B3.

In another embodiment of the compound of Formula I, B is represented by Formula B1.

In another embodiment of the compound of Formula I, B is represented by one of Formulae B4-B7.

In another embodiment of the compound of Formula I, B is represented by Formula B4.

In another embodiment of the compound of Formula I, B is represented by Formula B5.

In another embodiment of the compound of Formula I, L¹ is —C(R⁷)₂—, —C(O)—, —S(O)—, —C(O)O— or —S(O₂)—.

In another embodiment of the compound of Formula I, L² is —C(R⁷)₂—, —C(O)—, —S(O)— or —S(O₂)—.

In another embodiment of the compound of Formula I, L³ is —C(O)—, —C(R⁷)₂—, or —S(O₂)—.

In another embodiment of the compound of Formula I, R¹ is selected from the group consisting of alkyl, cycloalkyl, heterocycloalkyl, aryl and heteroaryl, wherein each of said alkyl, cycloalkyl, heterocycloalkyl, aryl and heteroaryl can be unsubstituted or independently substituted with one or more substituents which can be the same or different and are independently selected from the group consisting of halogen, substituted or unsubstituted alkyl, substituted or unsubstituted cycloalkyl, substituted or unsubstituted heterocycloalkyl, substituted or unsubstituted aryl, substituted or unsubstituted heteroaryl, —N($R^7$)$_2$, —CN, ($C_1$-$C_6$)alkoxy, and —OH.

In another embodiment of the compound of Formula I, $R^2$ is H, —OH, halogen, —N($R^7$)$_2$, $CF_3$, alkoxy, alkyl, ($C_1$-$C_6$)haloalkyl, ($C_3$-$C_5$)cycloalkyl or —CH$_2$—($C_3$-$C_5$)cycloalkyl.

In another embodiment of the compound of Formula I, $R^3$ and $R^4$ are the same or different, and are independently H or ($C_1$-$C_6$)alkyl.

In another embodiment of the compound of Formula I, $R^5$ is H or ($C_1$-$C_6$)alkyl.

In another embodiment of the compound of Formula I, $R^6$ is H, ($C_1$-$C_6$)alkyl, ($C_3$-$C_5$)cycloalkyl, or haloalkyl.

In another embodiment of the compound of Formula I, $R^7$ is H or ($C_1$-$C_6$)alkyl.

In another embodiment of the compound of Formula I, $R^8$ is H or ($C_1$-$C_6$)alkyl.

In another embodiment of the compound of Formula I, X is independently selected from the group consisting of H, halogen, alkyl, haloalkyl, ($C_3$-$C_5$)cycloalkyl, —OH, alkoxy, haloalkoxy and —CN.

In an additional embodiment of the compound of Formula I, B is represented by Formula B1, Y is —(C($R^7$)$_2$)$_p$—, and p is an integer of from 1 to 3.

In an additional embodiment of the compound of Formula I, B is represented by Formula B1 and Y is —CH$_2$—.

In an additional embodiment of the compound of Formula I, B is represented by Formula B4 and s=0.

In an additional embodiment of the compound of Formula I, B is represented by Formula B5, s=2, and Z is —CH$_2$—.

In an additional embodiment of the compound of Formula I, A is represented by one of Formulae A1 to A5 and B is represented by one of Formulae B1 to B3.

In an additional embodiment of the compound of Formula I, A is represented by one of Formulae A1 to A5 and B is represented by one of Formulae B4 to B7.

In an additional embodiment of the compound of Formula I, $L^1$, $L^2$, and $L^3$ are each independently —S(O$_2$)— or —CH$_2$—.

In an additional embodiment of the compound of Formula I, $R^1$ is selected from the group consisting of fluorophenyl, pyridyl, trifluoromethoxyphenyl, and methoxyphenyl.

In an additional embodiment of the compound of Formula I, $R^2$ is H.

In an additional embodiment of the compound of Formula I, $R^3$ and $R^4$ are H.

In an additional embodiment of the compound of Formula I, $R^3$ and $R^4$, together with the carbon to which they are bonded, form a carbonyl group.

In an additional embodiment of the compound of Formula I, $R^5$ is H.

In an additional embodiment of the compound of Formula I, $R^6$ is selected from the group consisting of —CH$_3$, —CF$_3$, and cyclopropyl.

In an additional embodiment of the compound of Formula I, m=1 and X is selected from the group consisting of H, —CH$_3$, 2-propyl, F, Cl, Br, —CF$_3$, —OCH$_3$, and —OCF$_3$.

In yet an additional embodiment of the compound of Formula I, the compounds of the present invention are represented by Formulae II to XIX:

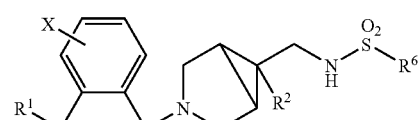

II

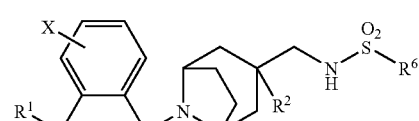

III

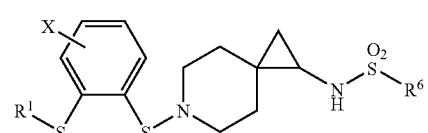

IV

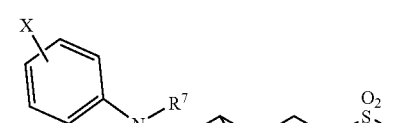

V

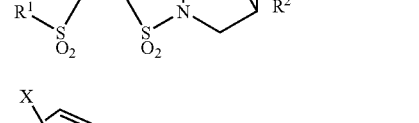

VI

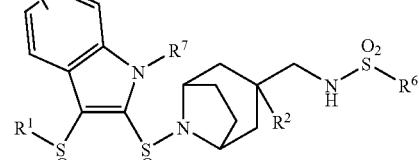

VII

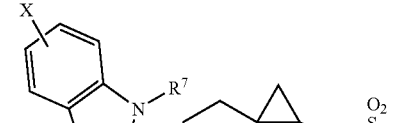

VIII

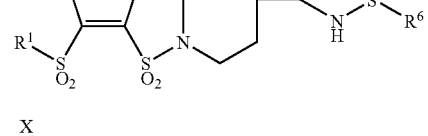

IX

-continued

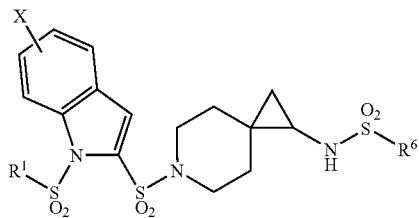
X

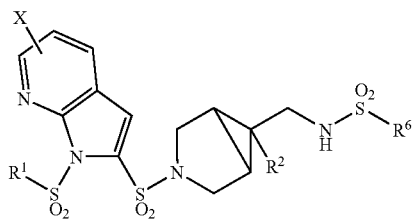
XI

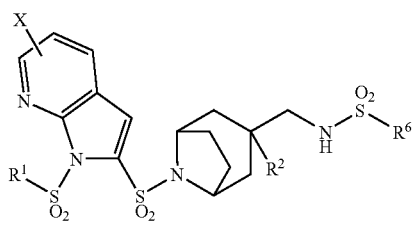
XII

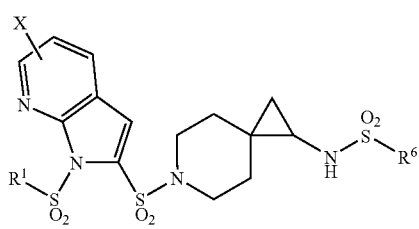
XIII

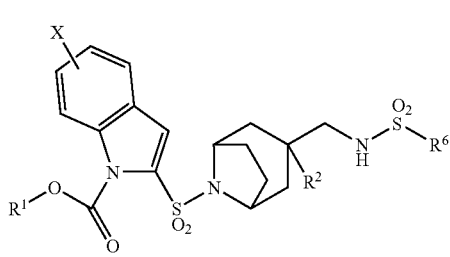
XIV

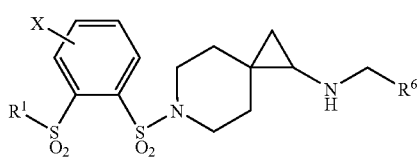
XV

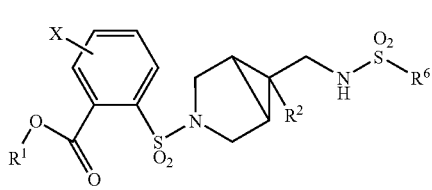
XVI

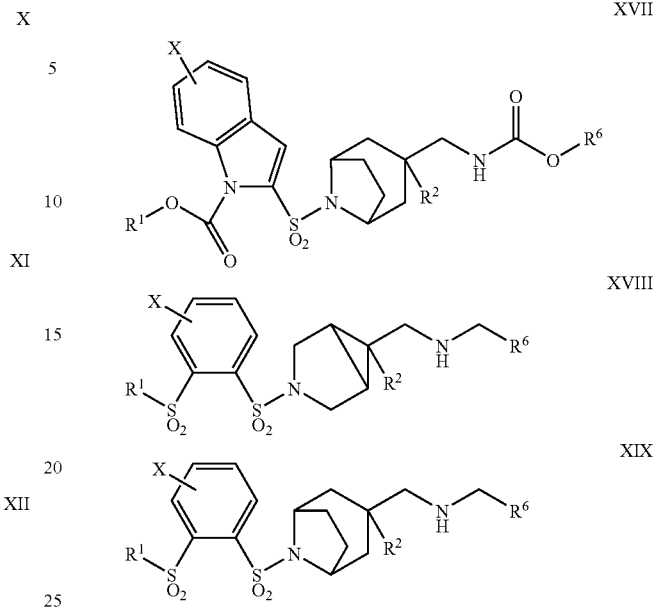

wherein in Formulae II-XIX, X is selected from the group consisting of H, F, Cl, Br, —CH$_3$, —CF$_3$, —OCH$_3$, —OCF$_3$, —OH, and —CN;

R$^1$ is selected from the group consisting of 2-fluorophenyl, 2-pyridyl, 4-methoxyphenyl, and 4-trifluoromethoxyphenyl;

R$^2$ is H or ethyl; and

R$^6$ is selected from the group consisting of methyl, trifluoromethyl, and cyclopropyl.

In yet a further embodiment, the present invention provides a pharmaceutical composition comprising one or more compounds of Formula I, in combination with one or more pharmaceutically acceptable carriers.

In yet a further embodiment, the present invention provides a pharmaceutical composition comprising one or more compounds of Formula I, in combination with one or more second agents, and one or more pharmaceutically acceptable carriers.

In yet a further embodiment, the present invention provides for methods of treating cancer, inflammatory diseases, immunomodulatory diseases, and/or respiratory diseases with one or more compounds according to Formula I.

The following definitions are used herein or are otherwise known to a skilled artisan. Except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, for example, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (multiple terms that are combined to identify a single moiety) to a subject structure is through the last named term of the multiple term. For example, a cycloalkylalkyl substituent would attach to a parent structure through the latter "alkyl" portion of the substituent (e.g., cycloalkyl-alkyl-parent structure).

"Patient" includes both human and animals.

"Mammal" means humans and other mammalian animals.

"Alkyl" means a monovalent aliphatic hydrocarbon group or radical which may be considered to be formed by the loss of a hydrogen from an alkane. An alkyl group may be linear or branched and may comprise from about 1 to about 20 carbon atoms in the chain. Preferred alkyl groups comprise from about 1 to about 12 carbon atoms in the chain. More preferred alkyl groups comprise from about 1 to about 6 carbon atoms in the chain.

The term "branched" in reference to an alkyl group means that one or more lower alkyl groups such as methyl, ethyl or propyl, are attached to a linear alkyl chain.

"Lower alkyl" means an alkyl group having about 1 to about 6 carbon atoms in the chain. "Lower alkyl" groups may be linear or branched.

The term "substituted alkyl" means that the alkyl group may be substituted by one or more substituents, each of which may be the same or different, and each substituent may be independently selected from the group consisting of halogen, alkyl, alkenyl, alkynyl, haloalkyl, —OH, haloalkoxy, alkoxy, cycloalkyl, cycloalkyloxy, heterocycloalkyl, heterocycloalkyloxy, aryl, aryloxy, heteroaryl, heteroaryloxy, —N($R^7$)$_2$, —C(O)$R^7$, —C(O)O$R^7$, —OC(O)$R^7$, —C(O)N($R^7$)$_2$, —N($R^7$)C(O)$R^7$, —N($R^7$)C(O)O$R^7$, —N($R^7$)C(O)N($R^7$)$_2$, —NO$_2$, —CN, —S(O$_2$)$R^7$, —S(O$_2$)N($R^7$)$_2$, and —N($R^7$)C(=N—CN)NH$R^7$, where "$R^7$" is defined as indicated above. Non-limiting examples of suitable alkyl groups include methyl, ethyl, n-propyl, isopropyl and t-butyl.

"Alkenyl" means an aliphatic unsaturated hydrocarbon group or radical having at least one carbon-carbon double bond, which may be considered to be formed by the loss of a hydrogen from an alkene. An alkenyl group may be linear or branched and may comprise from 2 to about 15 carbon atoms in the chain. Preferred alkenyl groups have 2 to about 12 carbon atoms in the chain, and more preferably 2 to about 6 carbon atoms in the chain.

The term "branched" in reference to an alkenyl group means that one or more lower alkyl groups such as methyl, ethyl or propyl, are attached to an alkenyl chain.

"Alkynyl" means a non-aromatic hydrocarbon group or radical having at least one carbon-carbon triple bond, which may be considered to be formed by the loss of a hydrogen from an alkyne. An alkynyl group may be linear or branched and may comprise from 2 to about 15 carbon atoms in the chain. Preferred alkynyl groups have from 2 to about 12 carbon atoms in the chain, and more preferably from 2 to about 4 carbon atoms in the chain.

The term "branched" in reference to an alkynyl group means that one or more lower alkyl groups such as methyl, ethyl or propyl, are attached to a linear alkynyl chain.

"Aryl" means an aromatic monocyclic or multicyclic group, which may be considered to be formed by removing a hydrogen from an aromatic monocyclic or multicyclic hydrocarbon. An aryl group may comprise from about 6 to about 14 carbon atoms in the ring or rings, preferably from about 6 to about 10 carbon atoms. The aryl group may optionally be substituted with one or more "ring system substituents" which may be the same or different, and are as defined below. Non-limiting examples of suitable aryl groups include phenyl and naphthyl.

"Ring system" means an aromatic, partially unsaturated, or fully saturated ring, in which all of the ring atoms are carbon, or one or more of the ring atoms are elements other than carbon, such as nitrogen, oxygen and sulfur. A ring system may comprise from 3 to about 14 ring atoms, preferably about 5 to about 10 ring atoms, more preferably about 5 to about 6 ring atoms. A ring system may optionally be substituted with one or more "ring system substituents" which may be the same or different. A ring system may include cycloalkyl, heterocycloalkyl, aryl, or heteroaryl rings, as defined herein, as well as partially unsaturated cycloalkyl or heterocycloalkyl rings (e.g., cyclohexenyl, thiazolinyl, etc.).

"Non-aromatic ring system" means any ring system as defined above, but excluding aryl or heteroaryl rings.

"Heteroaryl" means an aromatic monocyclic or multicyclic ring system, which may be considered to be formed by independently removing and/or replacing one or more of the carbon atoms in an aromatic hydrocarbon ring with one or more elements other than carbon, such as nitrogen, oxygen and sulfur. A heteroaryl group may comprise about 5 to about 14 ring atoms, preferably about 5 to about 10 ring atoms, more preferably about 5 to about 6 ring atoms. A heteroaryl group may optionally be substituted with one or more "ring system substituents" which may be the same or different, and are as defined below. The prefix "aza", "oxa" or "thia" before the heteroaryl root name means that at least one ring atom is nitrogen, oxygen or sulfur, respectively. A nitrogen atom of a heteroaryl can be optionally oxidized to the corresponding N-oxide. Non-limiting examples of suitable heteroaryl groups include pyridyl, pyrazinyl, furanyl, thiophenyl, pyrimidinyl, isoxazolyl, isothiazolyl, oxazolyl, thiazolyl, pyrazolyl, furazanyl, pyrrolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofuranyl, indolyl, azaindolyl, benzimidazolyl, benzothiophenyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, pyridazinyl, pyrimidyl, cinnolinyl and the like.

It should also be noted that tautomeric forms such as, for example, the moieties:

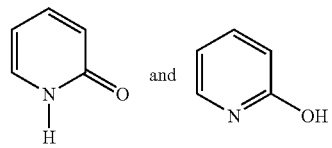

are considered equivalent in certain embodiments of this invention.

"Cycloalkyl" means a non-aromatic (i.e., aliphatic) mono- or multicyclic ring system comprising from about 3 to about 10 carbon atoms in the ring or rings, preferably from about 5 to about 10 carbon atoms. Preferred cycloalkyl rings comprise from about 5 to about 7 ring atoms. The cycloalkyl can be optionally substituted with one or more "ring system substituents" which may be the same or different, and are as defined below. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocycloalkyl" means a non-aromatic monocyclic or multicyclic ring system comprising 3 to about 10 ring atoms, preferably about 5 to about 10 ring atoms, in which one or more of the atoms in the ring system is an element other than carbon, for example nitrogen, oxygen or sulfur. If more than one ring atom is an element other than carbon, the non-carbon ring atoms may be the same or different. However, heterocycloalkyl does not include ring systems having adjacent oxygen and/or sulfur atoms present in the ring system. Preferred heterocycloalkyl ring systems comprise from about 5 to about 6 ring atoms. The prefix "aza", "oxa" or "thia" before the heterocycloalkyl root name means that at least one of the ring atoms is respectively a nitrogen, oxygen or sulfur atom. Any —NH— in a heterocycloalkyl ring may be present in protected form such as, for example, as an —N(Boc)-, —N(CBz)-, —N(Tos)- group and the like; such protected —NH— groups are also considered part of this invention. The heterocycloalkyl may optionally be substituted by one or more "ring system substituents" which may be the same or different, and are as defined above. The nitrogen or sulfur atom of the heterocycloalkyl may optionally be oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

It should be noted that in heteroatom containing ring systems of this invention, there are no hydroxyl groups on carbon atoms adjacent to a N, O or S. In addition, there are no N or S groups on carbon adjacent to another heteroatom. Thus, for example, in the ring:

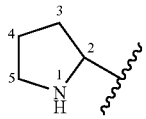

there is no —OH attached directly to carbons marked 2 and 5, and none of the ring atoms at positions 2 and 5 may be heteroatoms.

"Cycloalkyloxy" means a cycloalkyl group, as defined above, bonded to the parent moiety through an ether oxygen. A non-limiting example of a suitable cycloalkyloxy group is cyclohexyloxy:

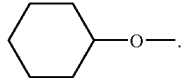

Similarly, heterocycloalkyloxy means a heterocycloalkyl group, as defined above, bonded to the parent moiety through an ether oxygen.

"Halogen" or "halo" means fluorine, chlorine, bromine, or iodine. Preferred halogens are fluorine, chlorine or bromine, more preferably fluorine and chlorine.

"Ring system substituent" means a substituent attached to an aromatic or non-aromatic ring system, and which may be considered, for example, to replace an available hydrogen on the ring system. A ring system may be substituted with one or more ring system substituents. If the ring system is substituted with two or more ring system substituents, the ring system substituents may be the same or different, and each may independently be selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocycloalkyl, —C(=N—CN)—NH$_2$, —C(=NH)—NH$_2$, —C(=NH)—NH(alkyl), L$_1$L$_2$N—, L$_1$L$_2$N-alkyl-, L$_1$L$_2$NC(O)—, L$_1$L$_2$NSO$_2$— and —SO$_2$NL$_1$L$_2$, wherein L$_1$ and L$_2$ may be the same or different and independently are selected from the group consisting of hydrogen, alkyl, aryl, cycloalkyl, and aralkyl. "Ring system substituent" may also include a single moiety, which may be considered to simultaneously replace two hydrogens on two adjacent carbon atoms (one hydrogen on each carbon) on a ring system. Examples of such a moiety include methylenedioxy, ethylenedioxy, —C(CH$_3$)$_2$— and the like, which are attached to rings to form structures such as, for example:

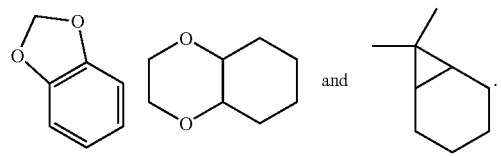

"Aralkyl" or "arylalkyl" means an aryl-alkyl- group in which the aryl and alkyl are as previously described. Preferred arylalkyls comprise a lower alkyl group substituted with at least one aryl group. Non-limiting examples of suitable arylalkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise an aryl group substituted with at least one lower alkyl group. A non-limiting example of a suitable alkylaryl group is tolyl. The bond to the parent moiety is through the aryl.

"Heteroaralkyl" or "heteroarylalkyl" means a heteroaryl-alkyl- group in which the heteroaryl and alkyl are as described above. Preferred heteroarylalkyl groups comprise a lower alkyl group. Non-limiting examples of suitable arylalkyl groups include pyridylmethyl, and quinolin-3-ylmethyl. The heteroarylalkyl group is bonded to the parent moiety through the alkyl portion of the heteroarylalkyl group.

"Heteroarylalkenyl" means a heteroaryl-alkenyl- group in which the heteroaryl and alkenyl are as described above. The heteroaryl group is bonded to the parent moiety through the alkenyl portion of the heteroarylalkenyl group.

"Heteroarylalkynyl" means a heteroaryl-alkynyl- group in which the heteroaryl and alkynyl are as described above. The heteroaryl group is bonded to the parent moiety through the alkynyl portion of the heteroarylalkynyl group.

"Alkylheteroaryl" means an alkyl-heteroaryl- group in which the alkyl and heteroaryl are as described above. A non-limiting example of an alkylheteroaryl group is methylpyridinyl. The alkyl group is bonded to the parent moiety through the heteroaryl portion of the alkylheteroaryl group.

"Hydroxyalkyl" means a HO-alkyl- group in which alkyl is as defined above. Preferred hydroxyalkyl groups comprise a lower alkyl group. Non-limiting examples of suitable hydroxyalkyl groups include hydroxymethyl and 2-hydroxyethyl.

"Acyl" means a H—C(O)—, alkyl-C(O)— or cycloalkyl-C(O)— group in which the alkyl and cycloalkyl groups are as previously described. Acyl groups are bonded to the parent moiety through the carbonyl. Preferred acyl groups comprise a lower alkyl group. Non-limiting examples of suitable acyl groups include formyl, acetyl and propanoyl.

"Aroyl" means an aryl-C(O)— group in which the aryl group is as previously described. Aroyl groups are bonded to the parent moiety through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. Alkoxy groups are bonded to the parent moiety through the ether oxygen.

"Aryloxy" means an aryl-O— group in which the aryl group is as previously described. Non-limiting examples of suitable aryloxy groups include phenoxy and naphthoxy. Aryloxy groups are bonded to the parent moiety through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. Aralkyloxy groups are bonded to the parent moiety through the ether oxygen.

"Alkylthio" means an alkyl-S— group in which the alkyl group is as previously described. Non-limiting examples of suitable alkylthio groups include methylthio and ethylthio. Alkylthio groups are bonded to the parent moiety through the sulfur.

"Arylthio" means an aryl-S— group in which the aryl group is as previously described. Non-limiting examples of suitable arylthio groups include phenylthio and naphthylthio. Arylthio groups are bonded to the parent moiety through the sulfur.

"Aralkylthio" means an aralkyl-S— group in which the aralkyl group is as previously described. Non-limiting example of a suitable aralkylthio group is benzylthio. Aralkylthio groups are bonded to the parent moiety through the sulfur.

"Alkoxycarbonyl" means an alkyl-O—C(O)— group. Non-limiting examples of suitable alkoxycarbonyl groups include methoxycarbonyl and ethoxycarbonyl. Alkoxycarbonyl groups are bonded to the parent moiety through the carbonyl.

"Aryloxycarbonyl" means an aryl-O—C(O)— group. Non-limiting examples of suitable aryloxycarbonyl groups include phenoxycarbonyl and naphthoxycarbonyl. Aryloxycarbonyl groups are bonded to the parent moiety through the carbonyl.

"Aralkoxycarbonyl" means an aralkyl-O—C(O)— group. A non-limiting example of a suitable aralkoxycarbonyl group is benzyloxycarbonyl. Aralkoxycarbonyl groups are bonded to the parent moiety through the carbonyl.

"Alkylsulfonyl" means an alkyl-S($O_2$)— group. Preferred alkylsulfonyl groups are those in which the alkyl group comprises a lower alkyl. Alkylsulfonyl groups are bonded to the parent moiety through the sulfonyl.

"Arylsulfonyl" means an aryl-S($O_2$)— group. Arylsulfonyl groups are bonded to the parent moiety through the sulfonyl.

"Halogenated alkyl" or "haloalkyl" means an alkyl group in which at least one hydrogen is replaced with a halogen.

"Heteroalkyl" means a linear or branched alkyl chain comprising from 1 to 12 carbon atoms in which at least one carbon atom of the chain is replaced with a heteroatom independently selected from the group consisting of nitrogen, oxygen, or sulfur.

The term azaindolyl refers to indolyl groups in which one of the carbons of the benzene ring is replaced with a nitrogen, for example as shown by the non-limiting examples below:

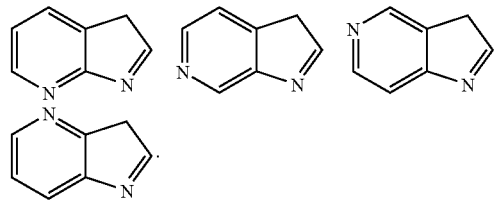

The term azaindolyl also includes tautomeric forms, for example as shown by the non-limiting examples below:

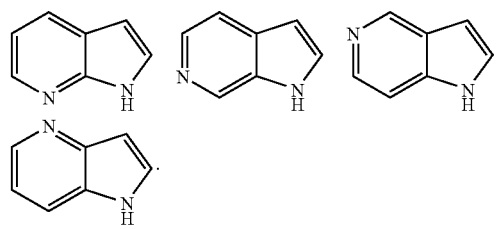

When the stereochemistry is not explicitly indicated in a structure, the structure includes all stereochemical configurations having the indicated connectivity (e.g., all possible enantiomers), as well as mixtures of such stereoisomers (e.g., racemic mixtures). For example,

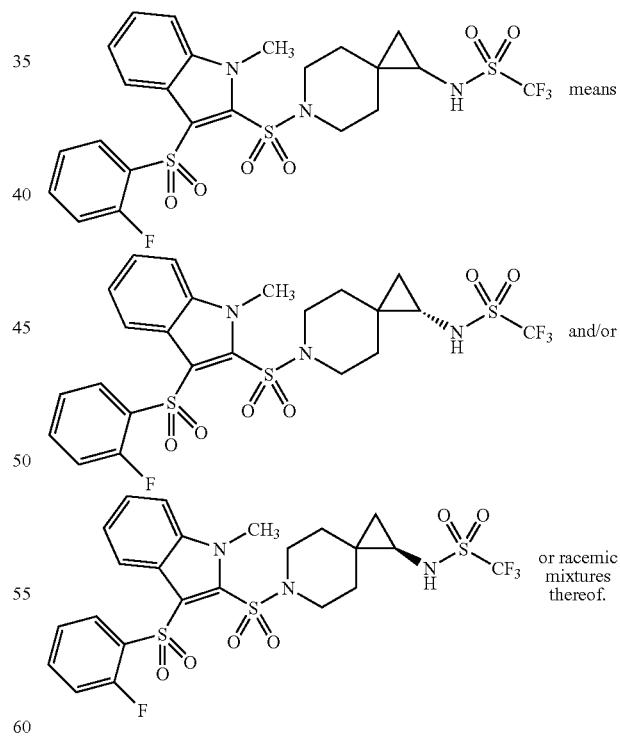

The term "substituted" means that one or more hydrogens bonded to the designated atom or group is replaced with a selection from the indicated group, provided that the normal valency of the designated atom or group under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means that substitution with the specified groups, radicals or moieties is permitted, but not required.

It should also be noted that any heteroatom with unsatisfied valences in the text, schemes, examples and Tables herein is assumed to have sufficient hydrogen atoms to satisfy the valences.

When a functional group in a compound is termed "protected", this means that the group is present in modified form to preclude undesired side reactions at the protected site when the compound is subjected to particular reaction conditions. Suitable protecting groups will be recognized by those with ordinary skill in the art as well as by reference to standard textbooks such as, for example, T. W. Greene et al, *Protective Groups in Organic Synthesis* (1991), Wiley, N.Y., herein incorporated by reference in its entirety.

When any variable (e.g., aryl, heterocycle, $R^7$, etc.) occurs more than one time in any constituent or in a formula, its definition on each occurrence is independent of its definition at every other occurrence, unless otherwise specified.

As used herein, the term "composition" is intended to encompass a product comprising a combination of any specified ingredients in any specified amounts, as well as any product formed, directly or indirectly, from the combination of any specified ingredients in any specified amounts.

Prodrugs and solvates of the compounds of the present invention are also contemplated herein. The term "prodrug", as employed herein, denotes a compound that is a drug precursor that upon administration to a patient, undergoes chemical conversion by metabolic or chemical processes to yield a compound of Formula I of the present invention, or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means the physical association of a compound of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Reference herein to compounds according to Formula I of the present invention is understood to include reference to prodrugs and solvates thereof, unless otherwise indicated.

"Effective amount" or "therapeutically effective amount" is meant to denote an amount of a compound or a composition of the present invention that is effective in modulating (e.g., inhibiting, activating, or binding to) $CB_2$ receptors and thus producing the desired therapeutic, ameliorative, inhibitory or preventative effect.

The compounds of the present invention (e.g., compounds according to Formulae II-XIX such as the compounds exemplified in Table 1, below) can form salts that are also within the scope of this invention. The term "salt" or "salts", as employed herein, denotes acidic salts formed with inorganic and/or organic acids, as well as basic salts formed with inorganic and/or organic bases. In addition, when a compound of Formula I of the present invention comprises both a basic moiety, such as but not limited to a pyridinyl, indolyl, or imidazolyl, and an acidic moiety, such as but not limited to a carboxylic acid, zwitterions ("inner salts") may be formed and are included within the term "salt" or "salts" as used herein. Pharmaceutically acceptable (i.e., non-toxic, physiologically acceptable) salts are preferred, although other salts are also useful.

Salts of the compounds of Formula I the present invention may be formed, for example, by reacting a compound of Formula I with a suitable amount of acid or base, such as an equivalent amount, in a suitable medium, such as one in which the salt precipitates or in an aqueous medium followed by lyophilization.

Reference herein to compounds according to Formula I of the present invention is understood to include reference to salts thereof, unless otherwise indicated.

Exemplary acid addition salts (i.e., salts formed by the addition of a suitable acid to the compound according to Formula I of the present invention) include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (i.e., tosylates) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1)1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website), which are incorporated herein by reference in their entirety.

Exemplary basic salts (i.e., salts formed by the addition of a suitable base to the compound according to Formula I of the present invention) include ammonium salts, alkali metal salts such as sodium, lithium, and potassium salts, alkaline earth metal salts such as calcium and magnesium salts, salts of organic bases (for example, organic amines) such as dicyclohexylamines, t-butyl amines, and salts of amino acids such as arginine, lysine and the like. Basic salts may also include salts formed by quarternizing basic nitrogen-containing groups of compounds according to Formula I of the present invention with alkylating agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the present invention and all acid and base salts are considered equivalent to the free forms of the corresponding compounds for purposes of the present invention.

The compounds of Formula I, and salts, solvates and prodrugs thereof, may exist in their tautomeric form (for example, as an amide or imino ether). All such tautomeric forms are contemplated herein as part of the present invention.

All isomers (for example, stereoisomers, geometric isomers, optical isomers and the like) of the compounds of Formula I (including those of the salts, solvates and prodrugs of the compounds of the present invention, as well as the salts and solvates of the prodrugs of the compounds of the present invention), such as those which may exist due to the presence of asymmetric carbons on various substituents, including enantiomeric forms (which may exist even in the absence of asymmetric carbons), rotameric forms, atropisomers, and diastereomeric forms, are contemplated as falling within the scope of the present invention, as are positional isomers (such as, for example, 4-pyridyl and 3-pyridyl).

Polymorphic forms of the compounds of Formula I, and of the salts, solvates and prodrugs of the compounds of Formula I, are intended to be included in the present invention.

Individual stereoisomers of the compounds of Formula I may be, for example, substantially free of other isomers, or may comprise a mixture of two or more isomers. For example, the compounds of the present invention may be in the form of a racemic mixture, or a mixture of selected stereoisomers.

The chiral centers of the compounds of the present invention may have either an S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the compounds of the present invention.

Exemplary compounds (and/or pharmaceutically acceptable salts, solvates, or prodrugs thereof) of the present invention are set forth below in Table I, and refer to Formula I. $R^1$, $R^6$, —A—X, —B—N($R^5$)— and X are as set forth in Table I. $R^5$ is H, n=1, m=1, $L^2$ is —S($O_2$)—. For clarity, X—N($R^5$)—, $L^1$, $L^2$ and $L^3$ are also represented in the structures of moieties A and B in Table I.

TABLE I

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 1 | 2-fluorophenyl | $CF_3$ | H | $-S(O_2)-$ | $-S(O_2)-$ | 1-methyl-6-X-indole | azabicyclic-CH₂-NH-L³ | 596.1 |
| 2 | 2-fluorophenyl | $CH_3$ | H | $-S(O_2)-$ | $-S(O_2)-$ | 1-methyl-6-X-indole | azabicyclic-CH₂-NH-L³ | 542.1 |
| 3 | 2-fluorophenyl | $CF_3$ | H | $-S(O_2)-$ | $-S(O_2)-$ | 1-methyl-6-X-7-azaindole | azabicyclic-CH₂-NH-L³ | 583.1 |
| 4 | 2-fluorophenyl | $CF_3$ | H | $-S(O_2)-$ | $-S(O_2)-$ | 1-(1-ethyl)-6-X-indole | azabicyclic-CH₂-NH-L³ | 624.1 |
| 5 | 2-fluorophenyl | $CH_3$ | H | $-S(O_2)-$ | $-S(O_2)-$ | 1-(1-ethyl)-6-X-indole | azabicyclic-CH₂-NH-L³ | 570.1 |

TABLE I-continued

| Cmpd | R¹ (with linking point to L¹) | R⁶ | X | L¹ | L³ | —A—X— (with linking points to L¹, L² and X) | —B—N(R⁵)— (with linking points to L² and L³) | M + H |
|---|---|---|---|---|---|---|---|---|
| 6 | 2-pyridyl | CF₃ | Cl | —S(O₂)— | —S(O₂)— | 4-X-phenyl (L¹, L² on adjacent positions) | azabicyclic-CH₂-NH-L³ | 560.1 |
| 7 | 2-pyridyl | CH₃ | Cl | —S(O₂)— | —S(O₂)— | 4-X-phenyl | azabicyclic-CH₂-NH-L³ | 506.1 |
| 8 | 2-pyridyl | CF₃ | OCF₃ | —S(O₂)— | —S(O₂)— | 4-X-phenyl | azabicyclic-CH₂-NH-L³ | 610.1 |
| 9 | 2-fluorophenyl | CH₃ | Cl | —S(O₂)— | —S(O₂)— | 4-X-phenyl | azabicyclic-CH₂-NH-L³ | 523.1 |
| 10 | 2-pyridyl | CH₃ | H | —S(O₂)— | —S(O₂)— | 5-X-indolyl (L¹ on N, L² at 2-position) | azabicyclic-CH₂-NH-L³ | 511.1 |
| 11 | 2-fluorophenyl | CF₃ | Cl | —S(O₂)— | —S(O₂)— | 4-X-phenyl | azabicyclic-CH₂-NH-L³ | 577.1 |

TABLE I-continued

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 12 | 2-fluorophenyl (L¹ position) | CF₃ | H | —S(O₂)— | —S(O₂)— | 5-X-indole (N-L¹, 2-L²) | 3-azabicyclo[3.1.0]hexane with CH₂-NH-L³ substituent, N-L² | 582.1 |
| 13 | 2-fluorophenyl | CH₃ | H | —S(O₂)— | —S(O₂)— | 5-X-indole | 3-azabicyclo[3.1.0]hexane with CH₂-NH-L³, N-L² | 528.1 |
| 14 | 2-pyridyl | CF₃ | CN | —S(O₂)— | —S(O₂)— | 5-X-indole | 3-azabicyclo[3.1.0]hexane with CH₂-NH-L³, N-L² | 590.1 |
| 15 | 2-pyridyl | CF₃ | H | —S(O₂)— | —S(O₂)— | 5-X-indole | 3-azabicyclo[3.1.0]hexane with CH₂-NH-L³, N-L² | 565.1 |
| 16 | 2-fluorophenyl | CH₃ | Cl | —S(O₂)— | —S(O₂)— | 1,2,4-trisubstituted benzene (X, L¹, L²) | spiro[cyclopropane-piperidine] with NH-L³ (racemic mixture), N-L² | 537.04 |
| 17 | 2-fluorophenyl | CH₃ | Cl | —S(O₂)— | —S(O₂)— | 1,2,4-trisubstituted benzene (X, L¹, L²) | spiro[cyclopropane-piperidine] with NH-L³ (enantiomer A), N-L² | 537.04 |

TABLE I-continued

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 18 | 2-fluorophenyl (L¹ ortho to F) | CH₃ | Cl | —S(O₂)— | —S(O₂)— | 1,2,4-trisubstituted benzene (X para to L¹, L² ortho to L¹) | spiro[cyclopropane-1,4'-piperidine] with NH-L³ and N-L² (enantiomer B) | 537.04 |
| 19 | 2-fluorophenyl | CF₃ | Cl | —S(O₂)— | —S(O₂)— | 1,2,4-trisubstituted benzene | spiro[cyclopropane-1,4'-piperidine] (enantiomer B) | 591.0 |
| 20 | 2-fluorophenyl | CH₃ | H | —S(O₂)— | —S(O₂)— | 5-substituted indole (L¹ on N, L² at C2) | spiro[cyclopropane-1,4'-piperidine] (racemic mixture) | 542.09 |
| 21 | 2-fluorophenyl | CF₃ | H | —S(O₂)— | —S(O₂)— | 5-substituted indole | spiro[cyclopropane-1,4'-piperidine] (racemic mixture) | 596.1 |
| 22 | 2-fluorophenyl | CF₃ | H | —S(O₂)— | —S(O₂)— | 5-substituted indole | spiro[cyclopropane-1,4'-piperidine] (enantiomer B) | 596.06 |
| 23 | 2-pyridyl | CF₃ | Cl | —S(O₂)— | —S(O₂)— | 1,2,4-trisubstituted benzene | spiro[cyclopropane-1,4'-piperidine] (enantiomer B) | 574.02 |

TABLE I-continued

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 24 | 2-fluorophenyl with L¹ | CH₃ | Br | —S(O₂)— | —S(O₂)— | 5-X-indole (L¹ on N, L² at 2-position) | spiro[cyclopropane-1,4'-piperidine] with NH-L³ and N-L², racemic mixture | 620.1 |
| 25 | 2-fluorophenyl with L¹ | CF₃ | Br | —S(O₂)— | —S(O₂)— | 5-X-indole (L¹ on N, L² at 2-position) | spiro[cyclopropane-1,4'-piperidine] with NH-L³ and N-L², racemic mixture | 674.1 |
| 26 | 2-fluorophenyl with L¹ | CF₃ | Br | —S(O₂)— | —S(O₂)— | 5-X-indole (L¹ on N, L² at 2-position) | spiro[cyclopropane-1,4'-piperidine] with NH-L³ and N-L², enantiomer B | 674.1 |
| 27 | 4-(trifluoromethoxy)phenyl with L¹ | CF₃ | Cl | —S(O₂)— | —S(O₂)— | phenyl with L¹, L² and X | spiro[cyclopropane-1,4'-piperidine] with NH-L³ and N-L², enantiomer B | 657.0 |
| 28 | 4-methoxyphenyl with L¹ | CF₃ | Cl | —S(O₂)— | —S(O₂)— | phenyl with L¹, L² and X | spiro[cyclopropane-1,4'-piperidine] with NH-L³ and N-L², enantiomer B | 603.03 |

TABLE 1-continued

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 29 | 2-F-phenyl (L¹ ortho to F) | CF₃ | CF₃ | —S(O₂)— | —S(O₂)— | phenyl with L¹, L² ortho, X para | spiro[2.5]octane cyclopropylamine-piperidine, enantiomer B | 625.04 |
| 30 | 4-(F₃CO)-phenyl | CF₃ | CF₃ | —S(O₂)— | —S(O₂)— | phenyl with L¹, L² ortho, X para | spiro[2.5]octane cyclopropylamine-piperidine, enantiomer B | 691.03 |
| 31 | 2-pyridyl | CF₃ | CF₃ | —S(O₂)— | —S(O₂)— | phenyl with L¹, L² ortho, X para | spiro[2.5]octane cyclopropylamine-piperidine, enantiomer B | 608.04 |
| 32 | 2-F-phenyl | CF₃ | OCF₃ | —S(O₂)— | —S(O₂)— | phenyl with L¹, L² ortho, X para | spiro[2.5]octane cyclopropylamine-piperidine, enantiomer B | 641.03 |
| 33 | 2-pyridyl | CF₃ | OCH₃ | —S(O₂)— | —S(O₂)— | phenyl with L¹, L² ortho, X para | spiro[2.5]octane cyclopropylamine-piperidine, enantiomer B | 570.07 |

TABLE 1-continued
| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 34 | 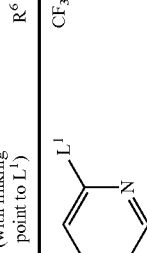 | CF₃ | H | —S(O₂)— | —S(O₂)— | 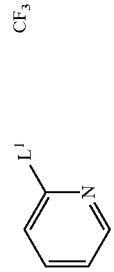 | <br>enantiomer B | 562.04 |
| 35 |  | CF₃ | F | —S(O₂)— | —S(O₂)— | 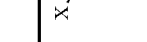 | <br>enantiomer B | 580.03 |
| 36 |  | CH₃ | Cl | —S(O₂)— | —S(O₂)— |  | 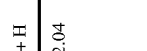<br>enantiomer B | 542.06 |
| 37 |  |  | Cl | —S(O₂)— | —S(O₂)— |  | <br>enantiomer B | 546.1 |
| 38 |  | CF₃ | OH | —S(O₂)— | —S(O₂)— |  | <br>enantiomer B | 556.04 |

TABLE I-continued
| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 39 | 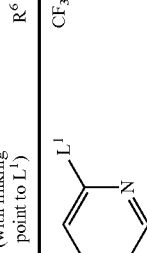 | CF₃ | OCF₃ | —S(O₂)— | —CH₂— | 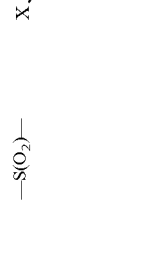 | 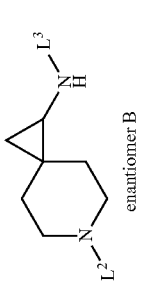 enantiomer B | 574.09 |
| 40 | 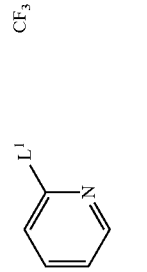 | CF₃ | OCF₃ | —S(O₂)— | —S(O₂)— | 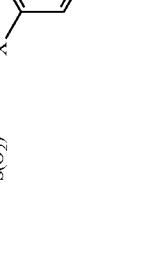 | 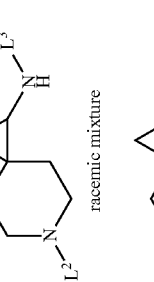 enantiomer B | 624.04 |
| 41 | 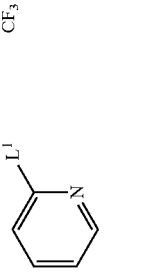 | CF₃ | H | —S(O₂)— | —S(O₂)— | 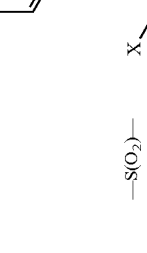 | 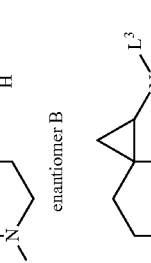 enantiomer B | 579.06 |
| 42 | 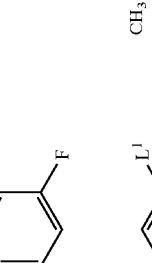 | CF₃ | H | —S(O₂)— | —S(O₂)— | 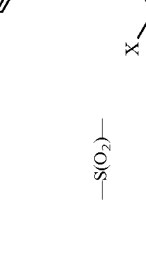 |  racemic mixture | 597.1 |
| 43 | 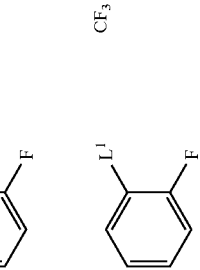 | CH₃ | H | —S(O₂)— | —S(O₂)— | 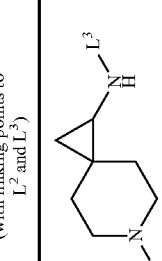 |  enantiomer B | 543.1 |
| 44 | 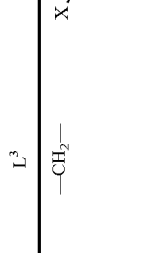 | CF₃ | H | —S(O₂)— | —S(O₂)— | 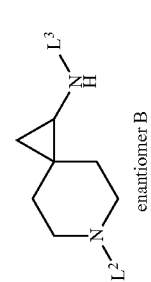 |  racemic mixture | 610.1 |

TABLE I-continued

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 45 | 2-fluorophenyl (L¹ ortho to F) | CH₃ | H | —S(O₂)— | —S(O₂)— | 6-X-1-methyl-indole (L¹ at 3, L² at 2) | 1-L²-spiro[cyclopropane-1,4'-piperidine] with NHL³ (racemic mixture) | 556.1 |
| 46 | 2-fluorophenyl | CF₃ | H | —S(O₂)— | —S(O₂)— | 5-X-indole (L¹ at N, L² at 2) | tropane-type bicyclic amine with CH₂-NHL³ | 610.1 |
| 47 | 2-fluorophenyl | CH₃ | H | —S(O₂)— | —S(O₂)— | 5-X-indole | tropane-type bicyclic amine with CH₂-NHL³ | 556.1 |
| 48 | 2-pyridyl | CF₃ | H | —S(O₂)— | —S(O₂)— | 5-X-indole | tropane-type bicyclic amine with CH₂-NHL³ | 593.1 |
| 49 | 2-pyridyl | CH₃ | H | —S(O₂)— | —S(O₂)— | 5-X-indole | tropane-type bicyclic amine with CH₂-NHL³ | 539.1 |

TABLE I-continued

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 50 | 2-pyridyl | CF₃ | Cl | —S(O₂)— | —S(O₂)— | 1,2,4-trisubstituted phenyl | quinuclidine-CH₂-NH- | 588.1 |
| 51 | 2-pyridyl | CH₃ | Cl | —S(O₂)— | —S(O₂)— | 1,2,4-trisubstituted phenyl | quinuclidine-CH₂-NH- | 534.1 |
| 52 | 2-fluorophenyl | CH₃ | H | —S(O₂)— | —S(O₂)— | N-methylindole | quinuclidine-CH₂-NH- | 570.1 |
| 53 | 2-fluorophenyl | CF₃ | H | —S(O₂)— | —S(O₂)— | N-methylindole | quinuclidine-CH₂-NH- | 624.2 |
| 54 | 2-fluorophenyl | CF₃ | H | —S(O₂)— | —S(O₂)— | indole | quinuclidine-C(CH₃)(CH₂NH)- | 638.2 |

TABLE I-continued
| Cmpd | R¹ (with linking point to L¹) | R⁶ | X | L¹ | L³ | —A—X (with linking points to L¹, L² and X) | —B—N(R⁵)— (with linking points to L² and L³) | M + H |
|---|---|---|---|---|---|---|---|---|
| 55 | t-Bu-L¹ | t-Bu | H | —OC(O)— | —C(O)O— | 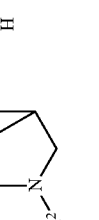 | 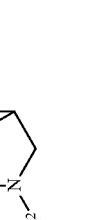 | 520.1 |
| 56 | 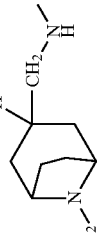 | CF₃ | Cl | —S(O₂)— | —CH₂— |  |  | 510.1 |
| 57 | t-Bu-L¹ | CF₃ | Cl | —OC(O)— | —S(O₂)— |  |  | 519.1 |
| 58 |  | CF₃ | Cl | —S(O₂)— | —CH₂— |  |  | 566.1 |
| 59 |  | CF₃ | Cl | —S(O₂)— | —S(O₂)— | | | 616 |

TABLE 1-continued

| Cmpd | R¹ (with linking point to L¹) | R⁶ | X | L¹ | L³ | —A—X (with linking points to L¹, L² and X) | —B—N(R⁵) (with linking points to L² and L³) | M + H |
|---|---|---|---|---|---|---|---|---|
| 60 | 2-fluorophenyl (L¹ ortho to F) | CF₃ | H | —S(O₂)— | —S(O₂)— | 5-X-7-azaindole, N-L¹, 3-L² | 2-azabicyclo[2.2.1] system with CH₂-NH-L³, N-L² | |
| 61 | 2-fluorophenyl | CF₃ | H | —S(O₂)— | —S(O₂)— | 6-X-indole with N-CH₃, 2-L², 3-L¹ | spiro[cyclopropane-piperidine] with NH-L³, N-L², enantiomer | |
| 62 | 2-fluorophenyl | t-Bu | H | —S(O₂)— | —C(O)O— | 6-X-indole with N-CH(CH₃)₂, 2-L², 3-L¹ | bicyclic CH₂-NH-L³, N-L² | |

The present invention includes all isomers (e.g., enantiomers) of the compounds listed above, as well as mixtures of isomers (e.g., racemic mixtures). Mixtures of isomers may be prepared, for example, from isomeric mixtures of starting materials, or by reaction conditions in which isomeric products are produced. Specific isomers may be prepared, for example, from isomerically pure starting materials, or by isolation of specific isomers from isomeric mixtures using known methods (e.g., chromatography using a chiral stationary phase).

One aspect of the present invention relates to pharmaceutical compositions comprising one or more compounds of the present invention (and/or a pharmaceutically acceptable salt, solvate, or prodrug thereof) in a pharmaceutically acceptable carrier. The pharmaceutical composition of the present invention may also optionally comprise one or more other therapeutic agents.

The compounds of the present invention can be useful as cannabinoid receptor ligands. Therefore, another aspect of the present invention relates to a method of modulating (inhibiting or activating) a cannabinoid $CB_2$ receptor in a patient, which comprises administering to a patient a $CB_2$ receptor-modulating amount of one or more of the compounds of the present invention.

The compounds of the present invention can have anti-inflammatory activity and/or immunomodulatory activity and can be useful in treating cancer, inflammatory diseases, immunomodulatory diseases, or respiratory diseases. For example, one or more compounds according to Formula I may be useful in treating various medical conditions including cutaneous T-cell lymphoma, rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that a compound of this invention may be useful in treating one or more of the diseases listed.

Additionally, a compound of the present invention may be co-administered or used in combination with a second agent, for example disease-modifying antirheumatic drugs (DMARDS) such as methotrexate, azathioprine, leflunomide, pencillinamine, gold salts, mycophenolate mofetil, cyclophosphamide and other similar drugs. They can also be co-administered with or used in combination with one or more non-steroidal anti-inflammatory drugs (NSAIDS) such as piroxicam, naproxen, indomethacin, ibuprofen and the like; COX-2 selective inhibitors such as rofecoxib, which is available as Vioxx® (from Merck & Company, Whitehouse Station, N.J.) and celecoxib, which is available as Celebrex® (from Pfizer Inc., New York, N.Y.); COX-1 inhibitors such as Piroxicam, which is available as Feldene® (from Pfizer Inc., New York, N.Y.); immunosuppressives such as steroids, cyclosporine, Tacrolimus, rapamycin, methotrexate and the like; biological response modifiers (BRMs) such as etanercept, which is available as Enbrel® (from Wyeth-Ayerst, Philadelphia, Pa.), infliximab, which is available as Remicade® (from Centocor, Inc., Malvern, Pa.), IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide, which is available as Thalomid® (Celgene Corporation, Warren, N.J.) and other small molecule inhibitors of pro-inflammatory cytokine production. Other drugs that the compounds of the invention can be co-administered or used in combination with include Anaprox® (i.e., naproxen sodium), Arava® (i.e., leflunomide), Arthrotec® (i.e., combination of diclofenac and misoprostol), Azulfidine® (i.e., sulfasalazine), Aspirin® (i.e., acetylsalicylic acide), Cataflam® (i.e., diclofenac), Celestone® Soluspan® (i.e., betamethasone acetate and betamethasone sodium phosphate), Clinoril® (i.e., sulindac), Cortone Acetate® (i.e., cortisone acetate), Cuprimine® (i.e., penicillamine), Daypro® (i.e., oxaprozin), Decadron® (i.e., dexamethasone), Depen® (i.e., penicillamine), Depo-Medrol® (i.e., methylprednisolone acetate), Disalcid® (i.e., salsalate), Dolobid® (i.e., diflunisal), Naprosyn® (i.e., naproxen), Gengraf® (i.e., cyclosporine), Hydrocortone® (i.e., hydrocortisone), Imuran® (i.e., azathioprine), Indocin® (i.e., indomethacin), Lodine® (i.e., etodolac), Motrin® (i.e., ibuprofin), Myochrysine® (i.e., gold sodium thiomalate), Nalfon® (i.e., fenoprofen calcium), Naprelan® (i.e., naproxen sodium), Neoral® (i.e., cyclosporine), Orudis® (i.e., ketoprofen), Oruvail® (i.e., ketoprofen), Pediapred® (i.e., prednisolone), Plaquenil® (i.e., hydroxychloroquine), Prelone® (i.e., prednisolone), Relafen® (i.e., nabumetone), Solu-Medrol® (i.e., methylprednisolone sodium succinate), Tolectin® (i.e., tolmetin sodium), Trilisate® (i.e., choline magnesium trisalicylate) and Volataren® (i.e., diclofenac). These include any formulation of the above named drugs.

Also additionally, a compound of the present invention may be co-administered or used in combination with an H1 antagonist for the treatment of seasonal allergic rhinitis and/or asthma. Suitable H1 antagonists may be, for example, Claritin® (i.e., loratadine), Clarinex® (i.e., desloratadine), Allegra® (i.e., fexofenadine hydrochloride), or Zyrtec® (i.e., cetirizine hydrochloride).

In another aspect, the invention provides a method for treating rheumatoid arthritis comprising administering a compound of the present invention in combination with compound selected from the class consisting of a COX-2 inhibitor e.g. Celebrex® or Vioxx®; a COX-1 inhibitor e.g. Feldene® (i.e., piroxicam); an immunosuppressive e.g. methotrexate or cyclosporin; a steroid e.g. β-methasone; an anti-TNF-α compound, e.g. Enbrel® or Remicade®; a PDE IV inhibitor, and other classes of compounds indicated for the treatment of rheumatoid arthritis.

In addition, the present invention provides a pharmaceutical composition for treating rheumatoid arthritis comprising a therapeutically effective amount of a compound of the present invention in combination with a compound selected from the class consisting of a COX-2 inhibitor, a COX-1 inhibitor, an immunosuppressive, a steroid, an anti-TNF-α compound and other classes of compounds indicated for the treatment of rheumatoid arthritis, and a pharmaceutically acceptable carrier.

In a further aspect, the invention provides a method for treating multiple sclerosis comprising administering a compound of the present invention in combination with a compound selected from the group consisting of Avonex® (i.e., interferon β-1a), Betaseron® (i.e., Interferon β-1b), Copaxone® (i.e., glatiramer acetate) or other compounds indicated for the treatment of multiple sclerosis.

In addition, the invention also provides a pharmaceutical composition for treating multiple sclerosis comprising a therapeutically effective amount of a compound of the present invention in combination with a compound selected from the group consisting of Avonex®, Betaseron®, Copaxone® or other compounds indicated for the treatment of multiple sclerosis, and a pharmaceutically acceptable carrier.

In yet another aspect, the invention provides a method for treating psoriasis comprising administering a compound of the present invention in combination with a compound selected from the group consisting of an immunosuppressive, a steroid and an anti-TNF-α compound. In one aspect, the immunosuppressive is methotrexate, leflunomide, sulfasalazine or cyclosporin, the steroid is β-methasone and the anti-TNF-α compound is Enbrel® or Remicade®.

Furthermore, the present invention relates to a pharmaceutical composition for treating psoriasis including an effective amount of a compound of the present invention in combination with a compound selected from an immunosuppressive (e.g., methotrexate, leflunomide or cyclosporin), a steroid (e.g., β-methasone) and an anti-TNF-α compound (e.g., Enbrel® or Remicade®), and a pharmaceutically acceptable carrier.

As described above, the present invention provides a pharmaceutical composition comprising one or more compounds of the present invention and a pharmaceutically acceptable carrier. The compounds of the present invention can be administered in any conventional dosage form known to those skilled in the art. Pharmaceutical compositions comprising the compounds of the present invention (e.g., one or more compounds according to Formulae II-XIX, and/or a pharmaceutically acceptable salt, solvate, or prodrug thereof, optionally in combination with one or more pharmaceutically acceptable carriers, excipients, additives, etc.) can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

All routes of administration are contemplated including, but not limited to, parenteral, transdermal, subcutaneous, intramuscular, sublingual, inhalation, rectal and topical. Thus, appropriate unit forms of administration include oral forms such as tablets, capsules, powders, cachets, granules and solutions or suspensions, sublingual and buccal forms of administration, aerosols, implants, subcutaneous, intramuscular, intravenous, intranasal, intraocular, subcutaneous or rectal forms of administration.

When a solid composition is prepared in the form of tablets, e.g., a wetting agent such as sodium lauryl sulfate can be added to micronized or non-micronized compounds of the present invention and mixed with a pharmaceutical vehicle such as silica, gelatin starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active principle continuously or at predetermined intervals, e.g., by using ionic resins and the like.

A preparation in the form of gelatin capsules may be obtained, e.g., by mixing one or more compounds of the present invention with a diluent, such as a glycol or a glycerol ester, and incorporating the resulting mixture into soft or hard gelatin capsules.

A preparation in the form of a syrup or elixir may comprise one or more compounds of the present invention in combination with other ingredients, e.g., with a sweetener, methylparaben and propylparaben as antiseptics, flavoring agents and an appropriate color.

Water-dispersible powders or granules may comprise one or more compounds of the present invention mixed with, e.g., dispersants, wetting agents or suspending agents, such as polyvinylpyrrolidone, as well as with sweeteners and/or other flavoring agents.

Suppositories for rectal administration may comprise one or more compounds of the present invention in combination with, e.g., binders that melt at the rectal temperature, for example cocoa butter or polyethylene glycols.

Parenteral, intranasal or intraocular administration may be provided by, e.g., aqueous suspensions, isotonic saline solutions or sterile and injectable solutions comprising one or more compounds of the present invention and pharmacologically compatible dispersants and/or solubilizers, for example, propylene glycol or polyethylene glycol.

Thus, to prepare an aqueous solution for intravenous injection of one or more compounds of the present invention, it is possible to use a co-solvent, e.g., an alcohol such as ethanol or a glycol such as polyethylene glycol or propylene glycol, and a hydrophilic surfactant such as Tween® 80. An oily solution injectable intramuscularly can be prepared, e.g., by solubilizing one or more compounds of the present invention with a triglyceride or a glycerol ester.

Topical administration can be provided by incorporating one or more compounds of the present invention in, e.g., creams, ointments or gels.

Transdermal administration can be provided by using patches in the form of a multilaminate, or with a reservoir, comprising one or more compounds of the present invention and an appropriate solvent.

Administration by inhalation can be provided by, e.g., an aerosol comprising one or more compounds of the present invention and sorbitan trioleate or oleic acid, for example, together with trichlorofluoromethane, dichlorofluoromethane, dichlorotetrafluoroethane or any other biologically compatible propellant gas. Alternatively, the inhalation system may comprise one or more compounds of the present invention, optionally associated with an excipient, in powder form.

Compounds of the present invention can also be formulated in microcapsules or microspheres, e.g., liposomes, optionally with one or more carriers or additives.

For treatment of chronic conditions, one or more compounds of the present invention may be administered from implants that provide prolonged release of the compounds of the present invention. Compositions comprising compounds of the present invention may also be prepared in the form of an oily suspension or in the form of a suspension of microspheres in an isotonic medium.

The daily dose of a compound of the present invention for modulating a cannabinoid $CB_2$ receptor in a patient and/or for treatment of a disease or condition cited above, is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2-4 divided doses. The exact dose, however, is determined by the attending clinician and is dependent on the potency of the compound administered, the age, weight, condition and response of the patient.

Compounds of the present invention can be used in combination with disease modifying antirheumatic agents, H1 antagonists, compounds useful in the treatment of multiple sclerosis, and/or compounds useful in the treatment of psoriasis, as described above. The administration and dosage of such agents is as according to the schedule listed in the product information sheet of the approved agents, in the Physicians Desk Reference (PDR) as well as therapeutic protocols well known in the art.

It will be apparent to those skilled in the art that the administration of other active agents used in combination with the compounds of the present invention can be varied depending on the disease being treated and the known effects of the agents on that disease. Also, in accordance with the knowledge of the skilled clinician, the therapeutic protocols (e.g. dosage amounts and times of administration) can be varied in view of the observed effects of the administered agents on the patients, and in view of the observed responses of the disease to the administered agents.

EXAMPLES

The following examples illustrate the preparation of some of the compounds of the invention and are not to be construed as limiting the invention disclosed herein. Alternate mechanistic pathways and analogous structures will be apparent to those skilled in the art.

The following abbreviations are used in the procedures and schemes: aqueous (aq.), anhydrous (anhyd), n-butyl (n-Bu), n-butyllithium (n-BuLi), concentrated (conc.), days (d), 1-(3-dimethylaminopropyl)-3-ethylcarbodiimide hydrochloride (EDCl), dimethylformamide (DMF), ethanol (EtOH), ethyl (Et), ethyl acetate (EtOAc), hours (h), leaving group (LG), hydroxybenzotriazole (HOBT), meta-chloroperoxybenzoic acid (MCPBA), lithium diisopropylamide (LDA), methanesulfonyl chloride (MsCl), methanol (MeOH), minutes (min), methyl (Me), methyllithium (MeLi), molar (moles per liter, M), N-chlorosuccinimide (NCS), N,N-dimethylaminopyridine (DMAP), normal (N), pounds per square inch (psi), preparative thin layer chromatography (PTLC), room temperature (rt), saturated sodium chloride solution (brine), silica gel chromatography (sgc), 2-(tert-butoxycarbonyloxyimino)-2-phenylacetonitrile (BOC-ON), tert-butoxycarbonyl (BOC), trifluoroacetic anhydride (TFAA), trifluoroacetic acid (TFA), trifluoromethanesulfonic anhydride ($Tf_2O$), 2,2,2-trichloroethyl carbamate (Troc) and tetrahydrofuran (THF). In a typical work-up procedure, the reaction mixture is diluted with a suitable solvent, such as EtOAc, $Et_2O$, or $CH_2Cl_2$, and washed successively with appropriate acidic, basic, or neutral aqueous solutions. The organic solution is separated, dried over an appropriate drying agent such as $MgSO_4$ or $Na_2SO_4$, filtered, and the solvent removed by evaporation.

General Scheme 1

Compounds according to Formula I, in which moiety A has structure A1, moiety $L^2$ is —$S(O_2)$—, moiety $L^1$ is —$S(O_2)$—, —C(O)—, or —$CH_2$—, and moiety B has structure B1, B2, or B3, may be prepared by the general method shown in General Scheme 1, below.

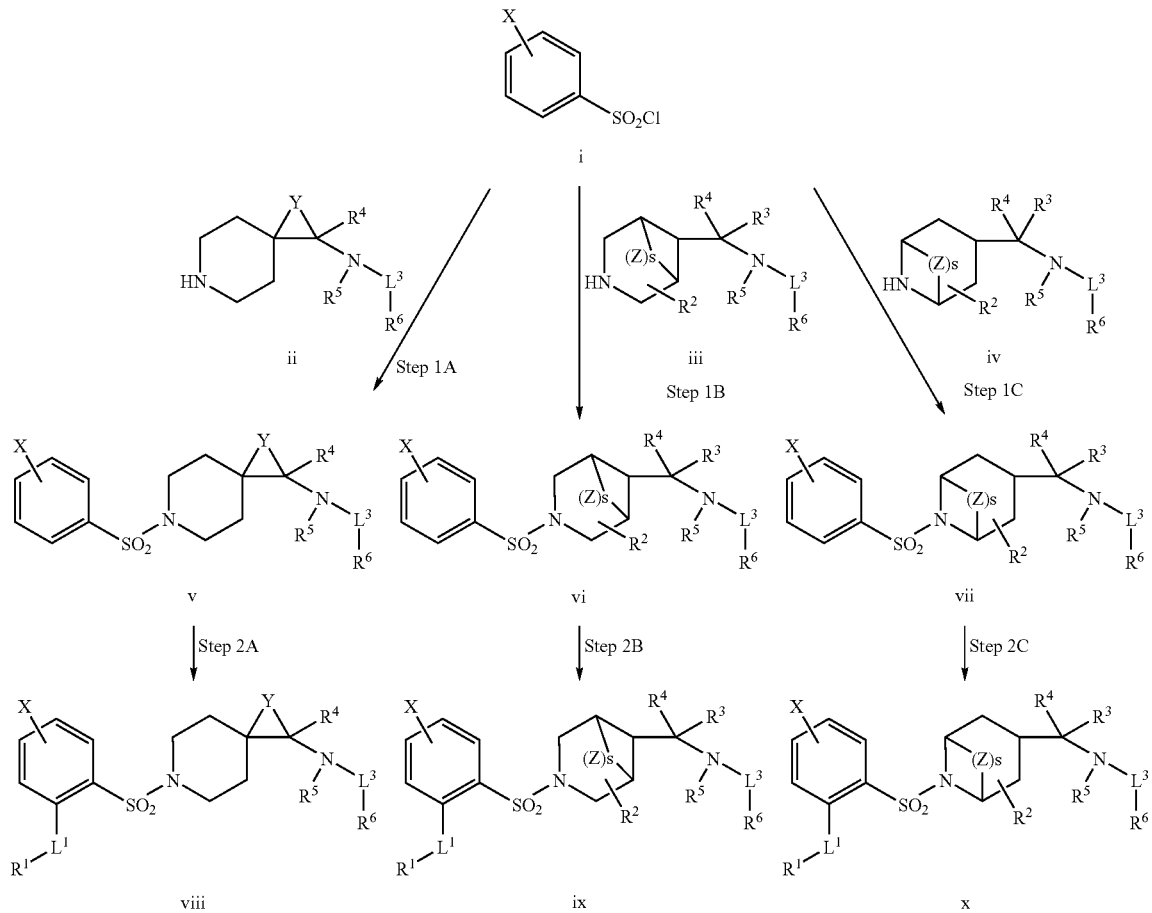

GENERAL SCHEME 1

For A = A1; $L^2$ = $SO_2$; $L^1$ = $SO_2$, CO, $CH_2$; B = B1, B2, B3

Description of General Scheme 1

In Steps 1A, 1B, and 1C, cyclic amines of formulae ii, iii, and iv, respectively, are reacted with a suitable base such as triethyl amine or diisopropylethyl amine in an organic solvent such as methylene chloride or dichloroethane. An aryl sulfonyl chloride of the formula i is then added to give the corresponding sulfonamides v, vi, and vii. The reaction may be carried out at low temperatures, e.g., at temperatures ranging from −15° C. to 0° C.

In Steps 2A, 2B, and 2C, compounds of the formulae v, vi, and vii may be dissolved in a suitable solvent such as THF or DME, and then are reacted with a suitable base such as n-BuLi, at a low temperature, e.g., temperatures ranging from −110° C. to −78° C. The resulting anion may be treated with a suitable electrophile such as an alkyl chloride (e.g., to provide a product in which $L^1$ is —$CH_2$—), an acid chloride (e.g., to provide a product in which $L^1$ is —C(O)—), an aldehyde (e.g., to provide a product in which $L^1$ is —$CH_2$—), a sulfonyl fluoride (e.g., to provide a product in which $L^1$ is —$S(O_2)$—), or a disulfide (e.g., to provide a product in which $L^1$ is —$S(O_2)$—) to give products vi ii, ix, and x.

The desired functional group $L^3$ may be introduced into the product by the selection of the appropriate cyclic amine of formulae ii, iii, or iv having the desired functionality at $L^3$. Methods for preparing such cyclic amines would be readily apparent to those skilled in the art. Alternatively, the desired —$L^3R^6$ moiety can be provided by replacing the —$L^3R^6$ moiety in viii, ix, or x can be replaced with a different, desired —$L^3R^6$ moiety using well known deprotection procedures.

General Scheme 1A

Alternatively, compounds viii, ix, and x may be prepared by other methods, for example according to General Scheme 1A, below.

GENERAL SCHEME 1A

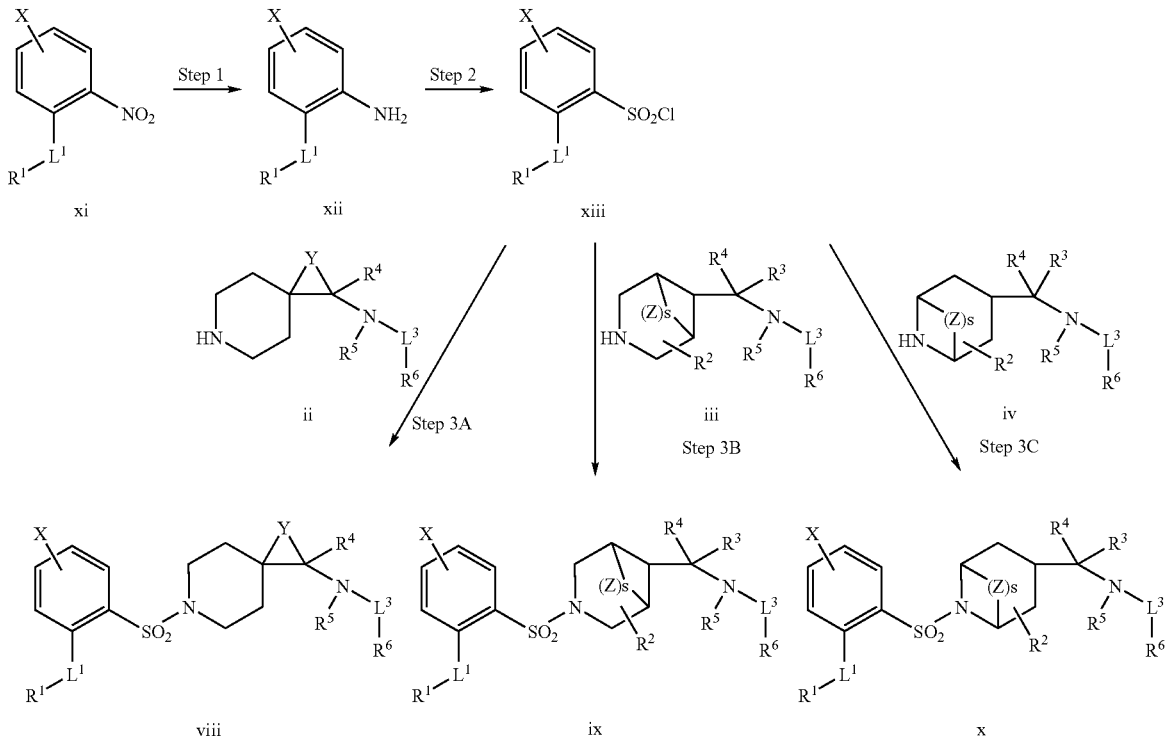

For A = A1; $L^2$ = —$S(O_2)$—; $L^1$ = —$S(O_2)$—, —C(O)—, —$CH_2$—; B = B1, B2, B3

Description of General Scheme 1A

In Step 1, nitro compound xi is reduced with a reducing agent, e.g., $SnCl_2$ or Zn, in an alcoholic solvent containing an acid (e.g., HCl) to form amino compound xii. In Step 2, the amino compound xii may be dissolved in a mixture of acids (e.g., a 1:1 mixture of acetic acid and HCl), and is then cooled (e.g., to 0° C.). Aqueous $NaNO_2$ may then be slowly added to the cooled solution. The resulting solution is stirred for 0.5-1 h and then poured into cooled acetic acid solution saturated with $SO_2$ gas in the presence of CuCl, to give sulfonyl chloride xiii.

In Steps 3A, 3B, and 3C, amines of the formulae ii, iii, and iv, respectively, are reacted with a base such as triethyl amine or diisopropylethyl amine in an organic solvent such as methylene chloride or dichloroethane. The aryl sulfonyl chloride of formula xiii is then added (e.g., at temperatures ranging from −15° C. to 0° C.) to give the corresponding sulfonamides viii, ix, and x.

The desired functional group $L^1$ may be introduced into the product by the preparation of the appropriate nitro compound xi having the desired functionality at $L^1$. Methods for preparing such nitro compounds would be readily apparent to those skilled in the art.

$L^1$ is $-S(O_2)-$, $-C(O)-$, or $-CH_2-$, moiety $L^2$ is $-SO_2-$, and moiety B has the structure B1, B2, or B3, may be prepared by the general method shown in General Scheme 2, below.

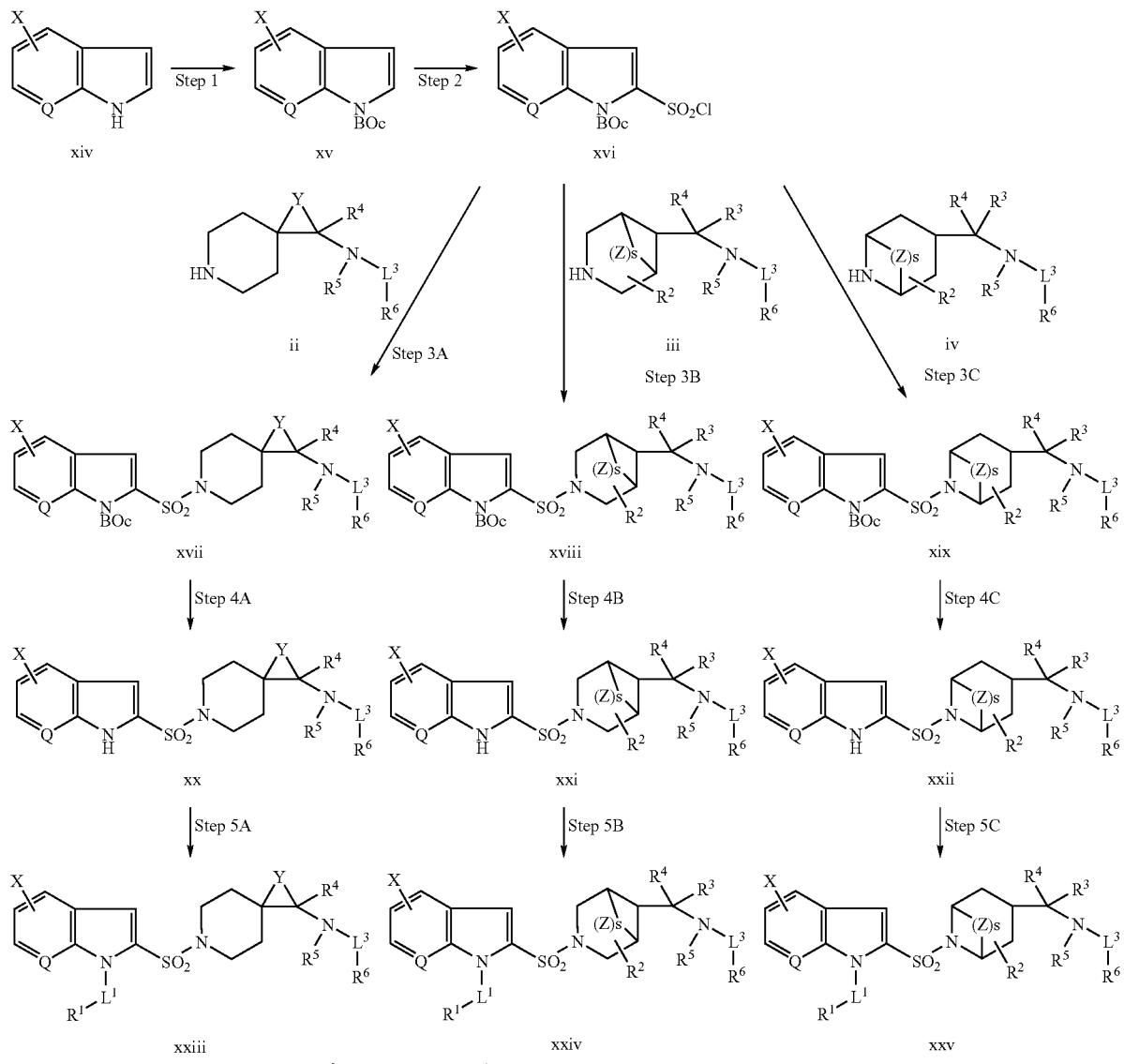

GENERAL SCHEME 2

For A = A2, A4; Q is CH—, or = N—; $L^2$ = —S(O_2)—; $L^1$ = —S(O_2)—, —C(O)—, —CH_2—; B = B1, B2, B3

The desired functional group $L^3$ may be introduced into the product by the selection of the appropriate cyclic amine of formulae ii, iii, or iv having the desired functionality at $L^3$. Methods for preparing such cyclic amines would be readily apparent to those skilled in the art. Alternatively, the desired $-L^3R^6$ moiety can be provided by replacing the $-L^3R^6$ moiety in viii, ix, or x can be replaced with a different, desired $-L^3R^6$ moiety using well known deprotection procedures.

General Scheme 2

Compounds according to Formula I, in which moiety A has structure A2 or A4 (wherein Q is =CH— or =N—), moiety Description of General Scheme 2

In Step 1, $(Boc)_2O$ is dissolved in a suitable inert solvent such as THF, methylene chloride, or dichloromethane, and reacted with a compound of the formula xiv to give compound xv.

In Step 2, compound xv is dissolved in a solvent such as THF or DME, and then reacted with a base such as n-BuLi (e.g., at a reaction temperature range of −110° C. to −78° C.). The resulting anion is exposed to $SO_2$ gas for a period of 1-2 h and then allowed to warm to room temperature. The solvent is removed and the residue is redissolved in a solvent such as methylene chloride or dichloroethane, and is then treated with N-chlorosuccinimide to give sulfonyl chloride xvi.

In Steps 3A, 3B, and 3C, amines of the formulae ii, iii, and iv, respectively, are reacted with a base such as triethyl amine or diisopropylethyl amine in an organic solvent such as methylene chloride or dichloroethane. The sulfonyl chloride xvi is then added (e.g., at reaction temperatures of, e.g., −15° C. to 0° C.) to give the corresponding N-Boc protected sulfonamides xvii, xviii, and xix.

In Steps 4A, 4B, and 4C, the N-Boc protected sulfonamides xvii, xviii, and xix are dissolved in a solvent such as dioxane or THF, and then treated with a base such as LiOH to give the corresponding deprotected derivatives xx, xxi, and xxii, respectively.

In Steps 5A, 5B, and 5C, compounds xx, xxi, and xxii are dissolved in solvents such as DMF or DMSO and are then sequentially treated with a base such as $CsCO_3$ and then with suitable electrophiles such as an alkyl or aryl sulfonyl chloride (e.g., to provide a product in which $L^1$ is —S($O_2$)—), an alkyl or aryl acid chloride (e.g., to provide a product in which $L^1$ is —C(O)—), or an alkyl halide (e.g., to provide a product in which $L^1$ is —$CH_2$—) to give products xxiii, xxiv, and xxv.

The desired functional group $L^3$ may be introduced into the product by the selection of the appropriate cyclic amine of formulae ii, iii, or iv having the desired functionality at $L^3$. Methods for preparing such cyclic amines would be readily apparent to those skilled in the art. Alternatively, the desired —$L^3R^6$ moiety can be provided by replacing the —$L^3R^6$ moiety in viii, ix, or x can be replaced with a different, desired —$L^3R^6$ moiety using well known deprotection procedures.

General Scheme 2A

Alternatively, compounds xxiii, xxiv, and xxv may be prepared by other methods, for example according to General Scheme 2A, below.

GENERAL SCHEME 2A

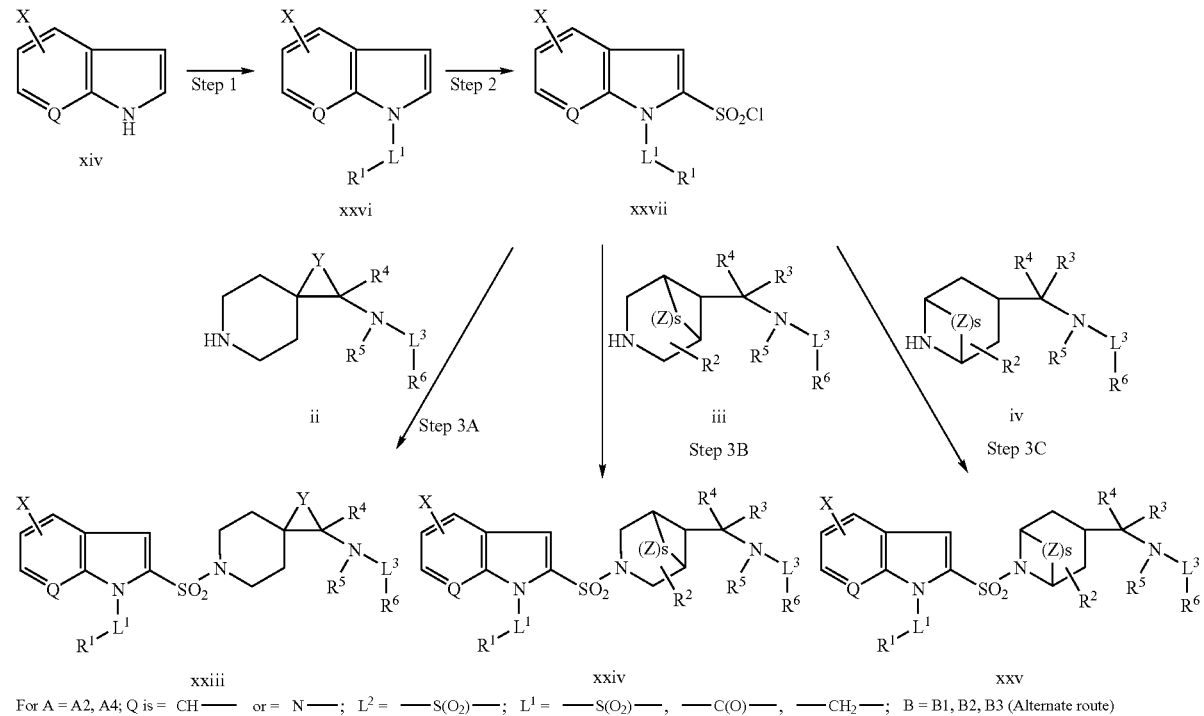

For A = A2, A4; Q is= CH—— or = N——; $L^2$ = —S($O_2$)—; $L^1$ = —S($O_2$)—, —C(O)—, —$CH_2$—; B = B1, B2, B3 (Alternate route)

Description of General Scheme 2A

In Step 1, indole (or azaindole) derivative xiv is dissolved in a solvent such as toluene, benzene, or xylene, and then treated with an aqueous base such as NaOH or KOH and a catalytic amount of a phase transfer catalyst such as Aliquat® (i.e., methyltricaprylyl ammonium chloride) or benzyltriethylammonium bromide. The resulting solution is then treated with a suitable electrophile represented by the formula $R^1L^1$—LG, wherein LG represents a leaving group such as chloride, bromide, fluoride or mesylate, to give compound xxvi. By appropriate selection of electrophile, the desired group $L^1$ (e.g., —S($O_2$)—, —C(O)—, —$CH_2$—, etc.) can be introduced.

In Step 2, compound xxvi is dissolved in a solvent such as THF or DME and then reacted with a base such as n-BuLi (e.g., at a reaction temperature range of −110° C. to −78° C. The resulting anion is then exposed to $SO_2$ gas for a period of 1-2 h and allowed to warm to room temperature. The solvent is removed and the residue is redissolved in solvent such as methylene chloride or dichloroethane and then treated with N-chlorosuccinimide to give sulfonyl chloride xxvii.

In Steps 3A, 3B, and 3C, amines of the formulae ii, iii, and iv, respectively, are mixed with a base such as triethyl amine or diisopropylethyl amine in an organic solvent such as methylene chloride or dichloroethane. Sulfonyl chloride xxvii is then added to give the corresponding sulfonamides xxiii, xxiv, and xxv (e.g., at reaction temperatures ranging from −15° C. to 0° C.).

The desired functional group $L^3$ may be introduced into the product by the selection of the appropriate cyclic amine of formulae ii, iii, or iv having the desired functionality at $L^3$. Methods for preparing such cyclic amines would be readily apparent to those skilled in the art. Alternatively, the desired —$L^3R^6$ moiety can be provided by replacing the —$L^3R^6$ moiety in viii, ix, or x can be replaced with a different, desired —$L^3R^6$ moiety using well known deprotection procedures.

General Scheme 3

Compounds according to Formula I, in which moiety A has structure A3 or A5 (wherein Q is =CH— or =N—), moiety $L^1$ is —S($O_2$)—, —C(O)—, or —$CH_2$—, moiety $L^2$ is —$SO_2$—, and moiety B has the structure B1, B2, or B3, may be prepared by the general method shown in General Scheme 3, below.

LG, wherein LG represents a leaving group such as chloride, bromide or thiolate, to give xxviii (e.g., at a temperature ranging from –15° C. to 0° C.). By appropriate selection of electrophile, the desired group $L^1$ (e.g., —S($O_2$)—, —C(O)—, —$CH_2$—, etc.) can be introduced.

In Step 2, compound xxviii is dissolved in a solvent such as DMF or toluene, and then treated with a base such as NaH, KH, or $CaH_2$. The resulting solution is treated with a suitable electrophile represented by the formula $R^7$—LG, wherein LG represents a leaving group such as chloride, bromide, or mesylate, to give compound xxix (e.g., at a temperature ranging from –15° C. to 0° C.).

In Step 3, compound xxix is dissolved in a solvent such as THF or DME and then reacted with a base such as n-BuLi (e.g., at a reaction temperature ranging from –110° C. to –78°

GENERAL SCHEME 3

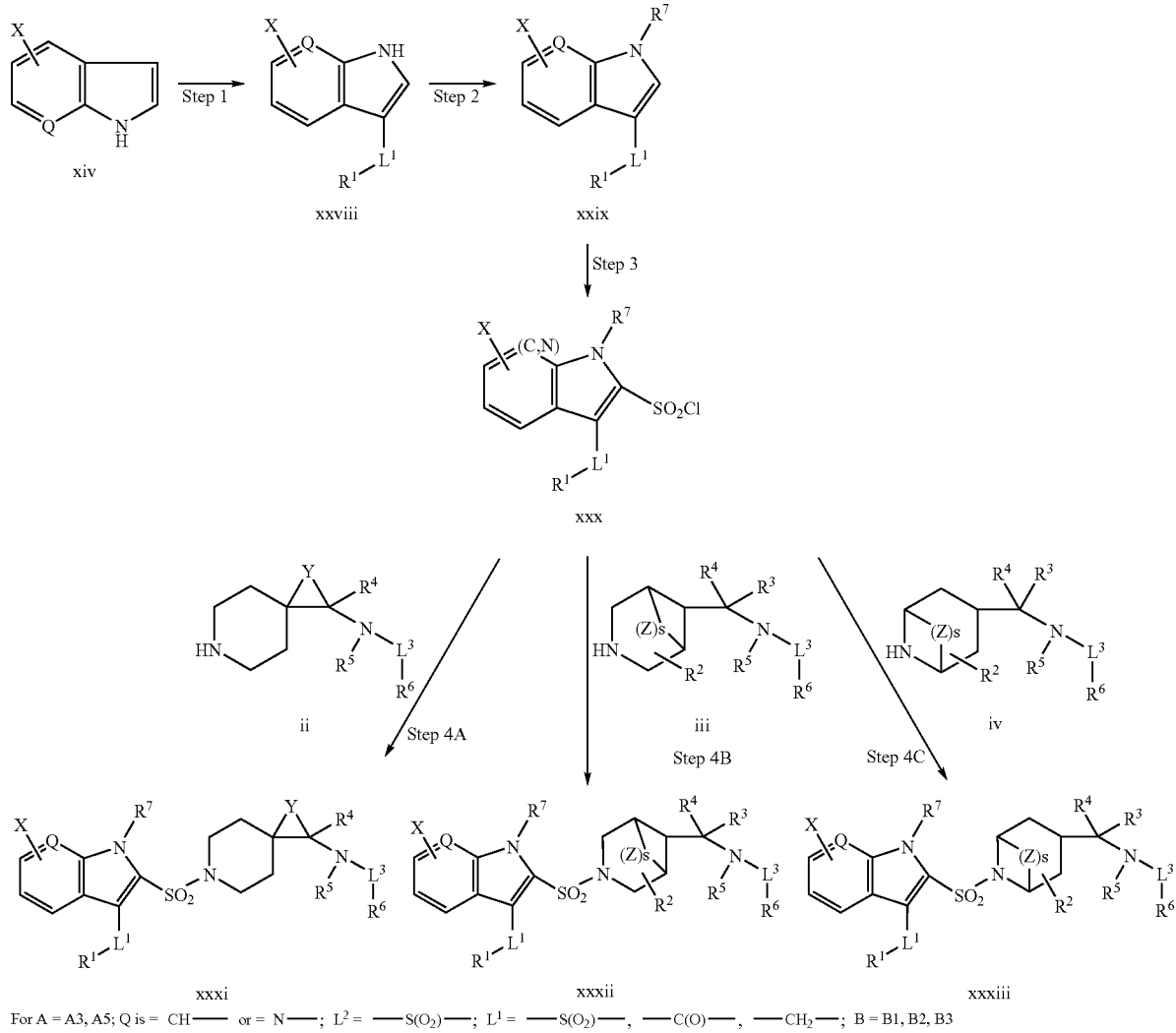

Description of General Scheme 3

In Step 1, indole (or azaindole) derivative xiv is dissolved in a solvent such as DMF and treated with a base such as NaH, KH, or $CaH_2$. The resulting solution is then treated with a suitable electrophile represented by the formula $R^1$—$L^1$—

C.). The resulting anion is exposed to $SO_2$ gas for a period of 1-2 h and then allowed to warm to room temperature. The solvent is removed and the residue is redissolved in solvent such as methylene chloride or dichloroethane and then treated with N-chlorosuccinimide to give sulfonyl chloride xxx.

In Steps 4A, 4B, and 4C, amines of the formulae ii, iii, and iv, respectively, are reacted with a base such as triethyl amine or diisopropylethyl amine in an organic solvent such as methylene chloride or dichloroethane. Sulfonyl chloride xxx is then added to give corresponding sulfonamides xxxi, xxxii, and xxxiii (e.g., at reaction temperatures ranging from −15° C. to 0° C.).

The desired functional group $L^3$ may be introduced into the product by the selection of the appropriate cyclic amine of formulae ii, iii, or iv having the desired functionality at $L^3$. Methods for preparing such cyclic amines would be readily apparent to those skilled in the art. Alternatively, the desired —$L^3R^6$ moiety can be provided by replacing the —$L^3R^6$ moiety in viii, ix, or x can be replaced with a different, desired —$L^3R^6$ moiety using well known deprotection procedures.

It should be noted that reactive groups not involved in any of the processes disclosed herein can be protected during the reactions with conventional protecting groups that can be removed by standard procedures after the reaction. The following Table II shows some typical protecting groups:

TABLE II

| Group to be Protected | Group to be Protected with Protecting Group |
|---|---|
| —C(O)O—OH | —C(O)O-alkyl, —C(O)O-benzyl, —C(O)O-phenyl |
| —NH— | —N(C(O)alkyl)-, —N(C(O)benzyl)-, —N(C(O)phenyl)-, —N(CH$_2$OCH$_2$CH$_2$Si(CH$_3$)$_3$)—, —N(C(O)OC(CH$_3$)$_3$)—, —N(benzyl)-, —N(Si(CH$_3$)$_3$)—, —N(Si(CH$_3$)$_2$C(CH$_3$)$_3$)— |
| —NH$_2$ | 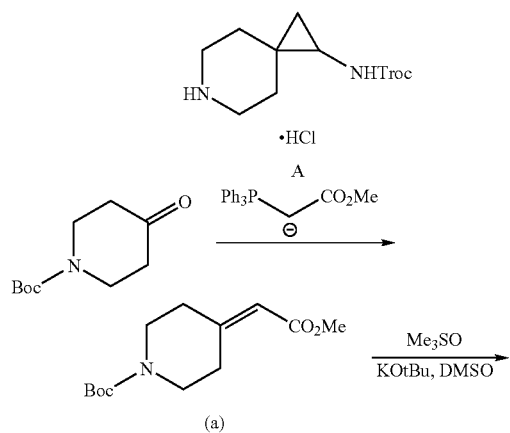 |
| —OH | —OCH$_3$, —OCH$_2$OCH$_3$, —OSi(CH$_3$)$_3$, —OSi(CH$_3$)$_2$C(CH$_3$)$_3$, —OCH$_2$-phenyl |

Preparation of Starting Material A

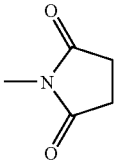

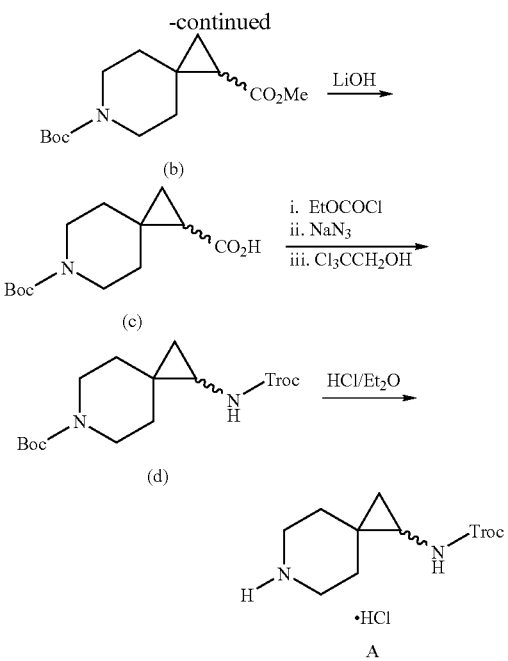

Step 1: Methyl(triphenylphosphoanylidene)acetate (104.5 g, 0.31 mmol) was added to a solution of NBoc-piperidine (49.79 g, 0.25 mol) in toluene (625 mL). The resulting reaction mixture was heated to reflux and stirred for 17 h. The reaction mixture was then cooled to room temperature and concentrated under vacuum. The resulting residue was then pre-adsorbed on silica gel and purified by eluting it through a plug of silica gel with 50% ethyl acetate/hexanes, to yield unsaturated ester (a) (62.16 g, 0.243 mol) as a white solid.

Step 2: Potassium tert-butoxide (450 g, 0.41 mol) was added to a solution of trimethylsulfoxonium iodide (90.0 g, 0.41 mol) in DMSO (700 mL), in one portion. The mixture was stirred at room temperature for 3 h. The unsaturated ester (a) (59.64 g, 0.23 mol) prepared in step 1 was dissolved in DMSO (0.26 L) and added to the reaction mixture. The reaction mixture was stirred for 20 h at room temperature and then added to brine (1 L). Saturated aqueous NH$_4$Cl was then added to the reaction mixture in order to adjust the pH to approximately 7. The reaction mixture was then extracted several times with ether, the ether extracts combined, washed with water and brine, dried with anhydrous MgSO$_4$, filtered, and concentrated under vacuum to yield ester (b) (53.5 g, 0.20 mol) as an oil.

Step 3: An aqueous LiOH solution (2N, 200 mL) was added to a solution of the ester (b) prepared in step 2 (53.5 g, 0.20 mol) in THF (200 mL). The mixture was then stirred at room temperature for 17 h, diluted with water (750 mL) and washed with ether. The ether phase was discarded, and the aqueous phase acidified to a pH of 3-4 with 6N HCl. The acidified aqueous phase was then extracted with ether several times. The ether washes were combined, washed with water and brine, dried with anhydrous MgSO$_4$, filtered, and concentrated under vacuum to provide carboxylic acid (c) (49.25 g, 0.19 mol) as a white solid.

Step 4: Triethylamine (8.7 g, 0.086 mol) followed by ethyl chloroformate (9.4 g, 0.86 mol) was added to a solution of carboxylic acid (c) (20.0 g, 0.078 mol) in acetone (78 mL) at 0° C. The resulting mixture was stirred at 0° C. for 40 minutes. Sodium azide (10.2 g, 0.15 mol) in water (50 mL) was then added to the mixture. The mixture was then allowed to warm to room temperature and stirred for 4 h. Water was then added, and then the mixture was extracted several times with CH₂Cl₂. The organic phases were combined and washed with water and brine, then dried (anhydrous MgSO₄), filtered, and concentrated under vacuum to provide an oil. The oil was taken up into toluene (200 mL), 2,2,2-trichloroethanol (14.0 g, 0.094 mol) was added, and the mixture was warmed to reflux and stirred at reflux for 17 h. The reaction mixture was then cooled to room temperature and EtOAc (250 mL) was added. Then, the mixture was washed with water and brine, dried (anhydrous MgSO4), filtered and concentrated under vacuum. The resulting residue was purified by silica gel chromatography (35% ethyl acetate/hexanes) to provide the carbamate (d) (24.4 g, 0.061 mol).

Step 5: HCl/Et₂O (2 N, 50 mL) was added to a solution of the carbamate (d) prepared in step 4 (24.4 g, 0.061 mol) in CH₂Cl₂ (100 mL). The reaction mixture was stirred overnight and then concentrated under vacuum to yield (e) as a hygroscopic foam (17.4 g, 0.0.052 mol).

Preparation of Starting Material B

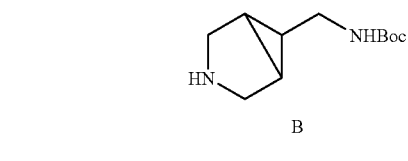

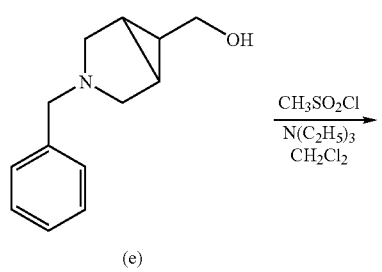

(e)

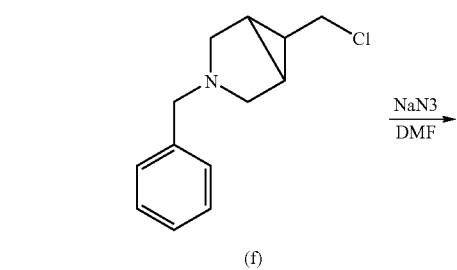

(f)

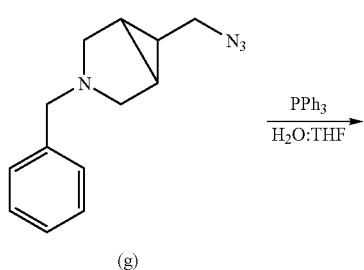

(g)

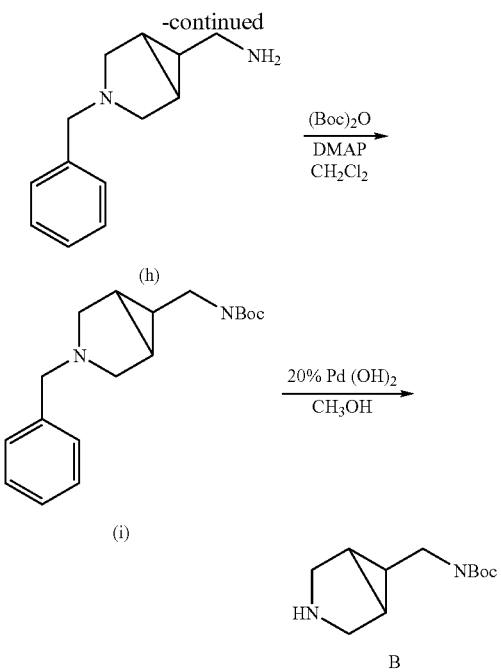

Starting alcohol (e) (1a, 5a, 6a)-3-benzyl-6-hydroxymethyl-3-azabicyclo[3.1.0]hexane was prepared by known methods (i.e., Brighty, K. E; Castaldi, M. J Synlett, 1996, 1097, herein incorporated by reference in its entirety).

Step 1: Alcohol (e) (11 g, 54 mmol) and triethylamine (38 mL, 27 mmol) were dissolved in CH₂Cl₂ (200 mL) and cooled to 0° C. The cooled solution was stirred, and CH₃SO₂Cl (as a CH₂Cl₂ solution; 6 mL, 78 mmol, 25 mL CH₂Cl₂) was added dropwise, and the stirring was continued for 3-4 h. The reaction mixture was then washed two times with 100 mL of water and two times with 100 of brine. The organic and aqueous phases were separated, and the organic phase was dried, and concentrated to provide a crude product. The crude product was purified by silica gel chromatography (eluted with 1:6 ethyl acetate:hexane). The appropriate fractions were collected from the chromatography column and concentrated to provide pure chloro compound (f) as an oil (7 g, 59%).

Step 2: The chloro compound prepared in step 1 was dissolved in DMF (100 mL) and treated with NaN₃ (10.3 g, 157 mmol), and the mixture was stirred vigorously for 36-48 h. The reaction mixture was then diluted with 100 mL water and extracted with ethyl acetate (two times with 100 mL of ethyl acetate). The organic phases were combined, dried, and concentrated to yield pure azide (g) (6.2 g, 87%).

Step 3: The azide (g) (6.2 g, 27 mmol) prepared in step 2 and triphenylphosphine (15 g, 57 mmol) were dissolved in 100 mL of THF, and then water (6 mL, 333 mmol) was added. The resulting mixture was stirred vigorously for 16-24 h. The solvent was removed and the crude amine (h) was obtained without further purification.

Step 4: The crude amine (h) prepared in step 3 and N,N-dimethylaminopyridine (DMAP) (0.66 g, 5.4 mmol) were dissolved in CH₂Cl₂ (100 mL). To this solution was added di-tert-butyldicarbonate (7 g, 33 mmol), in portions, and the reaction mixture was stirred for 16 h. The reaction mixture was then washed two times (50 mL) with water and once with brine (50 mL). The organic phase was isolated and dried, and the solvent was removed under reduced pressure. The crude product was subjected to silica gel chromatography using 1:3 ethyl acetate:hexane as the eluting solvent. The eluted fractions were combined and concentrated to yield 6.9 g of pure carbamate (i) (84%).

Step 5: The carbamate (i) (1.9 g, 6.3 mmol) prepared in step 4 was dissolved in methanol (100 mL) and mixed with palladium hydroxide (20%, 0.4 g). The mixture was transferred to a Parr bottle, which was then charged with hydrogen to a pressure of 20 psi. The Parr bottle was shaken for 10 h. The remaining hydrogen was removed from the Parr bottle under vacuum, and the reaction was filtered through Celite (diatomaceous earth). The filtrate was then concentrated to provide pure amine B (1.4 g).

Preparation of Starting Material C

Step 2: The crude product (k) prepared in step 1 and triethylamine (TEA) (0.6 mL, 4.3 mmol) were dissolved in $CH_2Cl_2$ (50 mL). Di-tert-butyldicarbonate (0.85 g, 3.9 mmol) was added to this solution in portions, and the reaction mixture was stirred for 16 h. The reaction mixture was then washed two times with 50 mL of water and once with 50 mL of brine. The organic phase was dried and the solvent was removed under reduced pressure. The crude product was subjected to silica gel chromatography using 2.5% ammonia saturated methanol in $CH_2Cl_2$ as the eluting solvent. The eluted fractions were combined and concentrated to yield 0.78 g of pure carbamate product (l) (61%).

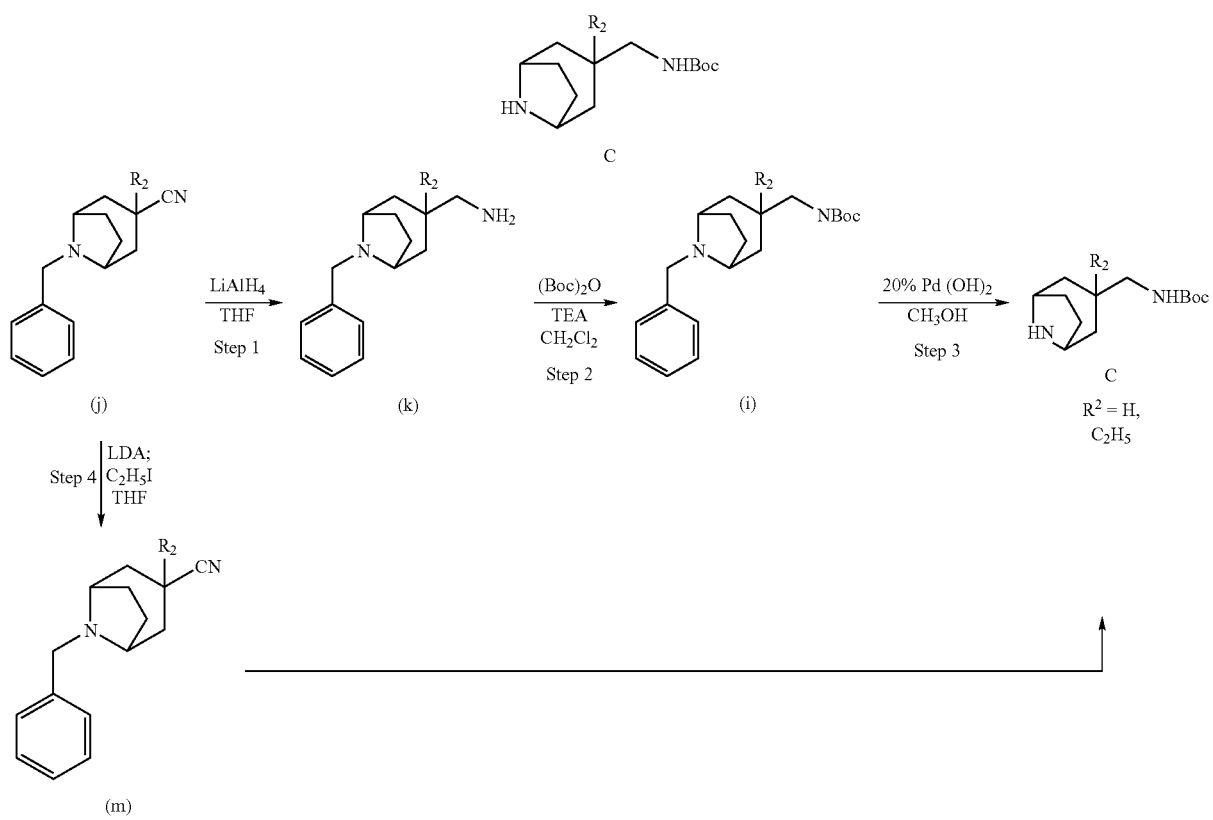

N-Benzyltropinanecarbonitrile (j) was prepared using known procedures (see, for example: Montzka, T. A.; Matiskella, J. D.; Partyka, R. A. *Tetrahedron Letters* 1974, 14, 1325; Lowe, J. A.; Drozda, S. E.; McLean, S.; Bryce, D. K.; Crawford, R. T.; Snider, R. M.; Tsuchiya, M. *J. Med. Chem.* 1994, 37, 2831; both of which are herein incorporated by reference in their entirety).

Step 1: LiAlH$_4$ was added to dry THF (40 mL) and the mixture was then cooled to 0° C. Then carbonitrile (j) (0.9 g, 3.8 mmol, in a 10 mL THF solution) was added to the mixture dropwise. The reaction mixture was allowed to warm to ambient temperature and stirred for 48 h, then cooled to back to 0° C. and quenched by the sequential addition of 1 mL of water, 2 mL of 0.5 N aq. NaOH, and 1 mL of water. The resulting mixture was stirred vigorously for 2 h and then filtered through Celite. The filtrate was concentrated to yield pure (k) as an oil (0.9 g, 100%).

Step 3: The carbamate (l) (0.8 g, 2.3 mmol) of step 2 was dissolved in methanol (60 mL) and treated with palladium hydroxide (20%, 0.08 g). The mixture was transferred to a Parr bottle, which was then charged with hydrogen to a pressure of 20 psi. The Parr bottle was shaken for 10 h. The hydrogen was removed from the Parr bottle under vacuum, and the reaction mixture was filtered through Celite. The filtrate was then concentrated to provide pure amine C (0.6 g; $R^2$ is H).

Step 4: Starting material N-Benzyltropinanecarbonitrile (j) (0.6 g, 2.6 mmol) in anhydrous THF (50 mL) was cooled to −70° C. and treated with lithium diisopropylamine (LDA) (2.65 mL, 2M THF solution). The resulting solution was then treated with ethyl iodide (1.2 g, 7.8 mmol) and stirred for 3 h. The reaction mixture was quenched with water and allowed to warm to room temperature and diluted with ethyl acetate (100 mL). The organic phase was isolated and washed in sequence once with 50 mL of water and two times with 50 mL of brine. The organic phase was dried and concentrated and the resulting crude product was purified by silica gel chromatography using 1:3 ethyl acetate: hexane as the eluting solvent mixture. Compound (m) was converted to compound (c) ($R^2$=$C_2H_5$) using methods similar to those described in steps 1, 2, and 3, except that instead of N-benzyltropinanecarbonitrile (j) (i.e., $R^2$=H), the analogous starting material in which $R^2$ is $C_2H_5$ was used.

Example 1

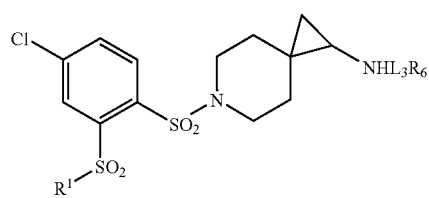

Compounds having the general formula shown above may be prepared by the methods described below, or by similar methods that would be apparent to those skilled in the art.

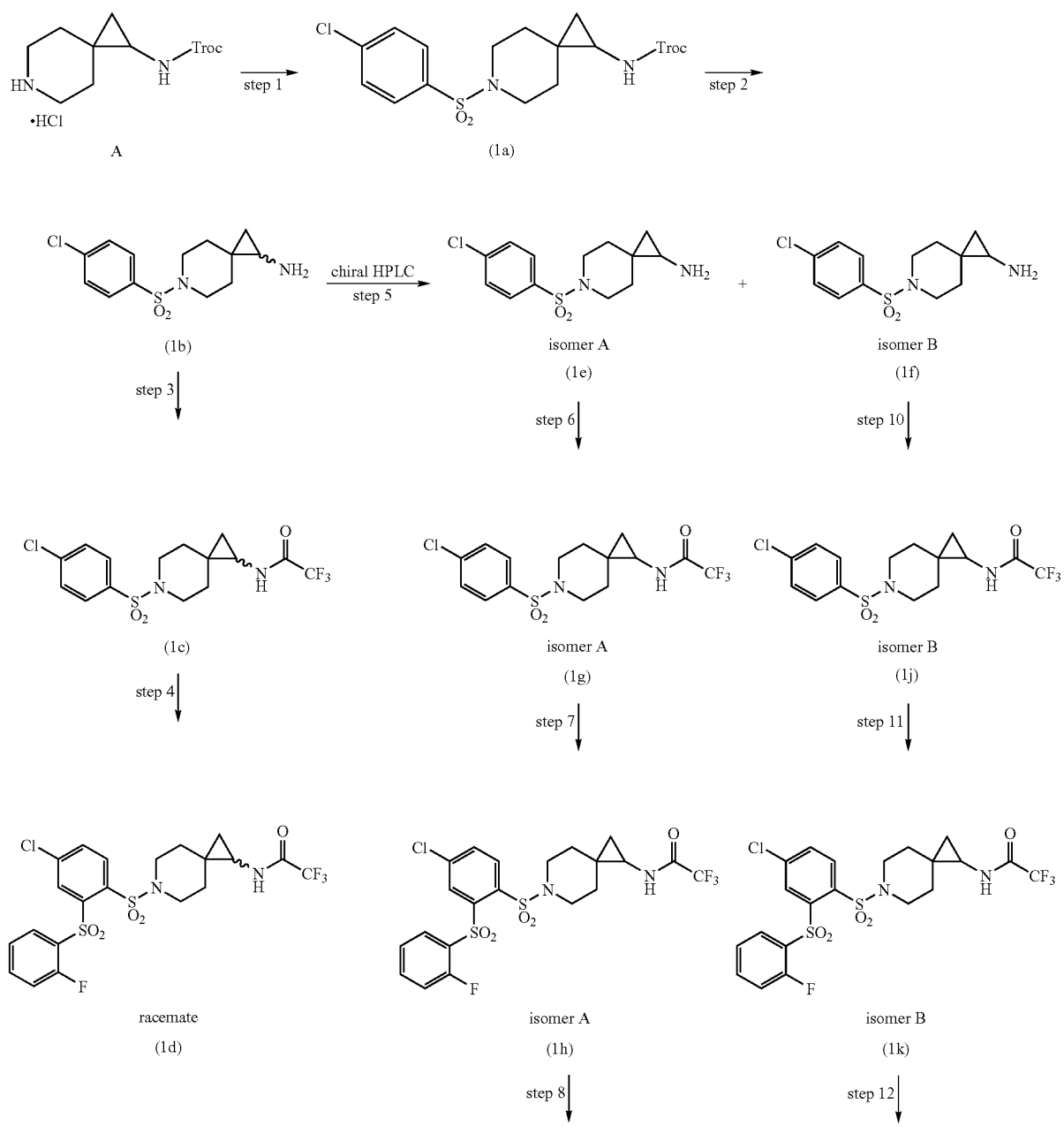

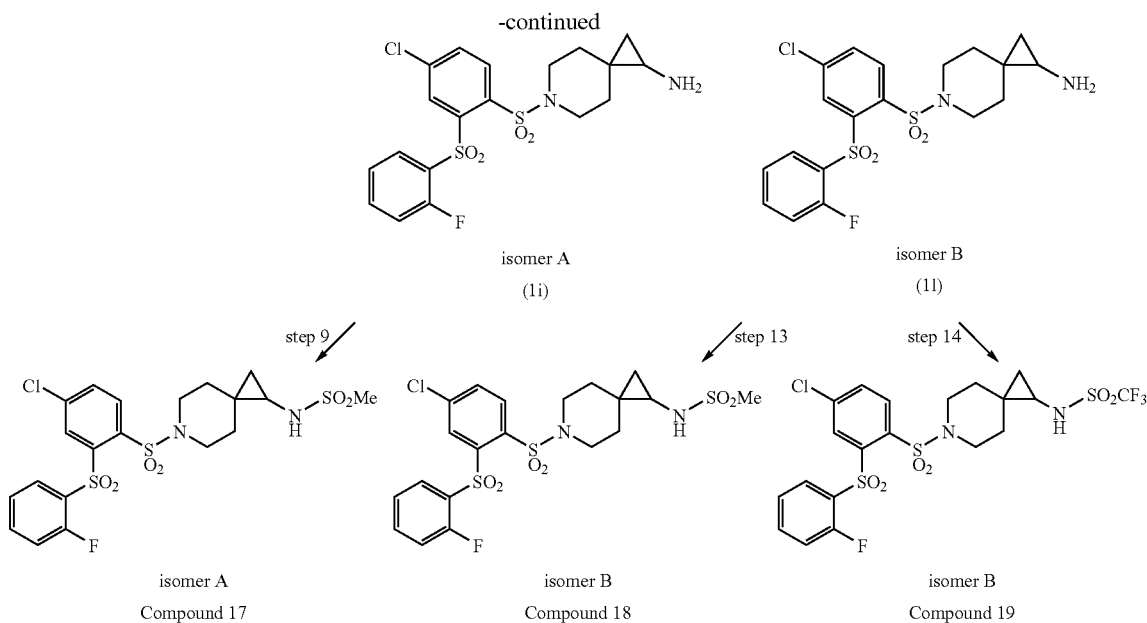

Step 1: TEA (1.45 g, 14.4 mmol) was added to carbamate A (1.94 g, 5.75 mmol) in CH₂Cl₂ at 0° C., followed by the addition of 4-chlorobenzenesulfonyl chloride (1.52 g, 7.18 mmol) in one portion. The reaction mixture was allowed to warm to room temperature and stirred for 2 h, diluted with methylene chloride, washed with 1N HCl, water, and brine, then dried (anhydrous MgSO₄), filtered, and concentrated under vacuum. The crude product was purified by silica gel chromatography to yield the sulfonamide (1a) (2.0 g, 4.2 mmol).

Step 2: Zinc dust (17.7 g, 273 mmol) was added to a solution of sulfonamide (1a) (2.0 g, 4.2 mmol) and AcOH (42 mL). The resulting mixture was stirred at room temperature for 3 h, diluted with EtOAc, filtered through a plug of silica gel, and the filtrate concentrated under vacuum. The resulting residue was dissolved in methylene chloride, then saturated NaHCO₃ was added, and the mixture was stirred vigorously for 15 minutes. The aqueous layer was extracted with methylene chloride. The organic phases were combined, washed with water and brine, dried (anhydrous MgSO₄), filtered, and concentrated under vacuum to provide the amine (1b) (0.95 g, 3.2 mmol).

Step 3: Ethyl trifluoroacetate (0.37 g, 2.6 mmol) was added to a solution of the amine (1b) (0.26 g, 0.86 mmol) in dichloroethane (3 mL). The resulting mixture was warmed to 45° C. and ethyl trifluoroacetate (0.24 g, 1.72 mmol) was added. The reaction mixture was then warmed to 60° C., stirred for 6 h and then concentrated under vacuum. The concentrated crude product was purified by silica gel chromatography (30% EtOAc/hexanes) to provide the trifluoroacetamide (1c) (0.167 g, 0.42 mmol).

Step 4: n-butyllithium (1.6 M, 0.59 mL) was added to a solution of trifluoroacetamide (1c) (0.16 g, 0.42 mmol) in THF at −78° C. The reaction mixture was stirred for 0.5 h, and then 2-fluorophenyldisulfide (0.16 g, 0.63 mmol) in THF (0.6 mL) was added. The resulting mixture was stirred at −78° C. for 2 h. Water was then added, the mixture was warmed to room temperature, and extracted with EtOAc. The organic phases were combined, washed with water and brine, dried (anhydrous MgSO₄), filtered, and concentrated under vacuum. The concentrated product was purified by silica gel chromatography (35% EtOAc/hexanes) to provide a racemic intermediate product (0.13 g, 0.25 mmol). The racemic intermediate product was dissolved in DCE without further purification or isolation, and n-CPBA (0.21 g, 0.84 mmol) was added thereto. The resulting reaction mixture was stirred for 17 h at room temperature, diluted with CH₂Cl₂, washed with water and brine, dried (anhydrous MgSO₄), filtered, and concentrated under vacuum. The resulting concentrated product was purified by silica gel preparative plate chromatography (45% EtOAc/hexanes) to provide (1d) (0.067 g, 0.12 mmol).

Step 5: The two enantiomers of amine (1 b) (1.42 g, 4.71 mmol) were separated by chiral HPLC (Chiralpak AD column, 5 cm×50 cm, 20 μm particle size, 48 mL/min flow rate) eluted with 25% IPA/hexanes to provide isomer A (1e) (0.57 g, 1.9 mmol) and isomer B (1f) (0.55 g, 1.8 mmol).

Step 6: TEA (0.16 g, 1.58 mmol) followed by trifluoroacetic anhydride (0.20 g, 0.94 mmol) where added to a solution of enantiomer (1e) (0.24 g, 0.79 mmol) in DCE (2.6 mL) at 0° C. The reaction mixture was allowed to warm to room temperature, and stirred for 18 h. The mixture was then diluted with CH₂Cl₂, washed with water and brine, dried (anhydrous MgSO₄), filtered, and concentrated under vacuum. The concentrated product was purified by silica gel chromatography (30% EtOAc/hexanes) to provide the trifluoroacetamide (1g) (0.25 g, 0.63 mmol).

Step 7: n-butyllithium (1.8 M, 0.67 mL) was added to a solution of trifluoroacetamide (1g) (0.21 g, 0.54 mmol) in THF (2 mL) which was cooled to −78° C. The reaction mixture was stirred for 30 minutes and then 2-fluorophenyldisulfide (0.17 g, 0.68 mmol) in THF (0.8 mL) was added. The reaction mixture was allowed to slowly warm to room temperature over 17 h. Saturated NH₄Cl was then added, and the reaction mixture was extracted with EtOAc. The organic phases were combined and washed with water and brine, dried (anhydrous MgSO₄), filtered, and concentrated under vacuum. The resulting purified product was purified by silica gel chromatography (30% EtOAc/hexanes) to provide a mixture of starting trifluoroacetamide and the desired thioether product (0.13 g). The mixture was taken up into DCE (2 mL)

without further purification, and m-CPBA (0.22 g, 0.90 mmol) was added. The resulting mixture was stirred at room temperature for 22 h. The reaction mixture was then diluted with CH$_2$Cl$_2$, washed with water and brine, dried (anhydrous MgSO$_4$), filtered, and concentrated under vacuum. The concentrated product was purified by silica gel chromatography (30-40% EtOAc/hexanes) to provide (1h) (0.034 g, 0.061 mmol).

Step 8: Aqueous LiOH (2N, 0.09 mL) was added to a solution of (1h) (0.034 g, 0.06 mmol) in THF (0.5 mL). The resulting mixture was stirred at room temperature for 27 h, then water was added and the mixture extracted with EtOAc. The organic phases were combined and washed with water and brine, dried (anhydrous MgSO$_4$), filtered and concentrated under vacuum to provide the amine (1i) (0.028 g, 0.06 mmol).

Step 9: TEA (0.012 g, 0.12 mmol) followed by methanesulfonyl chloride (0.010 g, 0.09 mmol) was added to a solution of the amine (1i) (0.026 g, 0.06 mmol) in DCE (0.4 mL). The resulting reaction mixture was stirred at room temperature for 19 h, and then concentrated under vacuum. The concentrated product was purified by silica gel preparative plate chromatography (70% EtOAc/hexanes) to provide the methanesulfonamide Compound 17 (0.016 g, 0.03 mmol).

Step 10: TEA (0.15 g, 1.5 mmol) followed by trifluoroacetic anhydride (0.19 g, 0.88 mmol) was added to a solution of the amine (1f) (0.22 g, 0.73 mmol) in DCE (2.4 mL) maintained at 0° C. The reaction mixture was allowed to slowly warm to room temperature while stirring for 17 h. CH$_2$Cl$_2$ was then added to the reaction mixture, which was then washed with water and brine, dried (anhydrous MgSO$_4$), filtered and concentrated under vacuum to provide the trifluoroacetamide (1j) (0.27 g, 0.67 mmol).

Step 11: n-butyllithium (1.8 M, 0.80 mL) was added to a solution of (1j) (0.25 g, 0.64 mmol) in THF (2.1 ml), maintained at −78° C. The reaction mixture was stirred at −78° C. for 25 minutes. 2-fluorophenyidisulfide (0.24 g, 0.96 mmol) in THF (0.8 mL) was then added to the reaction mixture. The reaction mixture was allowed to slowly warm to room temperature over 19 h. Saturated NH$_4$Cl was then added, and the reaction mixture was extracted with EtOAc. The organic phases were combined and washed with water and brine, dried (anhydrous MgSO$_4$), filtered, and concentrated under vacuum. The residue was purified by silica gel chromatography (30% EtOAc/hexanes) to provide the thioether (0.23 g, 0.44 mmol). The thioether was taken up into DCE (3 mL) without further purification or isolation, then m-CPBA (0.38 g, 1.54 mmol) was added and the mixture stirred at room temperature for 24 h. CH$_2$Cl$_2$ was then added to the mixture, and the mixture was washed with water and brine, and the organic layer was dried (anhydrous MgSO$_4$), filtered, and concentrated under vacuum. The residue was purified by silica gel chromatography (35% EtOAc/hexanes) to provide (1k) (0.13 g, 0.23 mmol).

Step 12: Aqueous LiOH (2N, 0.35 mL) was added to a solution of (1k) (0.13 g, 0.23 mmol) in THF (1.5 mL) at room temperature. The reaction mixture was stirred for 21 h. Water was then added, and the reaction mixture was extracted with EtOAc. The organic phases were combined and washed with water and brine, dried (anhydrous MgSO$_4$), filtered, and concentrated under vacuum to provide the amine (1l) (0.11 g, 0.23 mmol).

Step 13: TEA (0.02 g, 0.20 mmol) followed by methanesulfonyl chloride (0.016 g, 0.15 mmol) was added to a solution of amine (1l) (0.046 g, 0.10 mmol) in DCE (0.7 mL) at room temperature. The reaction mixture was stirred at room temperature for 17 h and concentrated under vacuum. The residue was purified by silica gel preparative plate chromatography (70% EtOAc/hexanes) to provide Compound 18 (0.04 g, 0.08 mmol).

Step 14: TEA (0.02 g, 0.16 mmol) followed by Tf$_2$O (0.035 g, 0.12 mmol) was added to a solution of the amine (1l) (0.05 g, 0.11 mmol) in CH$_2$Cl$_2$ at −78° C. The reaction mixture was stirred at −78° C. for 5 h and then warmed to room temperature. CH$_2$Cl$_2$ was added to the reaction mixture, which was then washed with water and brine. The organic phase was then dried (anhydrous MgSO$_4$), filtered, and concentrated under vacuum. The residue was purified by silica gel preparative plate chromatography (35% EtOAc/hexanes) to provide Compound 19 (0.045 g, 0.08 mmol).

Compounds 16, 23, 27, 28, 29, 30, 31, 32, 33, 34, 35, 36, 37, 38, 39, and 40 (Table 1) were prepared using methods similar to those described above in Example 1. One skilled in the art would readily understand these variations in the methods of Example 1.

For example, Compound 16 was prepared in a manner similar to Compounds 17 and 18, except that the racemic mixture (1b) was subjected to steps 6-9, without the chiral separation step (i.e., step 5).

Compounds 23, 27, and 28 were prepared in a manner similar to that of Compound 19, except that in step 11, 2-pyridyldisulfide, 4-trifluoromethoxyphenyldisulfide, and 4-methoxyphenyidisulfide, respectively, were used in place of 2-fluorophenyldisulfide.

Compound 29 was prepared in a manner similar to that of Compound 19, except that in step 1, A was reacted with 4-trifluoromethylbenzene sulfonyl chloride.

Compound 30 was prepared in a manner similar to that of Compound 19, except that in step 1, A was reacted with 4-trifluoromethylbenzene sulfonyl chloride, and in step 11, 2-fluorophenyldisulfide was replaced with 4-trifluoromethoxyphenyldisulfide.

Compound 31 was prepared in a manner similar to that of Compound 19, except that in step 1, A was reacted with 4-trifluoromethylbenzene sulfonyl chloride, and in step 11, 2-fluorophenyldisulfide was replaced with 2-pyridyidisulfide.

Compound 32 was prepared in a manner similar to that of Compound 19, except that in step 1, A was reacted with 4-trifluoromethoxybenzene sulfonyl chloride.

Compound 33 was prepared in a manner similar to that of Compound 19, except that in step 1, A was reacted with 4-methoxybenzene sulfonyl chloride, and in step 11, 2-fluorophenyldisulfide was replaced with 2-pyridyldisulfide.

Compound 34 was prepared in a manner similar to that of Compound 19, except that in step 1, A was reacted with benzene sulfonyl chloride, and in step 11, 2-fluorophenyldisulfide was replaced with 2-pyridyldisulfide.

Compound 35 was prepared in a manner similar to that of Compound 19, except that in step 1, A was reacted with 4-fluorobenzene sulfonyl chloride, and in step 11, 2-fluorophenyldisulfide was replaced with 2-pyridyldisulfide.

Compound 36 was prepared in a manner similar to that of Compound 18, except that in step 7, 2-fluorophenyldisulfide was replaced with 2-pyridyldisulfide.

Compound 37 was prepared in a manner similar to that of Compound 18, except that in step 7, 2-fluorophenyldisulfide was replaced with 2-pyridyldisulfide, and in step 9, cyclopropylsulfonyl chloride was used instead of methane sulfonyl chloride.

Compound 38 was prepared in a manner similar to that of Compound 19, except that in step 1, A was reacted with 4-hydroxybenzene sulfonyl chloride, and in step 11, 2-fluorophenyldisulfide was replaced with 2-pyridyldisulfide.

Compound 39 was prepared in a manner similar to that of Compound 32, except that in step 11, 2-fluorophenyidisulfide was replaced with 2-pyridyidisulfide, and in step 14, the amine intermediate product formed after step 12 was reacted with 2,2,2-trifluoroethyl triflate instead of $Tf_2O$.

Compound 40 was prepared in a manner similar to that of Compound 19, except that in step 1, A was reacted with 4-trifluoromethoxybenzene sulfonyl chloride, and in step 11, 2-fluorophenyldisulfide was replaced with 2-pyridyldisulfide.

Example 2

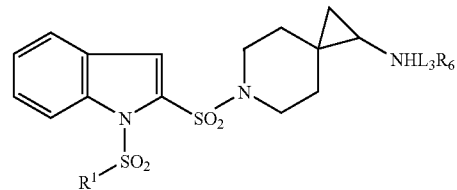

Compounds having the general formula shown above may be prepared by the methods described below, or by similar methods that would be apparent to those skilled in the art.

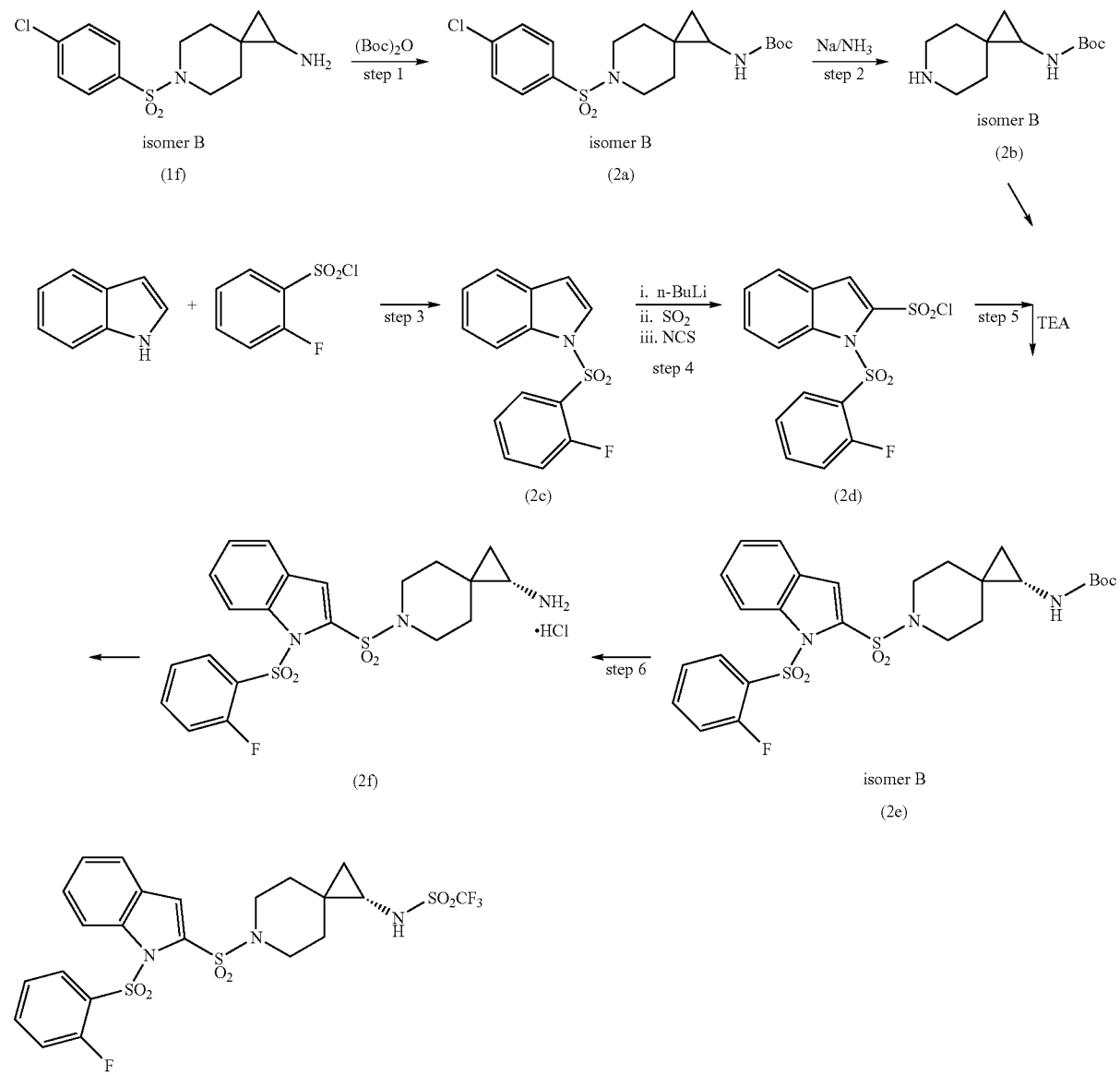

Step 1: TEA (0.62 g, 6.12 mmol) followed by (Boc)$_2$O (0.84 g, 3.82 mmol) was added to a solution of intermediate compound (1f) (0.92 g, 3.06 mmol) in DCE (10 mL), which was prepared in step 5 of the method described in Example 1. The reaction mixture was stirred for 16 h at room temperature. The reaction mixture was then diluted with CH$_2$Cl$_2$ and washed with 1N NaOH, 1N HCl, water, and brine. The organic phase was then dried (anhydrous MgSO$_4$), filtered, and concentrated under vacuum to provide the carbamate (2a) (1.22 g, 3.04 mmol).

Step 2: NH$_3$ was condensed in a flask at −78° C. (125 mL). Solid sodium pieces were added to the NH$_3$ to maintain a blue color. A solution of the carbamate (2a) prepared in step 1 (1.22 g, 3.0 mmol) in THF (12 mL) was added to the condensed NH$_3$ and sodium mixture. The reaction mixture turned orange and additional sodium was added until a blue color was maintained. The reaction mixture was stirred at −78° C. for 2.5 h. Then solid NH$_4$Cl was added and N$_2$ gas was passed over the reaction mixture in order to evaporate the liquid NH$_3$. Solid NaCl and 1N NaOH were then added, and the reaction mixture was extracted with CH$_2$Cl$_2$. The phases were combined and washed with water and brine, then dried (anhydrous MgSO$_4$), filtered, and concentrated under vacuum to provide the nonracemic amine (2b) (0.53 g, 2.34 mmol).

Step 3: 50% aqueous NaOH (30 mL) followed by benzyltriethylammonium bromide (0.025 g, 0.11 mmol) and 2-fluorophenyl sulfonyl chloride (6.0 g, 31 mmol) was added to a solution of indole (3.0 g, 26 mmol) in toluene (20 mL). The reaction mixture was stirred at room temperature for 20 h. Then water was added, and the mixture was extracted with EtOAc. The organic phases were combined and washed with water and brine, dried (anhydrous MgSO$_4$), filtered, and concentrated under vacuum to provide (2c) (7.0 g, 25.7 mmol).

Step 4: n-butyllithium (1.1 M, 12 mL) was added to a solution of diisopropyl amine (1.32 g, 13.1 mmol) in THF (22 mL) at 0° C. The solution was stirred at 0° C. for 1 h, thereby providing a solution of LDA (lithium diisopropylamine). The LDA solution was then added to a solution of the indole derivative (2c) prepared in step 3 (3.0 g, 10.9 mmol) in THF (26 mL), which was maintained at −78° C. The resulting reaction mixture was stirred at −78° C. for 1 h, and then SO$_2$ gas was bubbled through the reaction mixture for 15 minutes. The cold bath was removed, which allowed the reaction to warm to room temperature. The reaction mixture was concentrated under vacuum. The resulting solid was dissolved in CH$_2$Cl$_2$ (26 mL) and N-chlorosuccinimide (1.75 g, 13.1 mmol) was added. The resulting reaction mixture was stirred at room temperature for 75 minutes, then diluted with CH$_2$Cl$_2$, washed with water and brine, dried (anhydrous MgSO$_4$), filtered, and concentrated under vacuum. The resulting residue was adsorbed on silica gel and purified by silica gel chromatography (15% EtOAc/hexanes) to provide (2d) (1.3 g, 3.5 mmol) containing approximately 20% of the starting indole (2c).

Step 5: TEA (0.059 mL, 0.42 mmol) followed by the indole sulfonyl chloride (2d) (0.04 g, 0.17 mmol) prepared in step 4 was added to a solution of the amine (2b) (0.10 g, 0.21 mmol) in CH$_2$Cl$_2$ (1.5 mL). The resulting reaction mixture was stirred at room temperature for 20 h. The reaction mixture was diluted with EtOAc and washed with 1 N HCl, water, and brine. The organic phase was dried (anhydrous MgSO$_4$), filtered, and concentrated under vacuum to provide an oil that was purified by silica gel prep plate chromatography (40% EtOAc/hexanes) to provide (2e) (0.07 g, 0.12 mmol).

Step 6: HCl/dioxane (4N, 1.5 mL) was added to a solution of the N-boc amine (2e) (0.07 g, 0.12 mmol) in CH$_2$Cl$_2$ prepared in step 5. The reaction mixture was stirred at room temperature for 17 h, and then concentrated under vacuum to provide (2f) in quantitative yield. The residue was taken up into CH$_2$Cl$_2$ and TEA was added (0.043 mL, 0.31 mmol). The reaction mixture was cooled to −78° C. and then Tf$_2$O was added (0.022 mL, 0.13 mmol). The reaction mixture was allowed to slowly warm to room temperature over 15 h, then diluted with EtOAc and washed with 1 N HCl, water, and brine. The organic phase was separated and dried (anhydrous MgSO$_4$), filtered, and concentrated under vacuum. The residue was purified by silica gel preparative plate chromatography (35% EtOAc/hexanes) to provide Compound 22 (0.05 g, 0.08 mmol).

Using racemic or resolved isomers of the amine (1a) (e.g., racemic mixture (1b), or resolved isomers (1e) or (1f), prepared by the methods of Example 1) Compounds 20, 21, 24, 25, 26, 41, 42, and 43 of Table 1 were prepared using methods similar to those described above in Example 2. These variations in the methods of Example 2 would be readily understood by those skilled in the art.

Compound 20 was prepared in a manner similar to that of Compound 22, except that the racemic amine (1b) was used in step 1 rather than isomer (1f), and in step 6, methanesulfonyl chloride was used instead of Tf$_2$O.

Compound 21 was prepared in a manner similar to that of Compound 22, except that the racemic amine (1b) was used in step 1 rather than isomer (1f).

Compound 25 was prepared in a manner similar to that of Compound 22, except that racemic amine (A) was used in step 5 rather than isomer (2b), and 5-bromoindole was used instead of indole in step 3.

Compound 24 was prepared in a manner similar to that of Compound 25, except that amine (A) was used instead of amine (2b), and in step 5, methanesulfonyl chloride was used instead of Tf$_2$O.

Compound 26 was prepared in a manner similar to that of Compound 25, except that amine isomer (1f) was used instead of racemic amine (A).

Compound 41 was prepared in a manner similar to that of Compound 22, except that 2-pyridyl sulfonyl chloride was used in step 3 instead of 2-fluorophenyl sulfonyl chloride.

Compound 42 was prepared in a manner similar to that of Compound 21, except that azaindole

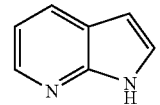

was used instead of indole in step 3.

Compound 43 was prepared in a manner similar to Compound 42, except that in step 6, methanesulfonyl chloride was used instead of Tf$_2$O.

Example 3

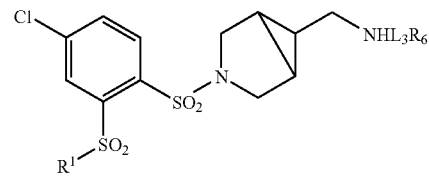

-continued

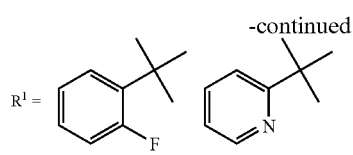

Compounds having the general formulae shown above may be prepared by the method shown below, or by similar methods that would be understood by those skilled in the art.

stirring an additional 4 h, the reaction mixture was diluted with ethyl acetate (50 mL) and washed sequentially with water (50 mL) then brine (50 mL). The organic phase was separated, dried and concentrated to yield 1.5 g of nitro compound (3a), which was used in next step without further purification.

Step 2: Tin chloride (2.4 g) was dissolved in 3:1 ethanol:HCl (30 mL), cooled to 0° C., and stirred until dissolution. The nitro compound (3a) (1.2 g, 3.9 mmol) from step 1 was added in portions, and the resulting suspension was stirred for

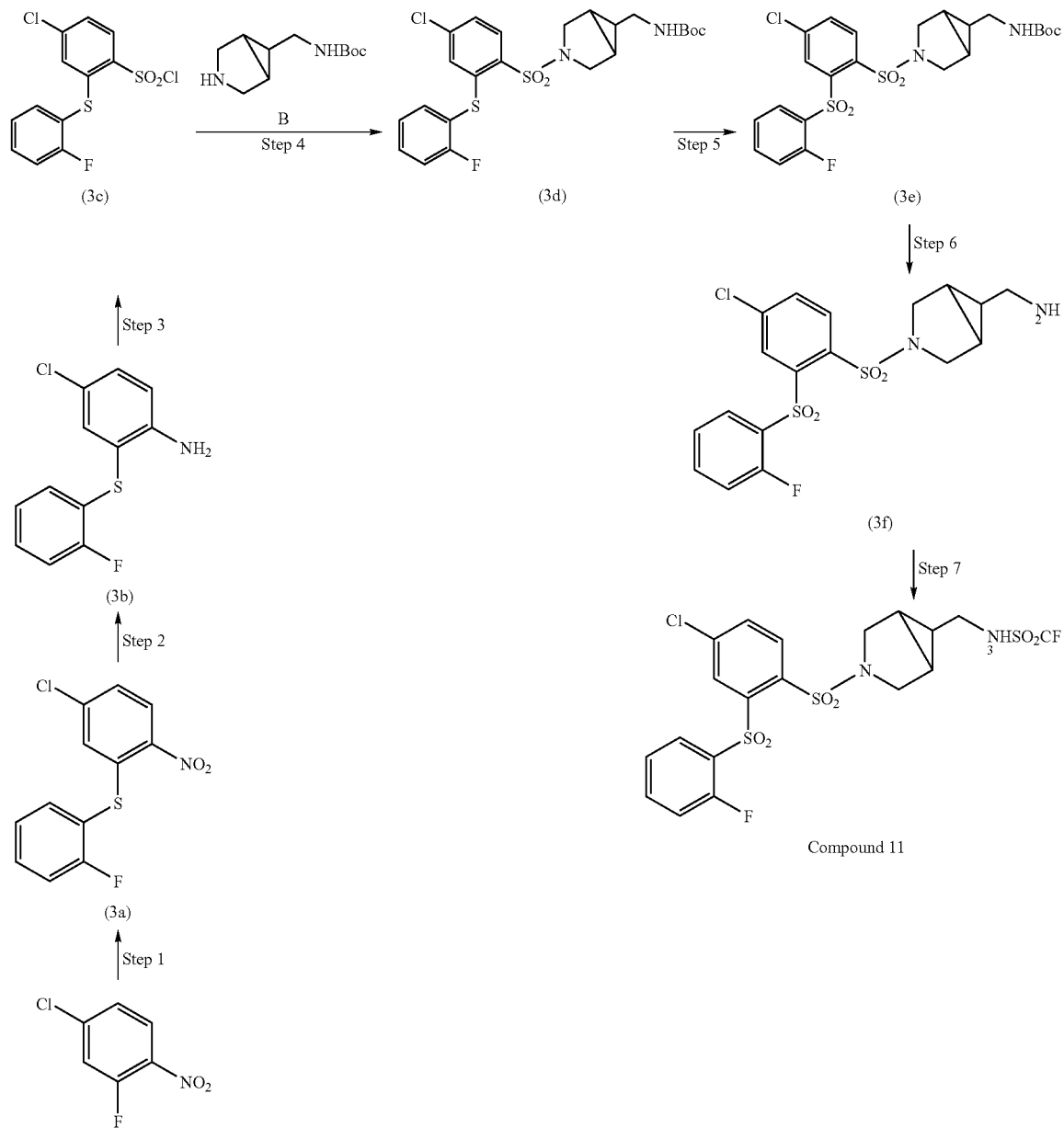

Step 1: A solution of 2-Fluorobenzene thiol (0.7 g, 5.5 mmol) in anhydrous THF (30 mL) was cooled to 0° C. and treated with NaH (0.26 g, 11.1 mmol). After stirring for 0.5 h, 2-fluoro-4-chloronitrobenzene was added and the reaction mixture was allowed to warm to room temperature. After 10 h at room temperature. The reaction was neutralized with aqueous NaOH (10 mL, 1N). The volatile organic components (e.g., ethanol) were removed under reduced pressure and the product was extracted from aqueous phase with ethyl acetate (extracted twice with 50 mL of ethyl acetate). The organic phases were combined and dried (anhydrous MgSO₄). The solvent was removed to provide 1.03 g of amine (3b), which was used in the next step without additional purification.

Step 3: The amine (3b) from step 2 (10.3 g, 3.6 mmol) was dissolved in 3:2 acetic acid:HCl (10 mL) and cooled to 0° C. An aqueous solution of NaNO₂ (0.3 g, 4.3 mmol) was added to the solution, dropwise, and the solution was stirred for 0.5 h. The resulting diazonium salt intermediate mixture was poured slowly into acetic acid presaturated with SO₂ gas and then treated with a catalytic amount of CuCl (0.8 g). The mixture was stirred for 1 h and then poured over crushed ice. This mixture was extracted twice with 50 mL of CH₂Cl₂, dried and concentrated to provide sulfonyl chloride (3c), which was used in the next step.

Step 4: A solution of amine B (0.06 g, 0.283 mmol) and triethylamine (0.3 mL, 1.4 mmol) in methylene chloride (25 mL) was treated with the sulfonyl chloride (3c) prepared in step 3. The mixture was stirred at room temperature for 5 h. The reaction mixture was then diluted with methylene chloride (50 mL) and washed sequentially with aqueous NaHCO₃ (50 mL), water (two aliquots of 50 mL each), and brine (50 mL). The organic phases were separated, dried, and concentrated to yield a crude product (3d), which was purified by preparative plate silica gel chromatography using 1:2 ethyl actetate:hexane as the eluting solvent.

Step 5: A solution of the product (3d) from step 4 (0.088 g, 0.172 mmol) in CH₂Cl₂ (50 mL) was treated with m-CPBA (0.097 g, 0.4 mmol) and the resulting mixture was stirred for 72 h. The reaction mixture was diluted with CH₂Cl₂ (50 mL) and washed sequentially with 5% aqueous NaHSO₃ (50 mL), aqueous NaHCO₃ (50 mL), water (50 mL), and brine (50 mL). The organic phases were separated, dried (Na₂SO₄), filtered, and concentrated. The resulting crude product was purified by preparative plate silica gel chromatography using ethyl acetate:hexane (1:2) as the solvent, to provide 0.085 g of pure sulfone product (3e).

Step 6: A solution of the sulfone product (3e) prepared in Step 5 (0.085 g, 0.156 mmol) in CH₂Cl₂ (10 mL) was treated with trifluoroacetic acid (0.06 mL, 0.77 mmol) and stirred for 2 h. The reaction mixture was neutralized with aqueous NaHCO₃, diluted with CH₂Cl₂ (50 mL) and washed sequentially with water (50 mL) and brine (30 mL). The organic phases were separated, dried (Na₂SO₄), and concentrated to yield pure amine (3f) (0.08 g).

Step 7: A solution of the amine (3f) (0.03 g, 0.067 mmol) prepared in the previous step and triethylamine (0.009 mL, 0.0667 mmol) in CH₂Cl₂ (10 mL) was cooled to −70° C. and treated with trifluoromethanesulfonic anhydride (0.016 g, 0.059 mmol). The reaction mixture was stirred for 1 h and then quenched with aqueous NaHCO₃ (20 mL). The quenched mixture was then warmed to room temperature and diluted with CH₂CL₂ (50 mL). The organic phase was separated, dried, and concentrated, and then the crude product was subjected to silica gel preparative plate chromatography using 1:2 ethyl acetate: hexane as the solvent to provide pure Compound 11 (0.02 g).

Compounds 6, 7, 8, 9, 56, and 57 in Table 1 were prepared using methods similar to those described above in Example 3. These variations in the methods of Example 3 would be readily understood by those skilled in the art.

Compound 6 was prepared in a manner similar to that of Compound 11, except that in step 1, 2-pyridine thiol was used instead of 2-fluorobenzene thiol.

Compound 7 was prepared in a manner similar to that of Compound 6, except that in step 7, methanesulfonyl chloride was used instead of trifluoromethanesulfonic anhydride.

Compound 8 was prepared in a manner similar to that of Compound 6, except that in step 1, 2-fluoro-4-trifluoromethoxynitrobenzene was used instead of 2-fluoro-4-chloronitrobenzene.

Compound 9 was prepared in a manner similar to that of Compound 11, except that in step 7, methanesulfonyl chloride was used instead of trifluoromethanesulfonic anhydride.

Compound 56 was prepared in a manner similar to that of Compound 6, except that in step 7, the amine intermediate product prepared in step 6 was reacted with 2,2,2-trifluoroethyl triflate instead of Tf₂O.

Compound 57 was prepared according to General Scheme 1, wherein intermediate vi (where s=0 and R², R³, and R⁴=H) was reacted with n-BuLi followed by (t-BuOC(O))₂O. The intermediate vi was prepared in a manner similar to that of compound (1a) in Example 1 (i.e., by reacting amine B with TEA and 4-chlorobenzenesulfonyl chloride).

Example 4

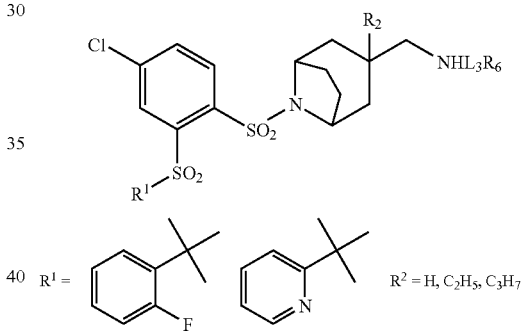

Compounds having the general structure shown above (i.e., Compounds 50, 51, 58 and 59) were prepared using procedures similar to those described in Example 3, except that amine C (in which R² is H or —CH₂CH₃) was used instead of amine B. These variations in the methods of Example 3 would be readily understood by those skilled in the art.

For example, Compounds 50 and 51 were prepared in a manner similar to that of Compounds 6 and 7, except that in step 4, amine C (R²=H) was used instead of amine B. Similarly, Compounds 58 and 59 were prepared in a manner similar to that of Compounds 56 and 6, respectively, except that in step 4, amine C (R²=—CH₂CH₃) was used instead of amine B.

Compound 55 was prepared according to General Scheme 1, wherein intermediate vii (where s=2, Z=—CH₂—, and R², R³, and R⁴=H) was reacted with n-BuLi followed by (t-BuOC(O))₂O. The intermediate vii was prepared in a manner similar to that of compound (1a) in Example 1 (i.e., by reacting amine C with TEA and 4-chlorobenzenesulfonyl chloride).

Example 5

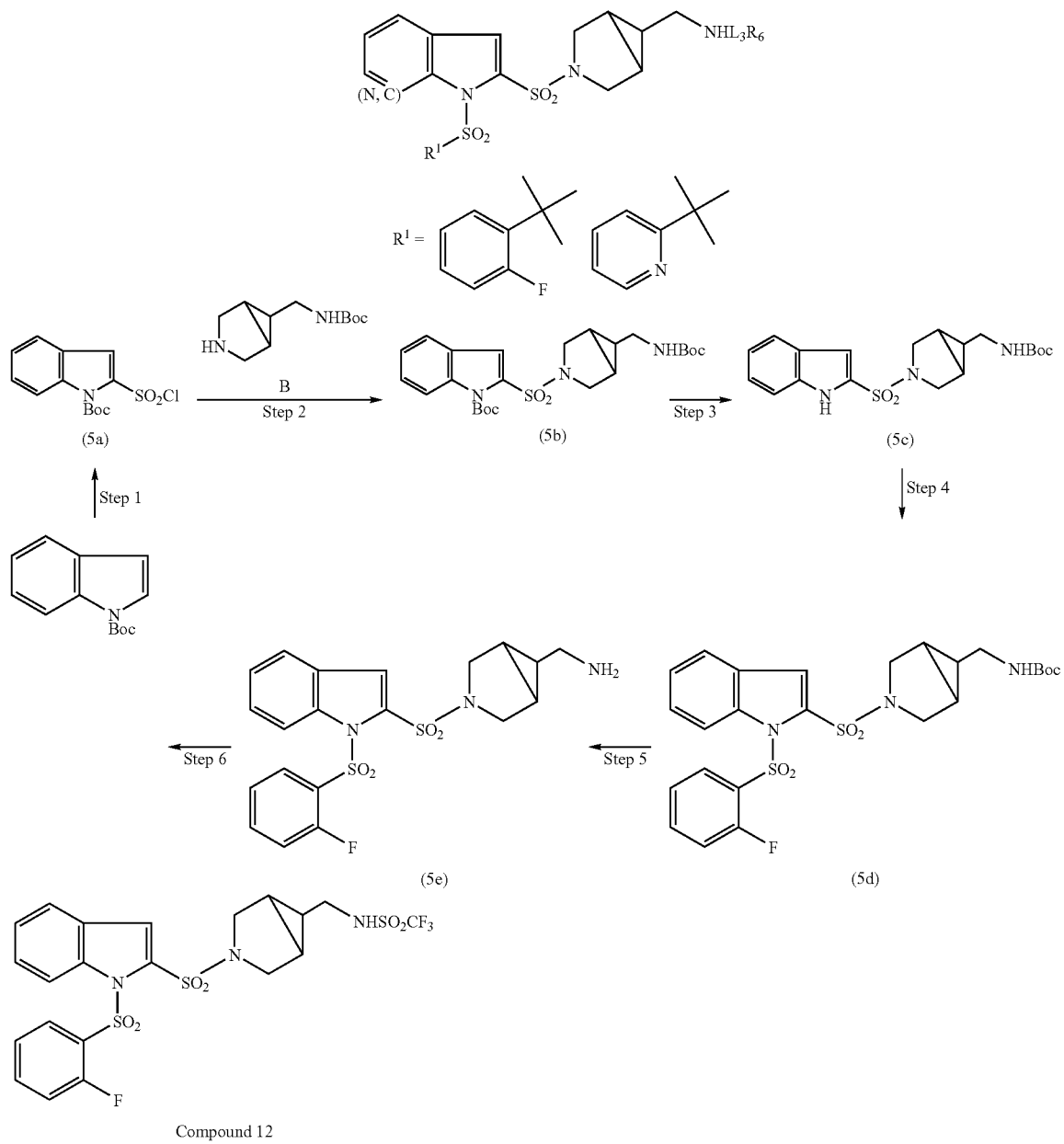

Compound 12

Step 1: n-BuLi (20.3 mL, 2.5M in hexanes, 50.6 mmol) was added dropwise over a period of 0.5 h to a THF solution (150 mL) of N-Boc indole (10.0 g, 46 mmol) maintained at −70° C. The mixture was stirred for 1 h and then $SO_2$ gas was bubbled into the solution for 1 h. The reaction mixture was then allowed to warm to 10° C. over a period of 2 h. The solvent was removed under reduced pressure and the residue was redissolved in $CH_2Cl_2$ (200 mL) and treated with NCS (9.2 g, 69 mmol) and stirred for 10 h. The reaction mixture was washed sequentially with water (2×50 mL), and brine (2×50 mL). The organic phase was dried and concentrated to provide a crude product which was passed through a pad of silica gel using 9:1 hexane:ethyl acetate as the eluting solvent. The fractions were collected and concentrated under vacuum to yield 19.5 g of indole sulfonyl chloride (5a).

Step 2: A solution of amine B (0.3 g, 1.4 mmol) and triethylamine (0.99 mL, 7 mmol) in $CH_2Cl_2$ (30 mL) at room temperature was treated with the indole sulfonyl chloride (5a) prepared in step 1 (0.5 g, 1.55 mmol). The mixture was stirred for 16 h and then diluted with $CH_2Cl_2$ (100 mL) and washed once with water (50 mL) and twice with brine (50 mL each wash). The organic phase was separated, dried ($Na_2SO_4$) and concentrated to yield a crude product which was purified by silica-gel chromatography using 1:1 ethyl acetate:hexane as the eluting solvent. The appropriate fractions were collected and combined, and the solvent was removed under vacuum to provide pure product (5b) (0.46 g).

Step 3: The product (5b) prepared in step 2 (0.45 g, 0.91 mmol) and LiOH (7 mL, 1 M H$_2$0 solution) in dioxane (25 mL) was heated at 40° C. for 16 h and then heated an additional 1 h at 60° C. The solvent was removed and the residue was dissolved in ethyl acetate (50 mL) and washed with water (50 mL) and brine (50 mL). The organic phase was dried (Na$_2$SO$_4$) and concentrated to yield a crude product, which was then subjected to silica gel preparative plate chromatography to yield 0.36 g of pure product (5c).

Step 4: A solution of product (5c) prepared in step 3 (0.25 g, 0.64 mmol) in DMF (20 mL) was treated with CsCO$_3$ (0.5 g, 1.6 mmol) followed by 2-fluorophenyl sulfonyl chloride (0.15 g, 0.7 mmol) and stirred for 40 h. The reaction mixture was then diluted with ethyl acetate (50 mL) and washed with water (50 mL) and brine (50 mL). The organic phase was dried and concentrated to provide a crude product which was purified by silica-gel preparative plate chromatography using ethyl acetate:hexane (1:2) to yield pure product (5d) (0.25 g).

Step 5: A room temperature solution of product (5d) prepared in step 4 (0.07 g, 0.13 mmol) in CH$_2$Cl$_2$ (50 mL) was treated with trifluoroacetic acid (0.07 g, 0.636 mmol). The reaction mixture was stirred for 3 h and then the solvent was removed to yield an amine product (5e), which was used in the next step without additional purification.

Step 6: The amine product (5e) prepared in step 5 and triethylamine (0.024 mL, 0.14 mmol) were dissolved in CH$_2$Cl$_2$ (15 mL) and cooled to −70° C. Trifluoromethanesulfonic anhydride (0.034 g, 0.042 mmol) was added to this solution and stirred for 1 h. The reaction mixture was then warmed to 0° C., diluted with CH$_2$Cl$_2$ (50 mL) and washed twice with water (15 mL each wash) and once with brine (15 mL). The organic phase was dried (Na$_2$SO$_4$), concentrated and the resulting crude product was purified by silica-gel preparative plate chromatography using 1:2 ethyl acetate:hexane to provide 0.025 g of pure Compound 12.

Compounds 3, 10, 13, 14, and 15 in Table 1 were prepared using methods similar to those described above in Example 5. These variations in the methods of Example 5 would be readily understood by those skilled in the art.

For example, Compound 3 was prepared in a manner similar to that of Compound 12, except that in step 1, protected azaindole

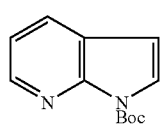

was used instead of N-Boc indole.

Compound 10 was prepared in a manner similar to that of Compound 12, except that in step 4, 2-pyridyl sulfonyl chloride was used instead of 2-fluorophenyl sulfonyl chloride, and in step 6, methanesulfonyl chloride was used instead of trifluoromethanesulfonic anhydride.

Compound 13 was prepared in a manner similar to that of Compound 12, except that in step 6, methanesulfonyl chloride was used instead of trifluoromethanesulfonic anhydride.

Compound 14 was prepared in a manner similar to that of Compound 12, except that in step 1, protected 5-cyano indole

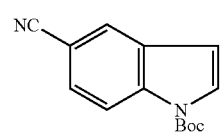

was used instead of N-Boc indole, and in step 4, 2-pyridyl sulfonyl chloride was used instead of 2-fluorophenyl sulfonyl chloride.

Compound 15 was prepared in a manner similar to that of Compound 12, except that in step 4, 2-pyridylsulfonyl chloride was used instead of 2-fluorophenyl sulfonyl chloride.

Example 6

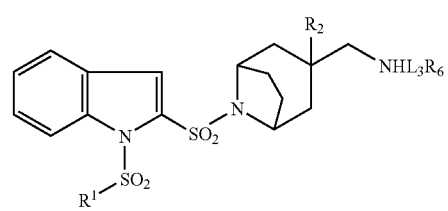

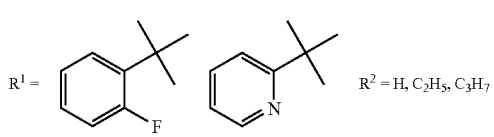

Compounds having the general structure shown above were prepared using procedures similar to those described in Example 5, except that amine C (i.e., R$^2$=H or —CH$_2$CH$_3$) was used instead of amine B. These variations in the methods of Example 5 would be readily understood by those skilled in the art. For example, Compounds 46-49 were prepared in a manner similar to that of Compounds 12, 13, 15, 10, respectively, except that amine C (R$^2$=H) was used instead of amine B. Similarly, Compound 54 was prepared in a manner similar to that of Compound 12, except that amine C (R$^2$=—CH$_2$CH$_3$) was used instead of amine B.

Example 7

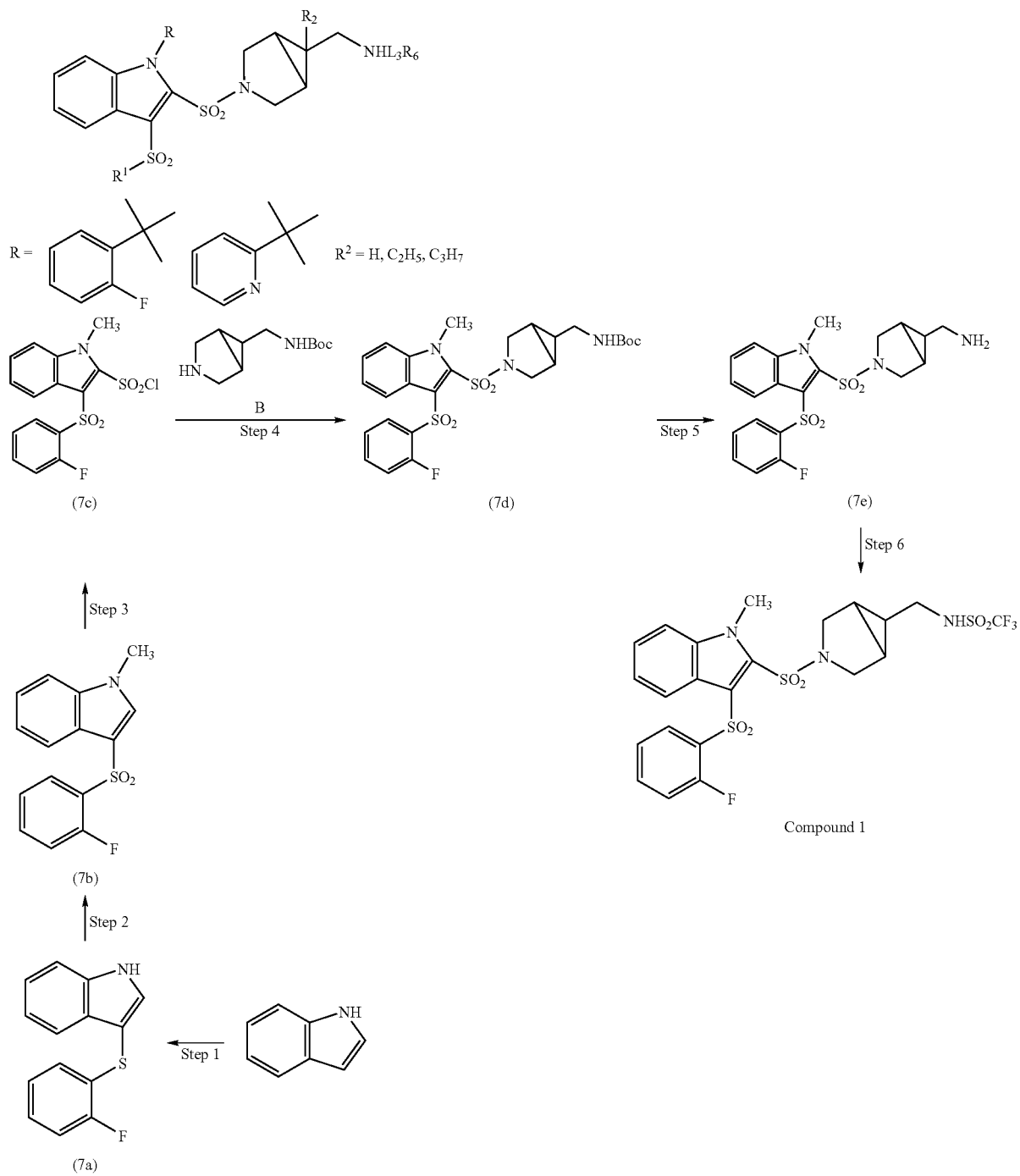

Step 1: Indole (2.4 g, 20 mmol) was added to a DMF solution (100 mL) containing NaH (0.78 g) at 0° C. After stirring the solution for 15 minutes, 2-fluorophenyidisulfide (5.2 g, 20 mmol) was added and the reaction mixture was allowed to warm up to room temperature over a period of 4 h. The solvent was removed and the crude product was redissolved in ethyl acetate (100 mL) and then was washed sequentially with water (50 mL) and brine (50 mL). The organic phase was dried and concentrated. The resulting product was recrystallized from a hexane:ethyl acetate mixture, thereby providing (7a) as a white solid (3.7 g).

Step 2: A solution of (7a) prepared in step 1 (2.5 g, 10 mmol) in $CH_2Cl_2$ (50 mL) was treated with m-CPBA (10.6 g, 62 mmol), in portions, and the resulting mixture was then stirred for 40 h. The reaction mixture was diluted with 100 mL $CH_2Cl_2$ and washed sequentially with aqueous $NaHSO_3$, (50 mL), aqueous NaHCO₃ (50 mL), and brine (50 mL). The organic phase was dried and concentrated to yield a crude product, which was methylated using the following procedure without further purification.

The crude product prepared above was dissolved in THF (50 mL) and treated with NaH (0.864 g, 36 mmol) followed by iodomethane (3.4 mL, 36 mmol). The mixture was then stirred for 20 h, quenched with 5 mL water, diluted with ethyl acetate (100 mL) and washed sequentially with water (50 mL) and brine (50 mL). The organic phase was dried and concentrated to yield a crude product (7b), which was purified by silica gel chromatography (using 3:7 ethyl acetate:hexanes as the eluting solvent).

Step 3: A solution of (7b) prepared in step 2 (1.4 g, 4.8 mmol) in anhydrous THF (40 mL) was cooled to −78° C., treated dropwise with lithium diisopropylamide (7 mmol), stirred for 40 min, and then SO₂ gas was bubbled through the solution for 0.5 h. The reaction mixture was stirred at −78° C. for 15 h, and then warmed to room temperature. The volume of the solution was reduced to 15 mL under reduced pressure and cooled hexane was added, thereby causing a solid to precipitate out of solution. The precipitate was collected by filtration and washed with cold hexane (50 mL). The solid was redissolved in CH₂Cl₂ (50 mL) and treated with N-chlorosuccinimide (1.3 g, 9.5 mmol) and stirred for 0.5 h. The reaction mixture was then washed sequentially with water (50 mL) and brine (50 mL), and then dried (Na₂SO₄). The solvent was removed and the crude product was passed through a pad of silica gel and eluted with ethyl acetate:hexane (1:2) and concentrated to provide pure product (7c) (1.4 g, 75%).

Step 4: A solution of amine B (0.17 g, 0.8 mmol) and triethylamine (0.55 mL, 3.94 mmol) in methylene chloride (25 mL) was treated with the sulfonyl chloride (7c) (0.28 g, 0.78 mmol) prepared in step 3. The reaction mixture was stirred at room temperature for 10 h, diluted with methylene chloride (50 mL) and washed sequentially with aqueous NaHCO₃ (50 mL), water (two aliquots of 50 mL each), and brine (50 mL). The organic phase was dried and concentrated to yield a crude product. The crude product was purified by preparative plate silica gel chromatography using 1:2 ethyl actetate:hexane as the eluting solvent, thereby providing 0.26 g of pure product (7d).

Step 5: A solution of the carbamate (7d) prepared in step 4 (0.25 g, 0.44 mmol) in CH₂Cl₂ (20 mL) was treated with trifluoroacetic acid (0.2 mL, 2.6 mmol) and stirred for 4 h. The reaction mixture was neutralized with aqueous NaHCO₃ diluted with CH₂Cl₂ (50 mL), and washed sequentially with water (50 mL) and brine (30 mL). The organic phase was dried (Na₂SO₄) and concentrated to yield pure amine (7e) (0.18 g).

Step 6: A solution of the amine (7e) (0.09 g, 0.19 mmol) prepared in step 5 and triethylamine (0.032 mL, 0.23 mmol) in CH₂Cl₂ (20 mL) was cooled to −70° C. and treated with trifluoromethanesulfonic anhydride (0.048 g, 0.173 mmol). The reaction mixture was stirred for 1 h and then quenched with aqueous NaHCO₃ (20 mL). The resulting mixture was warmed to room temperature and diluted with CH₂Cl₂ (50 mL). The organic phase was dried and concentrated, and the resulting crude product was subjected to silica gel preparative plate chromatography using 5% CH₃OH/CH₂Cl₂ as the developing solvent to provide pure Compound 1 (0.06 g).

Compounds 2, 4, and 5 were prepared using methods similar to those described in Example 7, and which would readily be understood by those skilled in the art. For example, Compound 2 was prepared by methods similar to those by which Compound 1 was prepared, except that in step 6, methanesulfonyl chloride was used instead of trifluoromethanesulfonic anhydride. Compounds 4 and 5 were prepared by methods similar to those of Compounds 1 and 2, respectively, except that in step 2, the indole nitrogen atom was alkylated with isopropyl bromide rather than methyl iodide.

Example 8

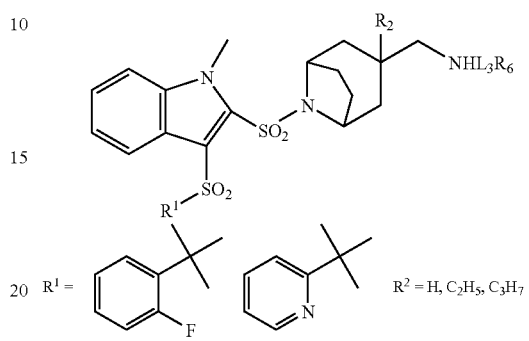

$R^1 =$ <br> $R^2 = H, C_2H_5, C_3H_7$

Compounds having the general structure shown above were prepared using procedures similar to those described in Example 7, except that amine C was used instead of amine B. These variations in the method of Example 7 would be readily understood by those skilled in the art. For example, Compounds 52 and 53 were prepared in a manner similar to that of Compounds 2 and 1, respectively, except that amine C was used instead of amine B.

Example 9

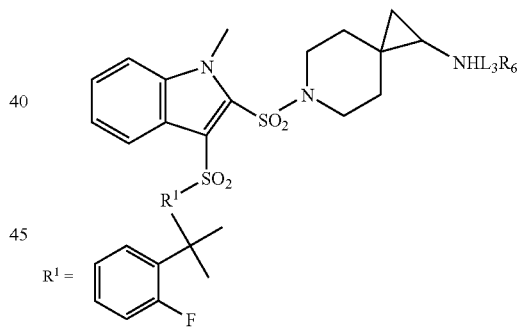

$R^1 =$

Compounds having the general structure shown above were prepared using procedures similar to those described in Example 7, except that amine A was used instead of amine B. These variations in the method of Example 7 would be readily understood by those skilled in the art. For example, Compounds 44 and 45 were prepared in a manner similar to that of Compounds 1 and 2, respectively, except that amine A was used instead of amine B.

Those skilled in the art will appreciate that reactions similar to those described in the above schemes may be carried out to prepare other compounds of Formula I. Starting materials for the above processes are either commercially available, known in the art, or prepared by procedures well known in the art.

The compounds of the present invention exhibit anti-inflammatory and/or immunomodulatory activity and are useful in the treatment of various medical conditions including, e.g., rheumatoid arthritis, systemic lupus erythematosus, multiple sclerosis, glaucoma, diabetes, osteoporosis, renal ischemia, cerebral stroke, cerebral ischemia, nephritis, psoriasis, allergy, inflammatory disorders of the lungs and gastrointestinal tract such as Crohn's disease, and respiratory tract disorders such as reversible airway obstruction, asthma, chronic obstructive pulmonary disease (COPD) and bronchitis. This utility is manifested as demonstrated by activity in the following assay.

Potential cannabinoid receptor ligands were screened for the ability to compete with [$^3$H] CP-55,940, which is a known receptor ligand, for binding to recombinant cannabinoid receptors. Test compounds were serially diluted in Diluent Buffer (50 mM Tris pH 7.1, 1 mM EDTA, 3 mM MgCl$_2$, 0.1% BSA, 10% DMSO, 0.36% methyl cellulose (Sigma M-6385)) from stocks prepared in 100% DMSO. Aliquots (10 μL) were transferred into 96-well microtiter plates. Membrane preparations of recombinant human cannabinoid CB$_2$ receptor (Receptor Biology #RB-HCB2) or recombinant human cannabinoid CB$_1$ receptor (Receptor Biology #RB-HCB1) were diluted to 0.3 mg/mL in Binding Buffer (50 mM Tris pH 7.2, 1 mM EDTA, 3 mM MgCl$_2$, 0.1% BSA). Aliquots (50 μL) were added to each well of the microtiter plate. The binding reactions were initiated by addition of [$^3$H] CP-55,940 (New England Nuclear #NET 1051; specific activity=180 Ci/mmol) to each well of the microtiter plate. Each 100 μl reaction mixture contained 0.48 nM [$^3$H] CP-55,940, 15 μg membrane protein in binding buffer containing 1% DMSO and 0.036% methyl cellulose. Following incubation for 2 hours at room temperature, the reactions were filtered through 0.5% polyethylenimine-coated GF/C filter plates (UniFilter-96, Packard) with a TomTec Mark 3U Harvester (Hamden, Conn.). The filter plate was washed 5 times with binding buffer, rotated 180°, then re-washed 5 times with binding buffer. Bound radioactivity was quantitated following addition of 30 μl of Packard Microscint 20 scintillant in a Packard TopCount NXT microplate scintillation counter. Non-linear regression analysis of the resulting data was performed using Prism 2.0b (GraphPad, San Diego, Calif.).

Compounds of the present invention were found to exhibit potent affinities for the CB$_2$ receptor as measured by Ki values (in nM). The activities (potencies) for the compounds of the invention are determined by measuring their K$_i$ values. The smaller the Ki value, the more active the compound is for modulating the CB$_2$ receptor. Compounds of the invention exhibit a wide range of activities. The CB$_2$ average Ki values for compounds having the Formula I generally range from >0 nM (e.g., 0.01 nM) to about 1000 nM, preferably about 0.1 nM to about 1000 nM, more preferably about 0.1 nM to about 100 nM, even more preferably about 0.1 nM to about 20 nM. Most preferred are compounds having average Ki values of less than about 20 nM for the CB$_2$ receptor.

Compounds of the present invention were found to exhibit CB2 receptor binding activity in the range of 0.1 to 1000 nM. For example, compounds 20, 41, 9, 13, 22, 11, 6, 60, 61, 31, 47, 59, 62, and 58 have K$_i$ values, respectively, of 0.24, 0.4, 0.65, 1, 1, 1.46, 1.5, 3.3, 3.9, 5, 7, 25.9, 28, and 41 nM.

The inventive compounds are also highly selective for modulating a receptor, as opposed to modulating a CB$_1$ receptor. A "selective modulator" means that a compound's selection ratio of K$_i$ of the CB$_1$ receptor to the K$_i$ of the CB$_2$ receptor is greater than about 1, preferably greater than about 100, more preferably greater than about 500, even more preferably greater than about 1000, and most preferably greater than about 3000. For example, compounds 20, 41, 9, 13, 22, 11, 6, 60, 61, 31, 47, 59, 62, and 58 have a selection ratio of the K$_i$ value of the CB$_1$ receptor to that of the CB$_2$ receptor of, respectively, about 15000, 3500, 2700, 3400, 400, 1000, 6300, 4100, 1200, 71, 790, 52, 1.9, and 770.

We claim:

1. A compound of Formula I:

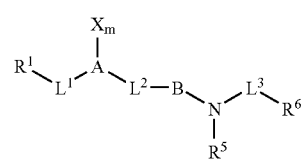

or a pharmaceutically acceptable salt of said compound, wherein:

A is selected from the group consisting of phenyl and naphthyl;

B is B1:

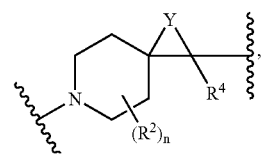

Y is —CH$_2$—;

L$^1$ is selected from the group consisting of —C(O)—, —CH$_2$—, —S(O$_2$)—, —S(O)—, —S—, and —CF$_2$—;

L$^2$ is selected from the group consisting of —C(O)—, —CH$_2$—, —S(O$_2$)—, —S(O)—, —S—, and —CF$_2$—;

L$^3$ is selected from the group consisting of —C(O)—, —CH$_2$—, —S(O$_2$)—, —S(O)—, —S—, and —CF$_2$—;

R$^1$ is selected from the group consisting of fluorophenyl, pyridyl, trifluoromethoxyphenyl, and methoxyphenyl;

R$^2$ is selected from the group consisting of H and alkyl;

R$^4$ is H or alkyl;

R$^5$ is H;

R$^6$ is selected from the group consisting of hydrogen, alkyl, haloalkyl, and cycloalkyl;

each X is independently selected from H, halogen, —CN, —OH, alkyl, haloalkyl, alkoxy, haloalkoxy, and cycloalkyl; and m is an integer of from 0 to 4.

2. The compound according to claim 1, wherein:

R$^1$ is selected from the group consisting of fluorophenyl, pyridyl, trifluoromethoxyphenyl, and methoxyphenyl;

L$^1$ is selected from the group consisting of —C(O)—, —CH$_2$—, —S(O$_2$)—, —S(O)—, and —CF$_2$—;

L$^2$ is selected from the group consisting of —C(O)—, —CH$_2$—, —S(O$_2$)—, —S(O)—, and —CF$_2$—;

L$^3$ is selected from the group consisting of —C(O)—, —CH$_2$—, —S(O$_2$)—, —S(O)—, and —CF$_2$—;

R$^2$ is H, methyl, or ethyl;

R$^5$ is H;

R$^6$ is H, (C$_1$-C$_6$)alkyl, (C$_3$-C$_5$)cycloalkyl, or haloalkyl; and

X is independently selected from the group consisting of H, halogen, alkyl, haloalkyl, (C$_3$-C$_5$)cycloalkyl, —OH, alkoxy, haloalkoxy and —CN.

3. The compound according to claim 1, wherein A is represented by Formula A1:

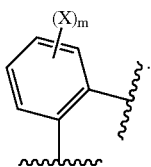

4. The compound according to claim 1, wherein L$^1$, L$^2$, and L$^3$ are independently —S(O$_2$)—, or —CH$_2$—.

5. The compound according to claim 1, wherein L$^1$, L$^2$, and L$^3$ are each —S(O$_2$)—.

6. The compound according to claim 1, wherein R$^1$ is selected from the group consisting of 2-fluorophenyl, 2-pyridyl, 4-methoxyphenyl, and 4-trifluoromethoxyphenyl.

7. The compound according to claim 1, wherein R$^6$ is selected from the group consisting of —CH$_3$, —CF$_3$, and cyclopropyl.

8. The compound according to claim 1, represented by Formula IV:

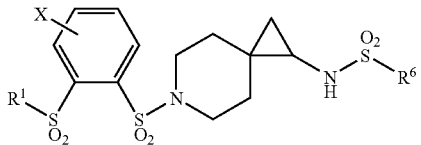

wherein X is selected from the group consisting of H, F, Cl, Br, —CH$_3$, —CF$_3$, —OCH$_3$, —OCF$_3$, —OH, and —CN;

R$^1$ is selected from the group consisting of 2-fluorophenyl, 2-pyridyl, 4-methoxyphenyl, and 4-trifluoromethoxyphenyl;

R$^2$ is selected from the group consisting of H and ethyl; and

R$^6$ is selected from the group consisting of methyl, trifluoromethyl, and cyclopropyl.

9. The compound according to claim 1, represented by Formula IV:

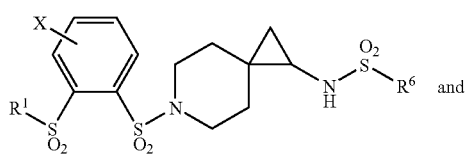

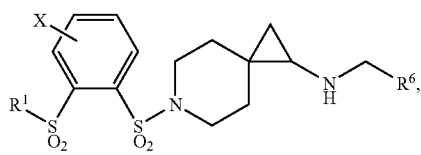

wherein X is selected from the group consisting of H, F, Cl, Br, —CH$_3$, —CF$_3$, —OCH$_3$, —OCF$_3$, —OH, and —CN;

R$^1$ is selected from the group consisting of 2-fluorophenyl, 2-pyridyl, 4-methoxyphenyl, and 4-trifluoromethoxyphenyl;

R$^2$ is selected from the group consisting of H and ethyl; and

R$^6$ is selected from the group consisting of methyl, trifluoromethyl, and cyclopropyl.

10. The compound according to claim 1, wherein R$^5$ is H, n=1, m=1, L$^2$ is —S(O$_2$)—, and L$^1$, L$^3$, R$^1$, R$^6$, —A—X, —B—N(R$^5$)— and X are as set forth in the following Table:

| Cmpd | R¹ (with linking point to L¹) | R⁶ | X | L¹ | L³ | —A—X (with linking points to L¹, L² and X) | —B—N(R⁵) (with linking points to L² and L³) |
|---|---|---|---|---|---|---|---|
| P | 2-F-phenyl (L¹ at position 1) | CH₃ | Cl | —S(O₂)— | —S(O₂)— | 1,2,4-trisubstituted benzene (X, L², L¹) | spiro[cyclopropane-piperidine] with NH-L³ and N-L² |
| Q | 2-F-phenyl (L¹ at position 1) | CF₃ | Cl | —S(O₂)— | —S(O₂)— | 1,2,4-trisubstituted benzene (X, L², L¹) | spiro[cyclopropane-piperidine] with NH-L³ and N-L² |
| T | pyridin-2-yl (L¹) | CF₃ | Cl | —S(O₂)— | —S(O₂)— | 1,2,4-trisubstituted benzene (X, L², L¹) | spiro[cyclopropane-piperidine] with NH-L³ and N-L² |
| W | 4-F₃CO-phenyl (L¹) | CF₃ | Cl | — | —S(O₂)— | 1,2,4-trisubstituted benzene (X, L², L¹) | spiro[cyclopropane-piperidine] with NH-L³ and N-L² |
| X | 4-H₃CO-phenyl (L¹) | CF₃ | Cl | — | —S(O₂)— | 1,2,4-trisubstituted benzene (X, L², L¹) | spiro[cyclopropane-piperidine] with NH-L³ and N-L² |

| Cmpd | R¹ (with linking point to L¹) | R⁶ | X | L¹ | L³ | —A—X (with linking points to L¹, L² and X) | —B—N(R⁵) (with linking points to L² and L³) |
|---|---|---|---|---|---|---|---|
| Y | 2-fluorophenyl | CF₃ | CF₃ | —S(O₂)— | —S(O₂)— | phenyl with X, L¹, L² | spiro cyclopropane-piperidine with L², L³ |
| Z | 4-(trifluoromethoxy)phenyl | CF₃ | CF₃ | —S(O₂)— | —S(O₂)— | phenyl with X, L¹, L² | spiro cyclopropane-piperidine with L², L³ |
| AA | pyridin-2-yl | CF₃ | CF₃ | —S(O₂)— | —S(O₂)— | phenyl with X, L¹, L² | spiro cyclopropane-piperidine with L², L³ |
| AB | 2-fluorophenyl | CF₃ | OCF₃ | —S(O₂)— | —S(O₂)— | phenyl with X, L¹, L² | spiro cyclopropane-piperidine with L², L³ |
| AC | pyridin-2-yl | CF₃ | OCH₃ | —S(O₂)— | —S(O₂)— | phenyl with X, L¹, L² | spiro cyclopropane-piperidine with L², L³ |

-continued
| Cmpd | R¹ (with linking point to L¹) | R⁶ | X | L¹ | L³ | —A—X (with linking points to L¹, L² and X) | —B—N(R⁵) (with linking points to L² and L³) |
|---|---|---|---|---|---|---|---|
| AD | 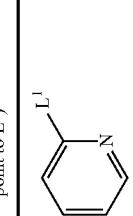 | CF₃ | H | —S(O₂)— | —S(O₂)— | 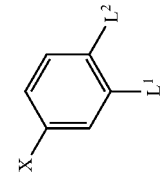 | 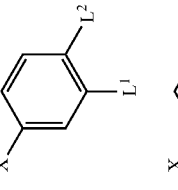 |
| AE | 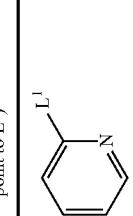 | CF₃ | F | —S(O₂)— | —S(O₂)— | 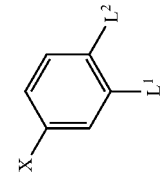 | 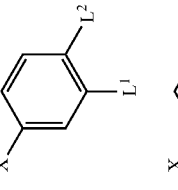 |
| AF | 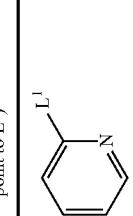 | CH₃ | Cl | —S(O₂)— | —S(O₂)— | 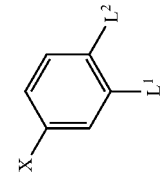 | 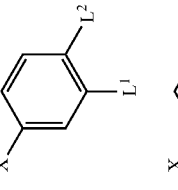 |
| AG | 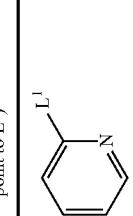 | 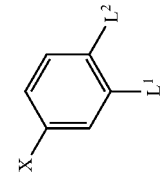 | Cl | —S(O₂)— | —S(O₂)— | 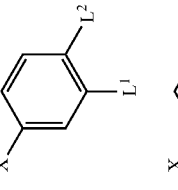 | 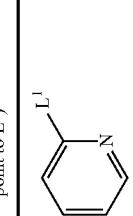 |
| AH | 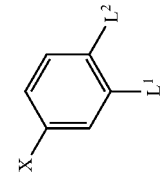 | CF₃ | OH | —S(O₂)— | —S(O₂)— | 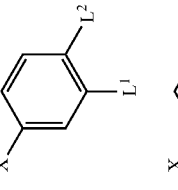 | |

-continued
| Cmpd | R¹ (with linking point to L¹) | R⁶ | X | L¹ | L³ | —A—X— (with linking points to L¹, L² and X) | —B—N(R⁵)— (with linking points to L² and L³) |
|---|---|---|---|---|---|---|---|
| AI |  | CF₃ | OCF₃ | —S(O₂)— | —CH₂— |  | 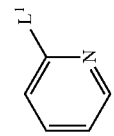 |
| AJ |  | CF₃ | OCF₃ | —S(O₂)— | —S(O₂)— | 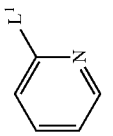 |  |

11. The compound according to claim 1, wherein $R^5$ is H, n=1, m=1, $L^2$ is —S($O_2$)—, and $L^1$, $L^3$, $R^1$, $R^6$, —A—X, —B—N($R^5$)— and X are as set forth in the following Table:

| Cmpd | $R^1$ (with linking point to $L^1$) | $R^6$ | X | $L^1$ | $L^3$ | —A—X (with linking points to $L^1$, $L^2$ and X) | —B—N($R^5$) (with linking points to $L^2$ and $L^3$) |
|---|---|---|---|---|---|---|---|
| AA | 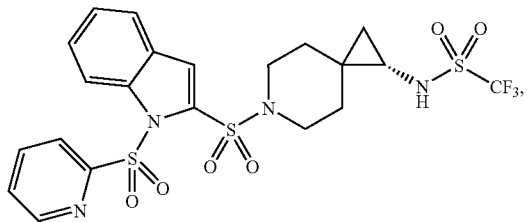 | $CF_3$ | $CF_3$ | —S($O_2$)— | —S($O_2$)— | | |

12. A compound having the following structure:

or a stereoisomer thereof, or a salt of said compound or said stereoisomer.

13. A pharmaceutical composition comprising one or more compounds according to claim 1, and one or more pharmaceutically acceptable carriers.

14. A compound of claim 1 in purified form.

* * * * *